United States Patent
Crudden et al.

(10) Patent No.: US 11,383,266 B2
(45) Date of Patent: *Jul. 12, 2022

(54) CARBENE-FUNCTIONALIZED COMPOSITE MATERIALS

(71) Applicant: Queen's University at Kingston, Kingston (CA)

(72) Inventors: Cathleen M. Crudden, Kingston (CA); J. Hugh Horton, Kingston (CA); Olena V. Zenkina, Oshawa (CA); Iraklii I. Ebralidze, Oshawa (CA); Christene Anne Smith, Kingston (CA)

(73) Assignee: Queen's University at Kingston, Kingston (CA)

( * ) Notice: Subject to any disclaimer, the term of this patent is extended or adjusted under 35 U.S.C. 154(b) by 547 days.

This patent is subject to a terminal disclaimer.

(21) Appl. No.: 14/912,900

(22) PCT Filed: Aug. 19, 2014

(86) PCT No.: PCT/CA2014/050794
§ 371 (c)(1),
(2) Date: Feb. 18, 2016

(87) PCT Pub. No.: WO2015/024120
PCT Pub. Date: Feb. 26, 2015

(65) Prior Publication Data
US 2016/0199875 A1    Jul. 14, 2016

Related U.S. Application Data

(60) Provisional application No. 62/018,782, filed on Jun. 30, 2014, provisional application No. 61/867,466, filed on Aug. 19, 2013.

(51) Int. Cl.
*B05D 1/18* (2006.01)
*B32B 15/04* (2006.01)
*G01N 21/552* (2014.01)

(52) U.S. Cl.
CPC ............... *B05D 1/18* (2013.01); *B32B 15/04* (2013.01); *G01N 21/554* (2013.01); *B32B 2457/00* (2013.01)

(58) Field of Classification Search
CPC ....................................................... B05D 1/18
See application file for complete search history.

(56) References Cited

U.S. PATENT DOCUMENTS 5,395,587 A * 3/1995 Brigham-Burke ... G01N 21/553
  422/502
9,150,515 B2 * 10/2015 Kuehl .................. C07D 233/60
2007/0123666 A1 * 5/2007 Chung ..................... C08F 4/70
  526/171

FOREIGN PATENT DOCUMENTS

EP          2030677 A2    3/2009
WO    WO-2014/160471 A2   10/2014

OTHER PUBLICATIONS

Weidner et al, Aust J Chem, 2011, 64(8), 1177-1179.*
Siemeling et al, Aust J Chem 2011, 64(8) 1177-1179.*
Huynh et al, Organometallics, 2006,25,3267-3274.*
Jacobsen et al, Coordination Chemistry Reviews 253 (2009) 687-703 (Year: 2009).*
Kalluri et al, Angew.Chem.Int.Ed. 2010, 49,7786-7789 (Year: 2010).*
Mercs et al., "Beyond catalysis: N-heterocyclic carbene complexes as components for medicinal, luminescent, and functional materials applications," Chem Soc Rev. 39(6):1903-12 (2010) (10 pages).
International Preliminary Report on Patentability for International Application No. PCT/CA2014/050794, dated Mar. 3, 2016 (6 pages).
Written Opinion for International Application No. PCT/CA2014/050794, dated Nov. 3, 2014 (4 pages).
International Search Report for International Application No. PCT/CA2014/050794, dated Nov. 3, 2014 (2 pages).
International Search Report for International Application No. PCT/CA2014/050794, dated Oct. 23, 2014 (3 pages).
Bain et al., "Formation of monolayer films by the spontaneous assembly of organic thiols from solution onto gold," J. Am. Chem. Soc. 111(1): 321-35 (1989).
Vericat et al., "Self-assembled monolayers of thiols and dithiols on gold: new challenges for well-known system," Chem. Soc. Rev. 39(5): 1805-34 (2010).
Schoenfisch et al., "Air stability of alkanethiol self-assembled monolayers on silver and gold surfaces," J. Am. Chem. Soc. 120(18): 4502-13 (1998).
Schlenoff et al., "Stability and self-exchange in alkanethiol monolayers," J. Am. Chem. Soc. 117(50): 12528-36 (1995).
Vericat et al., "Thiol-capped gold: from planar to irregular surfaces," J Phys: Condens Matter. 20:184004 (2008) (8 pages).
Yang et al., "Molecular-level approach to inhibit degradations of alkanethiol self-assembled monolayers in aqueous media," Langmuir. 20(10): 3995-4003 (2004).
Chinwangso et al., "Multidentate adsorbates for self-assembled monolayer films," Acc Chem Res. 44(7): 511-19 (2011).
Jewell et al., "Gently lifting gold's herringbone reconstruction: trimethylphosphine on Au(111)," Phys. Rev. B. 82:205401 (2010) (6 pages).
Herrmann, "N-heterocyclic carbenes: a new concept in organometallic catalysis," Angew. Chem. Int. Ed. Engl. 41(8): 1290-1309 (2002).

(Continued)

Primary Examiner — Irina Krylova
(74) Attorney, Agent, or Firm — Angela Lyon; Vanessa Renee Little

(57) ABSTRACT

The present application provides stable, carbene-functionalized composite materials, and methods and uses thereof. These carbene-functionalized composite materials comprise a material having a metal surface, and a carbene monolayer that is uniform, contaminant-free (metal oxide, etc), and more stable than thiol-functionalized monolayers. Uses of such carbene-functionalized composite materials include semi-conducting materials, microelectronic devices, drug delivery or sensing applications.

6 Claims, 24 Drawing Sheets

(56) References Cited

OTHER PUBLICATIONS

Niehues et al., "Synthesis and structural features of arduengo carbene complexes of group 4 metallocene cations," Organometallics. 21(14): 2905-11 (2002).
Arduengo et al., "A stable crystalline carbene," J. Am. Chem. Soc. 113(1): 361-3 (1991).
Buenger et al., "Hydrogels in sensing applications," Progress in Polymer Science. 37(12): 1678-1719 (2012).
Zahidi et al., "Formation of thermally stable alkylidene layers on a catalytically active surface," Nature. 409(6823): 1023-6 (2001).
Tulevski et al., "Formation of catalytic metal-molecule contacts," Science. 309(5734): 591-4 (2005).
Zhukhovitskiy et al., "Addressable carbene anchors for gold surfaces," J. Am. Chem. Soc. 135(20): 7418-21 (2013).
Vignolle et al., "N-heterocyclic carbene-stabilized gold nanoparticles and their assembly into 3D superlattices," Chem Commun (Camb). (46): 7230-2 (2009).
Hurst et al., "N-heterocyclic carbene coated metal nanoparticles," New J. Chem. 33(9): 1837-40 (2009).
Huang et al., "Liquid crystals of gold(l) N-heterocyclic carbene complexes," Dalton Trans. (35):7121-31 (2009).
Pinson et al., "Attachment of organic layers to conductive or semiconductive surfaces by reduction of diazonium salts," Chem. Soc. Rev. 34(5): 429-39 (2005).
Laurentius et al., "Diazonium-derived aryl films on gold nanoparticles: evidence for a carbon-gold covalent bond," ACS Nano. 5(5): 4219-27 (2011).
Liu et al., "Fast colorimetric sensing of adenosine and cocaine based on a general sensor design involving aptamers and nanoparticles," Agnew. Chem. Int. Ed. Engl. 45(1): 90-4 (2006).
Kang et al., "Nuclear targeting of gold nanoparticles in cancer cells induces DNA damage, causing cytokinesis arrest and apoptosis," J. Am. Chem. Soc. 132(5): 1517-19 (2010).
Smith et al., "Patterning self-assembled monolayers," Prog. Surf. Sci. 75(1-2): 1-68 (2004).
Bhure et al., "Chapter 4: Surface patterning using self assembled monolayers (SAMs)," ACS Symposium Series, vol. 1054, 65-107 (2010).
Kumar et al., "Patterning self-assembled monolayers: applications in materials science," Langmuir 10, 1498-1511, (1994).
Enders et al., "Preparation, structure, and reactivity of 1,3,4-triphenyl-4,5-dihydro-1H-1,2,4-triazol-5-ylidene, a new stable carbene," Angew. Chem. Int. Ed. Engl. 34(9): 1021-3 (1995).
Arduengo et al., "Electronic stabilization of nucleophilic carbenes," J. Am. Chem. Soc. 114(14): 5530-4 (1992).
Arduengo et al., "Imidazolylidenes, imidazolinylidenes, and imidazolidines," Tetrahedron. 55(51): 14523-34(1999).
Jafarpour et al., "A sterically demanding nucleophilic carbene: 1,3-bis(2,6-diisopropylphenyl)imidazol-2-ylidene). Thermochemistry and catalytic application in olefin metathesis," J. Organomet. Chem. 606(1) 49-54 (2000).
Fèvre et al., "Imidazol(in)ium hydrogen carbonates as a genuine source of N-heterocyclic carbenes (NHCs): applications to the facile preparation of NHC metal complexes and to NHC-organocatalyzed molecular and macromolecular syntheses," J. Am. Chem. Soc. 134(15):6776-84 (2012).
Fèvre et al., "Imidazolium hydrogen carbonates versus imidazolium carboxylates as organic precatalysts for N-heterocyclic carbene catalyzed reactions," J. Org. Chem. 77(22):10135-44 (2012).
Brust et al., "Synthesis of thiol-derivatised gold nanoparticles in a two-phase liquid-liquid system," J Chem Soc, Chem Commun. pp. 801-802 (1994).
Cooper et al., "Surface plasmon resonance analysis at a supported lipid monolayer," Biochim Biophys Acta. 1373(1): 101-11 (1998).
Extended European Search Report for European Application No. 14838476.1, dated Jan. 2, 2017 (9 pages).
Communication Pursuant to Rules 70(2) and 70a(2)EPC for European Application No. 14838476.1, dated Jan. 19, 2017 (1 page).
Hara et al., "Construction of self-assembled monolayer with N-heterocyclic carbene-rhodium(l) complex moiety," Surface Science. 601(22): 5127-32 (2007).
Serpell et al., "Haloaurate and halopalladate imidazolium salts: structures, properties, and use as precursors for catalytic metal nanoparticles," Dalton Trans. 42(5): 1385-93 (2013).
Lee et al., "Characterization of a self-assembled monolayer of thiol on a gold surface and the fabrication of a biosensor chip based on surface plasmon resonance for detecting anti-GAD antibody," Biosens Bioelectron. 20(7): 1422-27 (2005).

\* cited by examiner

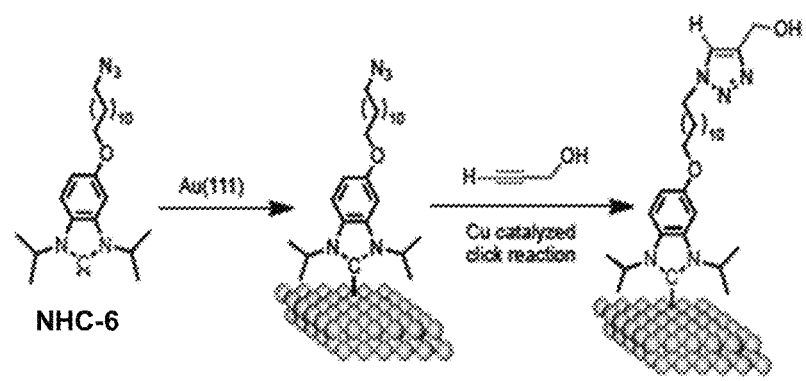
Fig. 3A
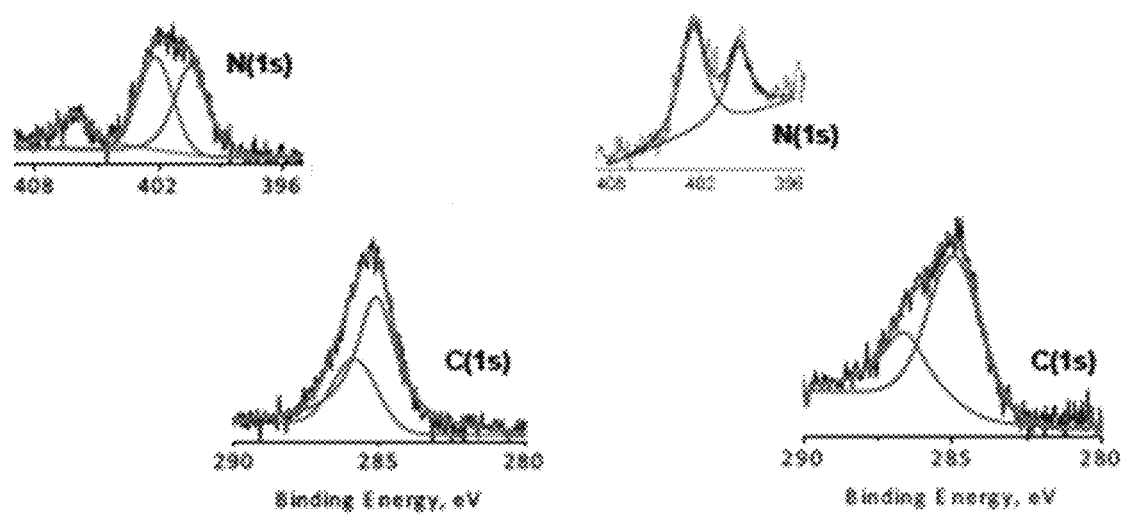
Fig. 3B                    Fig. 3C

Scheme 1:

CARBENE-FUNCTIONALIZED COMPOSITE MATERIALS

RELATED APPLICATIONS

This application claims the benefit of the filing dates of U.S. Provisional Patent Application No. 61/867,466, filed on Aug. 19, 2013, and U.S. Provisional Patent Application No. 62/018,782, filed on Jun. 30, 2014, the contents of which are incorporated herein by reference in their entirety.

FIELD OF THE INVENTION

The present application pertains to the field of materials science. More particularly, the present application relates to carbene-functionalized composite materials.

BACKGROUND

Self-assembled monolayers (SAMs) on metals such as gold have potential application in sensing, electrochemistry, drug delivery, surface protection, microelectronics and microelectromechanical systems, among others [R. G. Nuzzo, et al. *J. Am. Chem. Soc.* 105, 4481 (1983); B. D. Gates, et al. *Chem. Rev.* 105, 1171 (2005); J. C. Love, et al. *Chem. Rev.* 105, 1103 (2005); U. Drechsler, et al. *Chem.— Eur. J.* 10, 5570 (2004)]. Since a discovery of sulfur-based SAMs on gold [C. D. Bain et al. *J. Am. Chem. Soc.* 111, 321 (1989)], suitable alternatives for these ligands have not been found, despite the thiol-based SAMs' oxidative and thermal instability on gold being a significant impediment to their widespread use [C. Vericat, et al. *Chem. Soc. Rev.* 39, 1805 (2010)]. Thiol-based SAMs are stable when stored in ultra high vacuum in an absence of light [J. Noh, et al. *J. Phys. Chem. B* 110, 2793 (2006)], however degradation has been observed after as little as one to two weeks at room temperature in air [C. Vericat, et al. *J. Phys. Condens. Matter* 20, 184004 (2008); Y. Li, et al. *J. Am. Chem. Soc.* 114, 2428 (1992); M. H. Schoenfisch, et al. *J. Am. Chem. Soc.* 120, 4501 (1998); J. B. Schlenoff, et al. *J. Am. Chem. Soc.* 117, 12528 (1995)]. Improvements in stability can be accomplished by changing the gold surface's nature [C. Vericat, et al. *J. Phys. Condens. Matter* 20, 184004 (2008)], by addition of additives [G. Yang, et al. *Langmuir* 20, 3995 (2004)], or through use of multi-dentate thio-adsorbates [P. Chinwangso, A. C. Jamison, T. R. Lee, *Accounts of Chemical Research*, 44, 511 (2011)]. Phosphine-based ligands have also been examined, but offer weaker bonds to a surface [A. D. Jewell, et al. *Phys. Rev. B* 82, 205401 (2010)].

Carbon-based ligands known as N-heterocyclic carbenes (NHCs) have played a role in the field of transition metal complexes [W. A. Herrmann, *Angew. Chem. Int. Ed.* 41, 1290 (2002); E. Peris, et al. *Coord. Chem. Rev.* 248, 2239 (2004)]. These ligands are part of catalysts such as the Grubbs second generation metathesis catalyst [R. M. Thomas, et al. *Organometallics* 30, 6713 (2011)], and NHC-based cross-coupling catalysts [E. A. B Kantchev, et al. *Angew. Chem. Int. Ed.* 46, 2768 (2007)]. Unlike most carbenes, which are reactive with limited stability, NHCs typically have one or two heteroatoms adjacent to a carbene carbon [A. Igau, et al. *J. Am. Chem. Soc.* 110, 6463 (1988); A. J. Arduengo, et al. *J. Am. Chem. Soc.* 113, 361 (1991)]. These heteroatoms increase NHCs' stability such that they can usually be prepared on a gram scale [M. Niehues, et al. *Organometallics* 21, 2905 (2002)], crystallized [A. J. Arduengo, R. L. Harlow, M. Kline, *J. Am. Chem. Soc.* 113, 361 (1991)], distilled [M. Niehues, et al. *Organometallics* 21, 2905 (2002)], and stored for longer periods of time [4 years, when stored under $N_2$ in a freezer]. An Au-NHC bond is estimated to be on an order of 90 kJ/mol stronger than a corresponding Au-phosphine bond, and twice as strong as metal sulfide bonds in molecular complexes [P. Pyykkö, et al. *Chem. Asian J.* 1, 623 (2006)]. As such, NHCs have potential to be valuable ligands for protecting and functionalizing gold and other metal surfaces. Application of these carbenes in materials science, and other fields outside of homogeneous catalysis, has been limited [L. Mercs, et al. *Chem. Soc. Rev.* 39, 1903 (2010)].

The above information is provided for the purpose of making known information believed by the applicant to be of possible relevance to the present invention. No admission is necessarily intended, nor should be construed, that any of the preceding information constitutes prior art against the present invention.

SUMMARY OF THE INVENTION

An aspect of the application is to provide carbene-functionalized composite materials and methods of manufacture thereof. In accordance with one aspect, there is provided a carbene-functionalized composite material, comprising a carbene monolayer, and a material having at least a metal surface, wherein the carbene monolayer interacts with the metal surface and is stable, uniform, and/or substantially free of contamination. In one embodiment, the carbene monolayer comprises ≤5%, or ≤2% contamination.

In accordance with another embodiment, the carbene monolayer comprises one or more carbenes of formula I

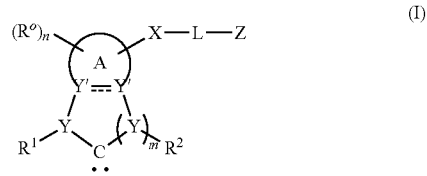

wherein:
n is an integer from 1 to 8, or from 1 to 4;
m is an integer from 0 to 4;
A is absent, an aliphatic cycle, a heterocycle, an aromatic ring, a fused aromatic ring system, a heteroaromatic ring, and/or a fused heteroaromatic ring system, each of which is optionally substituted;
X-L-Z is absent, or
X is C or a heteroatom,
L is a divalent moiety, such as $C_1$-$C_{10}$ alkylene, $C_{10}$-$C_{20}$ alkylene, $C_1$-$C_{10}$ alkenylene, $C_{10}$-$C_{20}$ alkenylene, $C_1$-$C_{10}$ alkynylene, $C_{10}$-$C_{20}$ alkynylene, or dextran, a simple sugar, complex sugar, carbohydrate, ether, thio-ether, amine, polyamine, polyether, and/or polythio-ether, each of which is optionally substituted;
Z is H, an aliphatic cycle, a heterocycle, an aromatic ring, a fused aromatic ring system, a heteroaromatic ring, a fused heteroaromatic ring system, an organometallic complex, a transition-metal catalyst, a metal-oxide catalyst, a simple sugar, a complex sugar, a carbohydrate, or a chemically derivatizable group, such as —OH, azide, carboxylic acid, carbonyl chloride, anhydride, ester, aldehyde, alcohol, amine, halogen, epoxide, thiirane, aziridine, amino acid, nucleic acid, alkene, alkyne, conjugated diene, thiol, or thioester, each of which is optionally substituted;

each Y or Y' is independently C or a heteroatom;

each R° is independently H, halogen, the substituent X-L-Z as defined above, $C_1$-$C_{10}$ alkyl, $C_{10}$-$C_{20}$ alkyl, $C_1$-$C_{10}$ alkenyl, $C_{10}$-$C_{20}$ alkenyl, $C_1$-$C_{10}$ alkynyl, or $C_{10}$-$C_{20}$ alkynyl, $C_1$-$C_{10}$ alkoxyl, $C_{10}$-$C_{20}$ alkoxyl, $C_3$-$C_{20}$ cyclic aliphatic moiety, aryl, heteroaryl, ether, thioether, amine, polyamine, polyether, or polythioether, each of which is optionally substituted; or, two of R°, together with the atoms to which they are attached, are connected to form a cycle, or heterocycle, each of which is optionally substituted; and $R^1$ and $R^2$ are independently absent, at least one lone pair of electrons, H, $C_1$-$C_{10}$ alkyl, $C_{10}$-$C_{20}$ alkyl$C_1$-$C_{10}$ alkenyl, $C_{10}$-$C_{20}$ alkenyl, $C_1$-$C_{10}$ alkynyl, $C_{10}$-$C_{20}$ alkynyl, $C_3$-$C_{20}$ cyclic aliphatic moiety, aryl, heteroaryl, ether, thiol, thioether, amine, polyamine, polyether, polythioether, or polythiol, each of which is optionally substituted; or, one of $R^1$ or $R^2$, with one of R°, together with the atoms to which they are attached, are connected to form a cycle, or heterocycle, each of which is optionally substituted;

wherein, when A is absent or non-aromatic, the dashed line represents an optional double bond; and/or when A is absent, each Y' is independently bonded to R° or X-L-Z, as defined above.

In accordance with another embodiment, the carbene monolayer comprises one or more carbenes of formula Ia

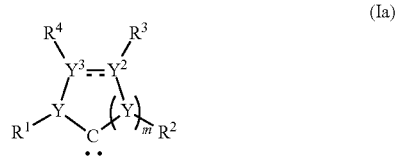

(Ia)

wherein:

m is an integer from 0 to 4;

each Y is independently C or a heteroatom;

$Y^2$ and $Y^3$ are independently C or a heteroatom, and the dashed line represents an optional double bond;

$R^1$ and $R^2$ are independently absent, at least one lone pair of electrons, H, $C_1$-$C_{10}$ alkyl, $C_{10}$-$C_{20}$ alkyl, $C_1$-$C_{10}$ alkenyl, $C_{10}$-$C_{20}$ alkenyl, $C_1$-$C_{10}$ alkynyl, $C_{10}$-$C_{20}$ alkynyl, $C_3$-$C_{20}$ cyclic aliphatic moiety, aryl, heteroaryl, ether, thiol, thioether, amine, polyamine, polyether, polythioether, or polythiol, each of which may be optionally substituted;

$R^3$ and $R^4$ are independently H, halogen, the substituent X-L-Z as defined for Formula I, $C_1$-$C_{10}$ alkyl, $C_{10}$-$C_{20}$ alkyl, $C_1$-$C_{10}$ alkenyl, $C_{10}$-$C_{20}$ alkenyl, $C_1$-$C_{10}$ alkynyl, $C_{10}$-$C_{20}$ alkynyl, $C_3$-$C_{20}$ cyclic aliphatic moiety, $C_1$-$C_{10}$ alkoxyl, $C_{10}$-$C_{20}$ alkoxyl, $C_3$-$C_{20}$ cyclic aliphatic moiety, aryl, heteroaryl, ether, thioether, amine, polyamine, polyether, or polythioether, each of which is optionally substituted; or, any one of $R^3$ or $R^4$, with any one of $R^1$ or $R^2$, together with the atoms to which they are attached, are connected to form a cycle, or heterocycle, each of which is optionally substituted.

In accordance with another aspect, there is provided a method for forming a composite material comprising a carbene monolayer and a material having at least a metal surface, wherein the carbene monolayer interacts with the metal surface and is stable, uniform, and/or substantially free of contamination, said method comprising contacting a metal surface with at least one carbene or carbene precursor.

In accordance with one embodiment, contacting a metal surface with at least one carbene or carbene precursor comprises immersing said surface in carbenes or carbene precursors; or, thermally decomposing carbene precursors in the presence of said surface.

In accordance with one embodiment of this method, the carbenes are of formula I or formula Ia. In accordance with another embodiment, one of the carbene precursors is of formula II

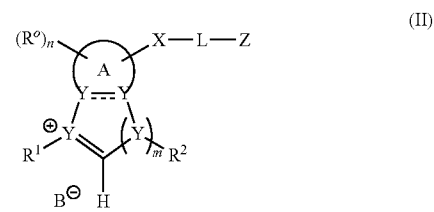

(II)

wherein:

n is an integer from 1 to 8, or from 1 to 4;

m is an integer from 0 to 4;

B is a counter ion that optionally acts as a base;

A is absent, an aliphatic cycle, a heterocycle, an aromatic ring, a fused aromatic ring system, a heteroaromatic ring, and/or a fused heteroaromatic ring system, each of which is optionally substituted;

X-L-Z is absent, or

X is C or a heteroatom,

L is a divalent moiety, such as $C_1$-$C_{10}$ alkylene, $C_{10}$-$C_{20}$ alkylene, $C_1$-$C_{10}$ alkenylene, $C_{10}$-$C_{20}$ alkenylene, $C_1$-$C_{10}$ alkynylene, $C_{10}$-$C_{20}$ alkynylene, or dextran, a simple sugar, complex sugar, carbohydrate, ether, thioether, amine, polyamine, polyether, and/or polythioether, each of which is optionally substituted;

Z is H, an aliphatic cycle, a heterocycle, an aromatic ring, a fused aromatic ring system, a heteroaromatic ring, a fused heteroaromatic ring system, an organometallic complex, a transition-metal catalyst, a metal-oxide catalyst, a simple sugar, a complex sugar, a carbohydrate, or a chemically derivatizable group, such as —OH, azide, carboxylic acid, carbonyl chloride, anhydride, ester, aldehyde, alcohol, amine, halogen, epoxide, thiirane, aziridine, amino acid, nucleic acid, alkene, alkyne, conjugated diene, thiol, or thioester, each of which is optionally substituted;

each Y or Y' is independently C or a heteroatom;

each R° is independently H, halogen, the substituent X-L-Z as defined above, $C_1$-$C_{10}$ alkyl, $C_{10}$-$C_{20}$ alkyl, $C_1$-$C_{10}$ alkenyl, $C_1$-$C_{20}$ alkenyl, $C_1$-$C_{10}$ alkynyl, $C_{10}$-$C_{20}$ alkynyl, $C_1$-$C_{10}$ alkoxyl, $C_{10}$-$C_{20}$ alkoxyl, $C_3$-$C_{20}$ cyclic aliphatic moiety, aryl, heteroaryl, ether, thioether, amine, polyamine, polyether, or polythioether, each of which is optionally substituted; or, two of R°, together with the atoms to which they are attached, are connected to form a cycle, or heterocycle, each of which is optionally substituted; and $R^1$ and $R^2$ are independently absent, at least one lone pair of electrons, H, $C_1$-$C_{10}$ alkyl, $C_{10}$-$C_{20}$ alkyl, $C_1$-$C_{10}$ alkenyl, $C_{10}$-$C_{20}$ alkenyl, $C_1$-$C_{10}$ alkynyl, $C_{10}$-$C_{20}$ alkynyl, $C_3$-$C_{20}$ cyclic aliphatic moiety, aryl, heteroaryl, ether, thiol, thioether, amine, polyamine, polyether, polythioether, or polythiol, each of which is optionally substituted; or, one of R¹ or R², with one of R°, together with the atoms to which they are attached, are connected to form a cycle, or heterocycle, each of which is optionally substituted;

wherein, when A is absent or non-aromatic, the dashed line represents an optional double bond; and/or when A is absent, each Y' is independently bonded to R° or X-L-Z, as defined above.

In accordance with an another embodiment of this method, the carbene precursor is of formula IIa

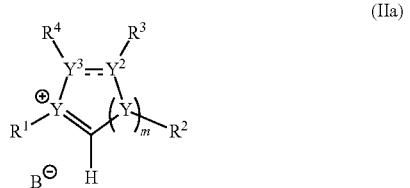

(IIa)

wherein:
  m is an integer from 0 to 4;
  B is a counter ion that optionally acts as a base;
  each Y is independently C or a heteroatom;
  $Y^2$ and $Y^3$ are independently C or a heteroatom, and the dashed line is an optional double bond;
  $R^1$ and $R^2$ are independently absent, at least one lone pair of electrons, H, $C_1$-$C_{10}$ alkyl, $C_{10}$-$C_{20}$ alkyl, $C_1$-$C_{10}$ alkenyl, $C_{10}$-$C_{20}$ alkenyl, $C_1$-$C_{10}$ alkynyl, $C_{10}$-$C_{20}$ alkynyl), cycloalkyl, aryl, heteroaryl, ether, thiol, thioether, amine, polyamine, polyether, polythioether, or polythiol, each of which is optionally substituted;
  $R^3$ and $R^4$ are independently H, halogen, the substituent X-L-Z as defined for Formula II, $C_1$-$C_{10}$ alkyl, $C_{10}$-$C_{20}$ alkyl, $C_1$-$C_{10}$ alkenyl, $C_{10}$-$C_{20}$ alkenyl, $C_1$-$C_{10}$ alkynyl, $C_{10}$-$C_{20}$ alkynyl, $C_1$-$C_{10}$ alkoxyl, $C_{10}$-$C_{20}$ alkoxyl, $C_3$-$C_{20}$ cyclic aliphatic, aryl, heteroaryl, ether, thioether, amine, polyamine, polyether, or polythioether, each of which is optionally substituted; or, any one of $R^3$ or $R^4$, with any one of $R^1$ or $R^2$, together with the atoms to which they are attached, are connected to form a cycle, or heterocycle, each of which is optionally substituted.

In accordance with an alternative embodiment of this method, the carbene precursor is of formula III

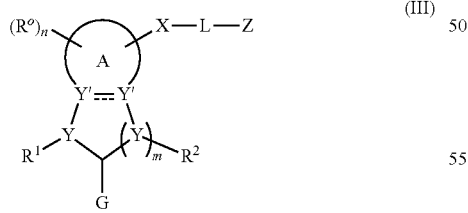

(III)

wherein:
  n is an integer from 1 to 4, or alternatively 1 to 8;
  m is an integer from 0 to 4;
  G is a perhalogenated alkyl, perhalogenated alkenyl, perhalogenated alkynyl, a perhalogenated aryl, or OR', wherein R' is an aliphatic group, for example, an alkyl group.
  A is absent, an aliphatic cycle, a heterocycle, an aromatic ring, a fused aromatic ring system, a heteroaromatic ring, and/or a fused heteroaromatic ring system, each of which is optionally substituted;
  X-L-Z is absent, or
  X is C or a heteroatom,
  L is a divalent moiety, such as $C_1$-$C_{10}$ alkylene, $C_{10}$-$C_{20}$ alkylene, $C_1$-$C_{10}$ alkenylene, $C_{10}$-$C_{20}$ alkenylene, $C_1$-$C_{10}$ alkynylene, $C_{10}$-$C_{20}$ alkynylene, or dextran, a simple sugar, complex sugar, carbohydrate, ether, thioether, amine, polyamine, polyether, and/or polythioether, each of which is optionally substituted;
  Z is H, an aliphatic cycle, a heterocycle, an aromatic ring, a fused aromatic ring system, a heteroaromatic ring, a fused heteroaromatic ring system, an organometallic complex, a transition-metal catalyst, a metal-oxide catalyst, a simple sugar, a complex sugar, a carbohydrate, or a chemically derivatizable group, such as —OH, azide, carboxylic acid, carbonyl chloride, anhydride, ester, aldehyde, alcohol, amine, halogen, epoxide, thiirane, aziridine, amino acid, nucleic acid, alkene, alkyne, conjugated diene, thiol, alkyl thiol, or thioester, each of which is optionally substituted;
  each Y or Y' is independently C or a heteroatom;
  each R° is independently H, halogen, the substituent X-L-Z as defined above, $C_1$-$C_{10}$ alkyl, $C_{10}$-$C_{20}$ alkyl, $C_1$-$C_{10}$ alkenyl, $C_{10}$-$C_{20}$ alkenyl, $C_1$-$C_{10}$ alkynyl, or $C_{10}$-$C_{20}$ alkynyl, $C_1$-$C_{10}$ alkoxyl, $C_{10}$-$C_{20}$ alkoxyl, $C_3$-$C_{20}$ cyclic aliphatic moiety, aryl, heteroaryl, ether, thioether, amine, polyamine, polyether, or polythioether, each of which is optionally substituted; or, two of R°, together with the atoms to which they are attached, are connected to form a cycle, or heterocycle, each of which is optionally substituted; and
  $R^1$ and $R^2$ are independently absent, at least one lone pair of electrons, H, $C_1$-$C_{10}$ alkyl, $C_{10}$-$C_{20}$ alkyl, branched $C_1$-$C_{10}$ alkyl, $C_{10}$-$C_{20}$ alkenyl, $C_1$-$C_{10}$ alkynyl, or $C_{10}$-$C_{20}$ alkynyl), $C_3$-$C_{20}$ cyclic aliphatic moiety, aryl, heteroaryl, ether, thiol, thioether, amine, polyamine, polyether, polythioether, or polythiol, each of which is optionally substituted; or, one of $R^1$ or $R^2$, with one of R°, together with the atoms to which they are attached, are connected to form a cycle, or heterocycle, each of which is optionally substituted;
  wherein, when A is absent or non-aromatic, the dashed line represents an optional double bond; and/or
  when A is absent, each Y' is independently bonded to R° or X-L-Z, as defined above.

In accordance with an another embodiment of this method, the carbene precursor is of formula IIIa

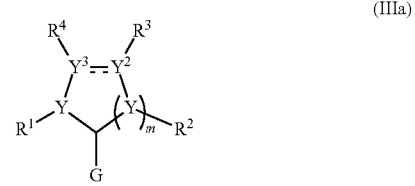

(IIIa)

wherein:
  m is an integer from 0 to 4;
  G is a perhalogenated alkyl, perhalogenated alkenyl, perhalogenated alkynyl, a perhalogenated aryl, or OR', wherein R' is an aliphatic group, for example, an alkyl group.

each Y or Y' is independently C or a heteroatom;

$Y^2$ and $Y^3$ are independently C or a heteroatom, and the dashed line represents an optional double bond;

$R^1$ and $R^2$ are independently absent, at least one lone pair of electrons, H, $C_1$-$C_{10}$ alkyl, $C_{10}$-$C_{20}$ alkyl, $C_1$-$C_{10}$ alkenyl, $C_{10}$-$C_{20}$ alkenyl, $C_1$-$C_{10}$ alkynyl, $C_{10}$-$C_{20}$ alkynyl, cycloalkyl, aryl, heteroaryl, ether, thiol, thioether, amine, polyamine, polyether, polythioether, or polythiol, each of which may be optionally substituted;

$R^3$ and $R^4$ are independently H, halogen, the substituent X-L-Z as defined for Formula III, $C_1$-$C_{10}$ alkyl, $C_{10}$-$C_{20}$ alkyl, branched $C_1$-$C_{10}$ alkyl, branched $C_{10}$-$C_{20}$ alkyl, $C_1$-$C_{10}$ alkenyl, $C_{10}$-$C_{20}$ alkenyl, $C_1$-$C_{10}$ alkynyl, $C_{10}$-$C_{20}$ alkynyl, $C_1$-$C_{10}$ alkoxyl, $C_{10}$-$C_{20}$ alkoxyl, $C_3$-$C_{20}$ cyclic aliphatic, aryl, heteroaryl, ether, thioether, amine, polyamine, polyether, or polythioether, each of which is optionally substituted; or, any one of $R^3$ or $R^4$, with any one of $R^1$ or $R^2$, together with the atoms to which they are attached, are connected to form a cycle, or heterocycle, each of which is optionally substituted.

In accordance with another aspect, there is provided a method for forming a composite material comprising a carbene monolayer and a material having at least a metal surface, wherein the carbene monolayer interacts with the metal surface and is stable, uniform, and/or substantially free of contamination, said method comprising vapour depositing a carbene or carbene precursor on a metal surface.

In accordance with another aspect, there is provided a method for removing a carbene-monolayer from a composite material, wherein said composite material comprises said carbene monolayer and a material having at least a metal surface, wherein the carbene monolayer interacts with the metal surface and is stable, uniform, and/or substantially free of contamination, said method comprising exposing the composite material to a >1% $H_2O_2$ solution for at least 24 h; or exposing the composite material to temperatures ≥190° C. in a suitable solvent. In one embodiment, the suitable solvent is decalin.

In accordance with another aspect of the application, there is provided a use of the herein described carbene-functionalized composite materials for modifying a metal surface.

In accordance with another aspect, there is provided a carbene-functionalized composite material comprising, a lipid layer, a hydrophobic carbene monolayer that is uniform, stable, and/or substantially free of contamination; and a material having at least one metal surface, wherein said hydrophobic carbene monolayer interacts with the metal surface, and said hydrophobic carbene monolayer is between the lipid layer and the metal surface. In accordance with one embodiment, the material is a metal chip and the composite material forms at least part of an analytical instrument. In another embodiment, the metal chip comprises a metal film and all connections necessary for incorporation into an analytical instrument as a detector.

In accordance with another embodiment, the carbene monolayer comprises one or more carbenes of formula IV

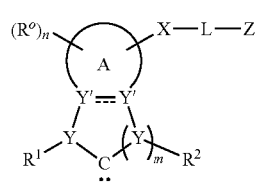

(IV)

wherein:

n is an integer from 1 to 8, or from 1 to 4;

m is an integer from 0 to 4;

A is absent, an aliphatic cycle, a heterocycle, an aromatic ring, a fused aromatic ring system, a heteroaromatic ring, and/or a fused heteroaromatic ring system, each of which is optionally substituted;

X-L-Z is absent, or

X is C or a heteroatom,

L is a divalent moiety, such as $C_{10}$-$C_{20}$ alkylene, $C_{10}$-$C_{20}$ alkenylene, $C_{10}$-$C_{20}$ alkynylene, dextran, a simple sugar, complex sugar, carbohydrate, ether, thioether, polyether, and/or polythioether, each of which is optionally substituted;

Z is H or L, as defined above;

each Y or Y' is independently C or a heteroatom;

each R° is independently H, halogen, the substituent X-L-Z as defined above, $C_{10}$-$C_{20}$ alkyl, $C_{10}$-$C_{20}$ alkenyl, $C_{10}$-$C_{20}$ alkynyl, $C_{10}$-$C_{20}$ alkoxyl, $C_6$-$C_{20}$ cyclic aliphatic moiety, aryl, ether, thioether, polyether, or polythioether, each of which is optionally substituted; or, two of R°, together with the atoms to which they are attached, are connected to form a cycle, which is optionally substituted; and $R^1$ and $R^2$ are independently absent, at least one lone pair of electrons, H, $C_{10}$-$C_{20}$ alkyl, $C_{10}$-$C_{20}$ alkenyl, $C_{10}$-$C_{20}$ alkynyl, $C_6$-$C_{20}$ cyclic aliphatic moiety, aryl, ether, thiol, thioether, polyether, polythioether, or polythiol, each of which is optionally substituted; or, one of $R^1$ or $R^2$, with one of R°, together with the atoms to which they are attached, are connected to form a cycle, which is optionally substituted;

wherein, when A is absent or non-aromatic, the dashed line represents an optional double bond; and/or when A is absent, each Y' is independently bonded to R° or X-L-Z, as defined above.

In accordance with another embodiment, the carbene monolayer comprises one or more carbenes of formula IVa

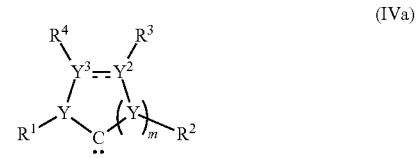

(IVa)

wherein:

m is an integer from 0 to 4;

each Y is independently C or a heteroatom;

$Y^2$ and $Y^3$ are independently C or a heteroatom, and the dashed line represents an optional double bond;

$R^1$ and $R^2$ are independently absent, at least one lone pair of electrons, H, $C_{10}$-$C_{20}$ alkyl, $C_{10}$-$C_{20}$ alkenyl, $C_{10}$-$C_{20}$ alkynyl, $C_6$-$C_{20}$ cyclic aliphatic moiety, aryl, ether, thiol, thioether, polyether, polythioether, or polythiol, each of which may be optionally substituted;

$R^3$ and $R^4$ are independently H, the substituent X-L-Z as defined for Formula IV, $C_{10}$-$C_{20}$ alkyl, $C_{10}$-$C_{20}$ alkenyl, $C_{10}$-$C_{20}$ alkynyl, $C_6$-$C_{20}$ cyclic aliphatic moiety, $C_{10}$-$C_{20}$ alkoxyl, aryl, ether, thioether, polyether, or polythioether, each of which is optionally substituted; or, any one of $R^3$ or $R^4$, with any one of $R^1$ or $R^2$, together with the atoms to which they are attached, are connected to form a cycle, which is optionally substituted.

In accordance with another aspect, there is provided a method for forming a carbene-functionalized composite material comprising, a lipid layer, a hydrophobic carbene monolayer that is uniform, stable, and/or substantially free of contamination; and a material having at least one metal surface, wherein said hydrophobic carbene monolayer interacts with the metal surface, and said hydrophobic carbene monolayer is between the lipid layer and the metal surface, said method comprising contacting the material with a carbene or carbene precursor; and exposing the carbene-coated material to lipid vesicles.

In one embodiment on this method, the carbene is of formula IV and IVa. In another embodiment of this method, the carbene precursor is of formula V

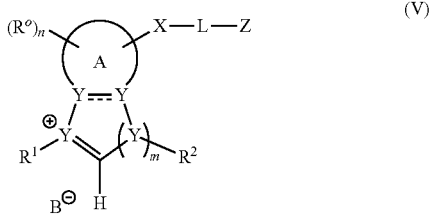

(V)

wherein:
n is an integer from 1 to 8, or from 1 to 4;
m is an integer from 0 to 4;
B is a counter ion that optionally acts as a base;
A is absent, an aliphatic cycle, a heterocycle, an aromatic ring, a fused aromatic ring system, a heteroaromatic ring, and/or a fused heteroaromatic ring system, each of which is optionally substituted;
X-L-Z is absent, or
X is C or a heteroatom,
L is a divalent moiety, such as $C_{10}$-$C_{20}$ alkylene, $C_{10}$-$C_{20}$ alkenylene, $C_{10}$-$C_{20}$ alkynylene, dextran, a simple sugar, complex sugar, carbohydrate, ether, thioether, polyether, and/or polythioether, each of which is optionally substituted;
Z is H or L, as defined above;
each Y or Y' is independently C or a heteroatom;
each R° is independently H, halogen, the substituent X-L-Z as defined above, $C_{10}$-$C_{20}$ alkyl, $C_{10}$-$C_{20}$ alkenyl, $C_{10}$-$C_{20}$ alkynyl, $C_{10}$-$C_{20}$ alkoxyl, $C_6$-$C_{20}$ cyclic aliphatic moiety, aryl, ether, thioether, polyether, or polythioether, each of which is optionally substituted; or, two of R°, together with the atoms to which they are attached, are connected to form a cycle, which is optionally substituted; and
$R^1$ and $R^2$ are independently absent, at least one lone pair of electrons, H, $C_{10}$-$C_{20}$ alkyl, $C_{10}$-$C_{20}$ alkenyl, $C_{10}$-$C_{20}$ alkynyl, $C_6$-$C_{20}$ cyclic aliphatic moiety, aryl, ether, thiol, thioether, polyether, polythioether, or polythiol, each of which is optionally substituted; or, one of $R^1$ or $R^2$, with one of R°, together with the atoms to which they are attached, are connected to form a cycle, which is optionally substituted;
wherein, when A is absent or non-aromatic, the dashed line represents an optional double bond; and/or
when A is absent, each Y' is independently bonded to R° or X-L-Z, as defined above.

In accordance with another embodiment, the carbene precursor is of formula Va

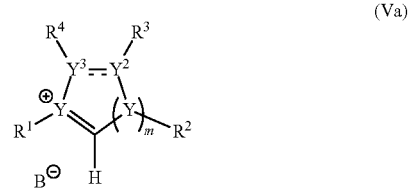

(Va)

wherein:
m is an integer from 0 to 4;
B is a counter ion that optionally acts as a base;
each Y is independently C or a heteroatom;
$Y^2$ and $Y^3$ are independently C or a heteroatom, and the dashed line is an optional double bond;
$R^1$ and $R^2$ are independently absent, at least one lone pair of electrons, H, $C_{10}$-$C_{20}$ alkyl, $C_{10}$-$C_{20}$ alkenyl, $C_{10}$-$C_{20}$ alkynyl, $C_6$-$C_{20}$ cyclic aliphatic moiety, aryl, ether, thiol, thioether, polyether, polythioether, or polythiol, each of which may be optionally substituted;
$R^3$ and $R^4$ are independently H, the substituent X-L-Z as defined for Formula V, $C_{10}$-$C_{20}$ alkyl, $C_{10}$-$C_{20}$ alkenyl, $C_{10}$-$C_{20}$ alkynyl, $C_6$-$C_{20}$ cyclic aliphatic moiety, $C_{10}$-$C_{20}$ alkoxyl, aryl, ether, thioether, polyether, or polythioether, each of which is optionally substituted; or, any one of $R^3$ or $R^4$, with any one of $R^1$ or $R^2$, together with the atoms to which they are attached, are connected to form a cycle, which is optionally substituted.

In accordance with an alternative embodiment of this method, the carbene precursor is of formula VI

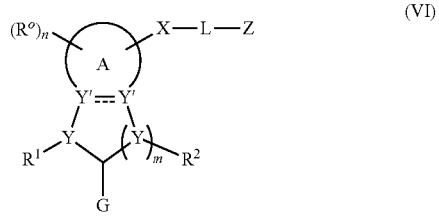

(VI)

wherein:
n is an integer from 1 to 4, or alternatively 1 to 8;
m is an integer from 0 to 4;
G is a perhalogenated alkyl, perhalogenated alkenyl, perhalogenated alkynyl, a perhalogenated aryl, or OR', wherein R' is an aliphatic group, for example, an alkyl group.
A is absent, an aliphatic cycle, a heterocycle, an aromatic ring, a fused aromatic ring system, a heteroaromatic ring, and/or a fused heteroaromatic ring system, each of which is optionally substituted;
X-L-Z is absent, or
X is C or a heteroatom,
L is a divalent moiety, such as $C_{10}$-$C_{20}$ alkylene, $C_{10}$-$C_{20}$ alkenylene, $C_{10}$-$C_{20}$ alkynylene, dextran, a simple sugar, complex sugar, carbohydrate, ether, thioether, polyether, and/or polythioether, each of which is optionally substituted;
Z is H or L, as defined above;
each Y or Y' is independently C or a heteroatom;
each R° is independently H, halogen, the substituent X-L-Z as defined above, $C_{10}$-$C_{20}$ alkyl, $C_{10}$-$C_{20}$ alkenyl, $C_{10}$-$C_{20}$ alkynyl, $C_{10}$-$C_{20}$ alkoxyl, $C_6$-$C_{20}$ cyclic aliphatic moiety, aryl, ether, thioether, polyether, or polythioether, each of which is optionally substituted; or, two of R°, together with the atoms to which they are attached, are connected to form a cycle, which is optionally substituted; and $R^1$ and $R^2$ are independently absent, at least one lone pair of electrons, H, $C_{10}$-$C_{20}$ alkyl, $C_{10}$-$C_{20}$ alkenyl, $C_{10}$-$C_{20}$ alkynyl, $C_6$-$C_{20}$ cyclic aliphatic moiety, aryl, ether, thiol, thioether, polyether, polythioether, or polythiol, each of which is optionally substituted; or, one of $R^1$ or $R^2$, with one of R°, together with the atoms to which they are attached, are connected to form a cycle, which is optionally substituted;

wherein, when A is absent or non-aromatic, the dashed line represents an optional double bond; and/or when A is absent, each Y' is independently bonded to R° or X-L-Z, as defined above.

In accordance with another alternative embodiment, the carbene precursor is of formula VIa

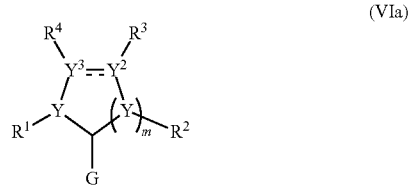

wherein:

m is an integer from 0 to 4;

G is a perhalogenated alkyl, perhalogenated alkenyl, perhalogenated alkynyl, a perhalogenated aryl, or OR', wherein R' is an aliphatic group, for example, an alkyl group.

each Y or Y' is independently C or a heteroatom;

$Y^2$ and $Y^3$ are independently C or a heteroatom, and the dashed line represents an optional double bond;

$R^1$ and $R^2$ are independently absent, at least one lone pair of electrons, H, $C_{10}$-$C_{20}$ alkyl, $C_{10}$-$C_{20}$ alkenyl, $C_{10}$-$C_{20}$ alkynyl, $C_6$-$C_{20}$ cyclic aliphatic moiety, aryl, ether, thiol, thioether, polyether, polythioether, or polythiol, each of which may be optionally substituted;

$R^3$ and $R^4$ are independently H, the substituent X-L-Z as defined for Formula VIa, $C_{10}$-$C_{20}$ alkyl, $C_{10}$-$C_{20}$ alkenyl, $C_{10}$-$C_{20}$ alkynyl, $C_6$-$C_{20}$ cyclic aliphatic moiety, $C_{10}$-$C_{20}$ alkoxyl, aryl, ether, thioether, polyether, or polythioether, each of which is optionally substituted; or, any one of $R^3$ or $R^4$, with any one of $R^1$ or $R^2$, together with the atoms to which they are attached, are connected to form a cycle, which is optionally substituted.

In accordance with another aspect, there is provided a use of the herein described carbene-functionalized composite materials in detecting and sensing applications. In one embodiment, the applications comprise detecting biomolecules.

BRIEF DESCRIPTION OF TABLES and FIGURES

For a better understanding of the present invention, as well as other aspects and further features thereof, reference is made to the following description which is to be used in conjunction with the accompanying tables and drawings, where:

Table 1 presents structural information on the herein described NHCs on metal;

Table 2A presents expected and found N:C ratios from C and N XPS spectra for carbene terminated gold (Au(111) and Au(NP) where the carbene monolayer is self-assembled from various NHCs. These data suggest a clean transfer of NHCs to surfaces was obtained for both Au(111) and Au nanoparticles;

Table 2B presents C and N XPS spectra for carbene terminated gold (Au (111)) where the carbene monolayer is self-assembled from carbonate salts of various NHCs. These data suggest a clean transfer of NHCs to surfaces;

Table 3 is shown in FIG. 23.

Table 4 presents characterization data of a representative NHC on Palladium (Pd) nanoparticles;

Table 5A presents a comparison loading of lecithin vesicles on a commercial HPA sensor chip and a representative NHC sensor chip. These data suggest that the NHC sensor chip offers improved performance as compared to the commercial sensor chip; and Table 5B presents a comparison of stability between an HPA sensor chip and a representative NHC sensor chip. These data suggest that the NHC sensor chip is stable under conditions that could destroy or damage a commercial sensor chip.

Figure 2A:
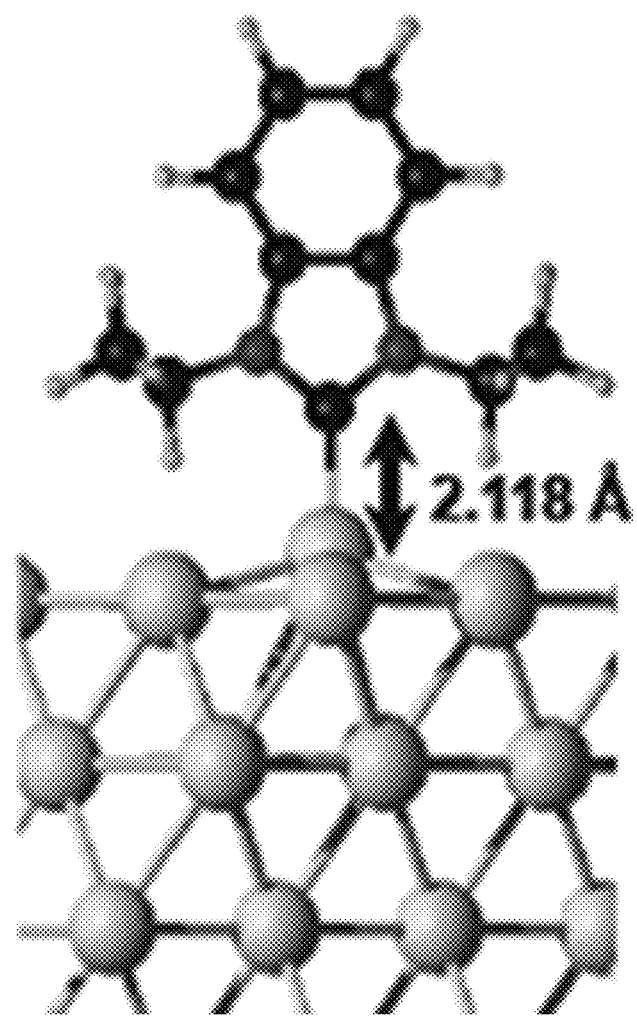
FIG. 2A depicts an STM image of NHC-1 on Au(111) that showed ordered self-assembly where rows of 5-10 oval shaped features were observed, consistent with the presence of stacked units of benzimidazole NHCs on the surface (dark regions represent one atom-deep erosion of the surface analogous to those seen with thiol-based monolayers)
Figure 2B:
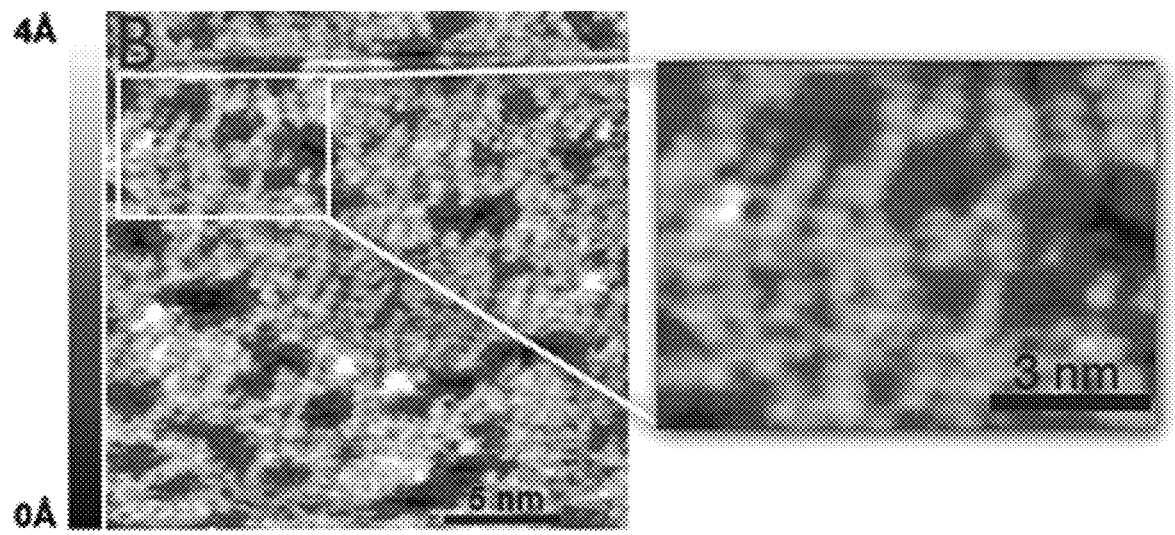
Figure 2C:
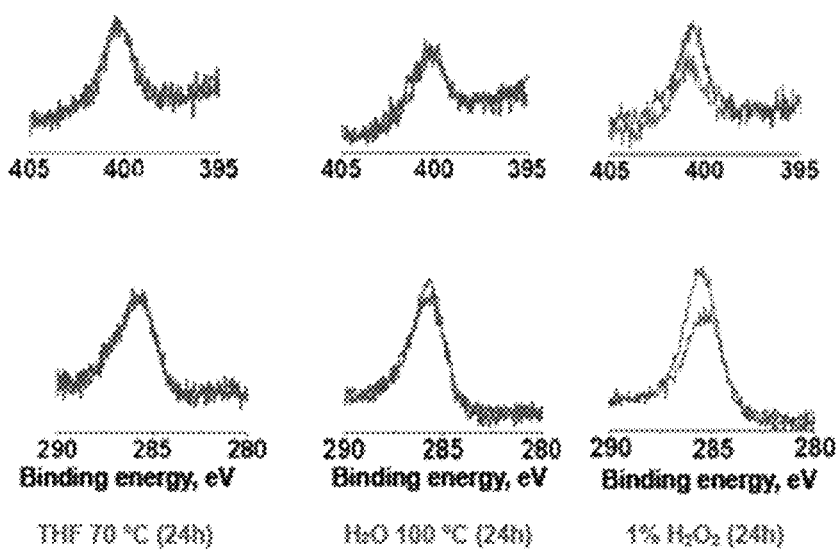
Figure 2D:
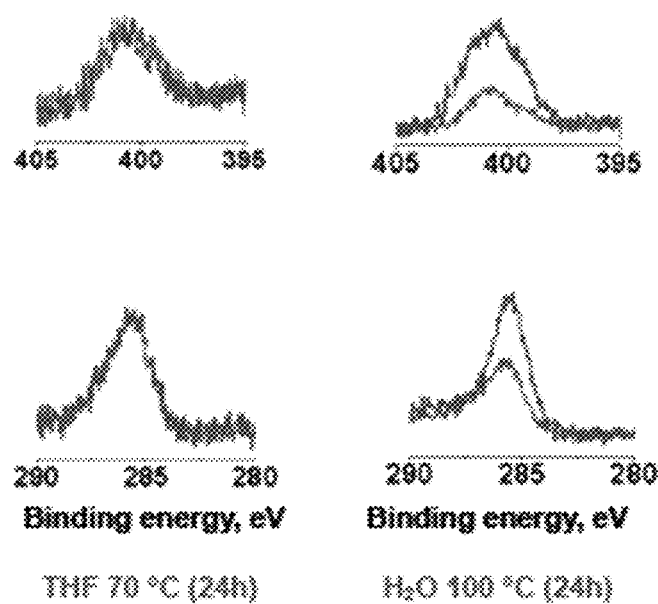
Figure 2E:
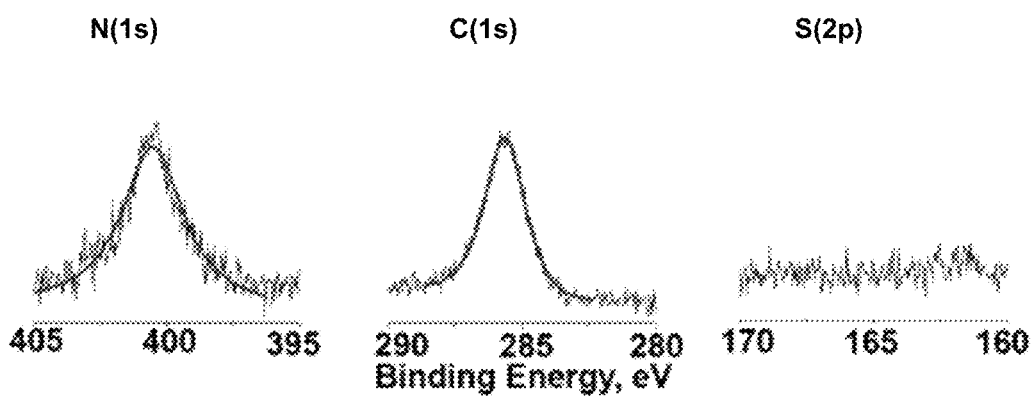
Figure 3D:
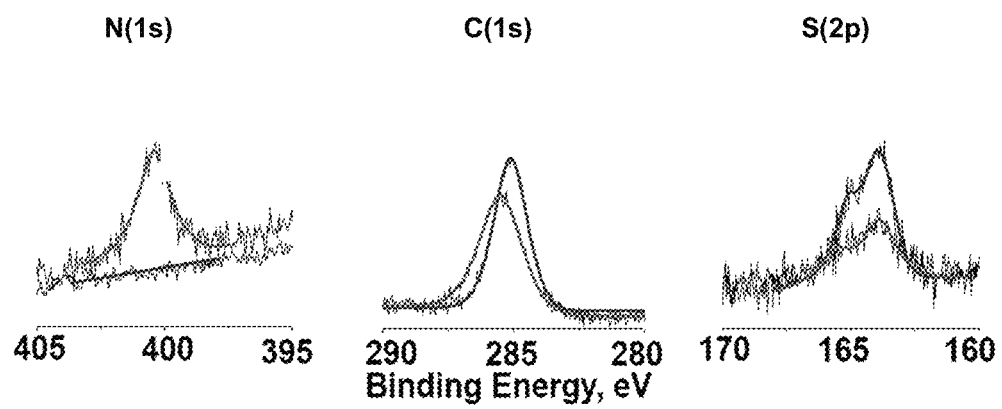
Figure 3E:
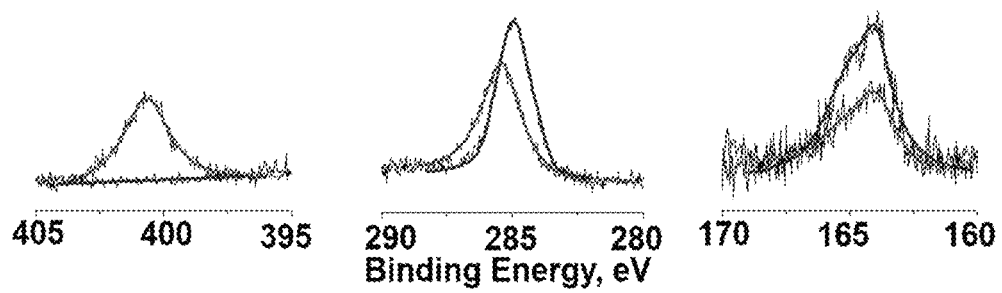
Figure 4:
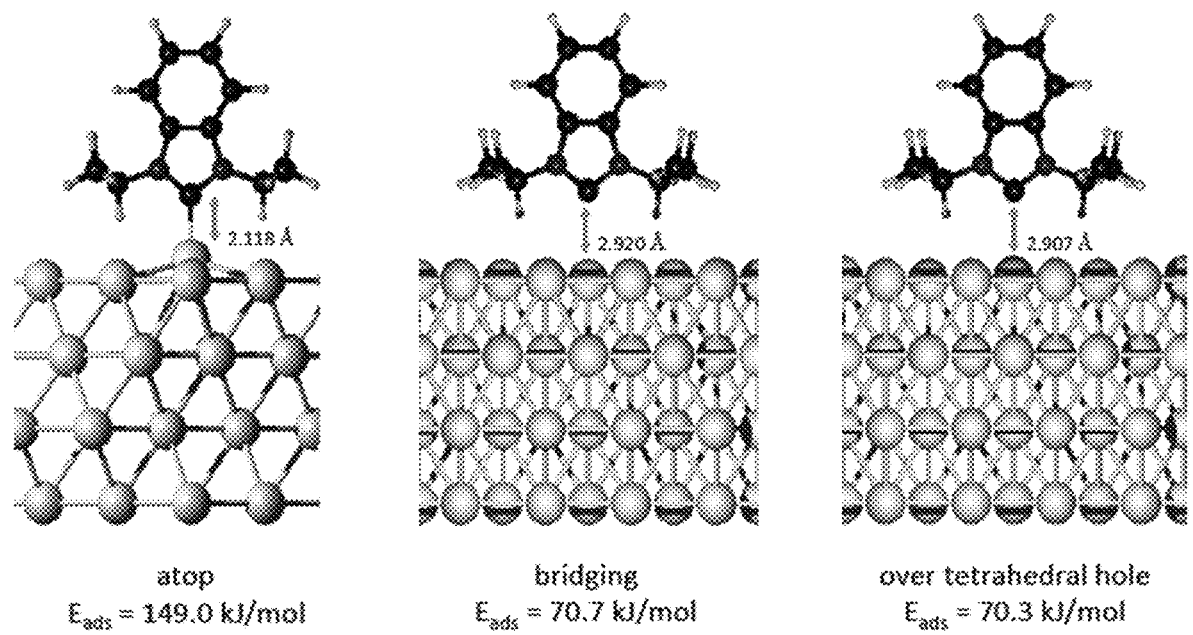
Figure 5:
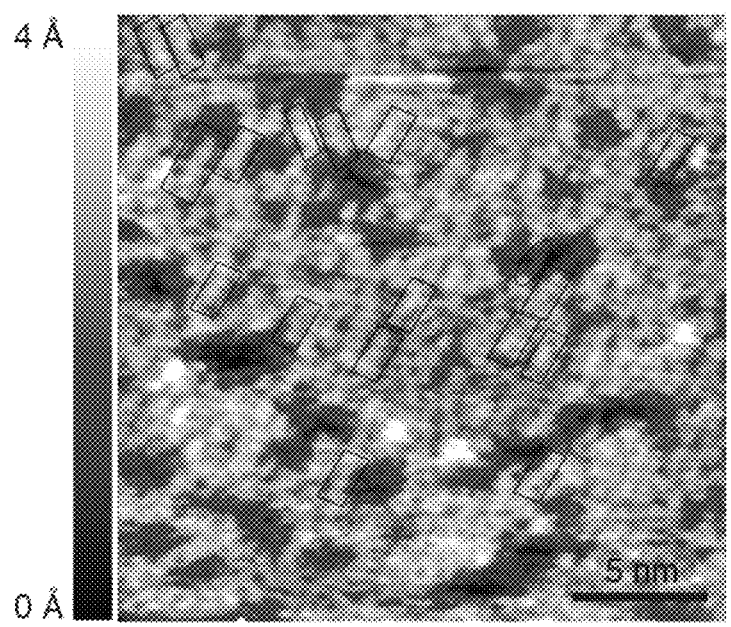
Figure 6:
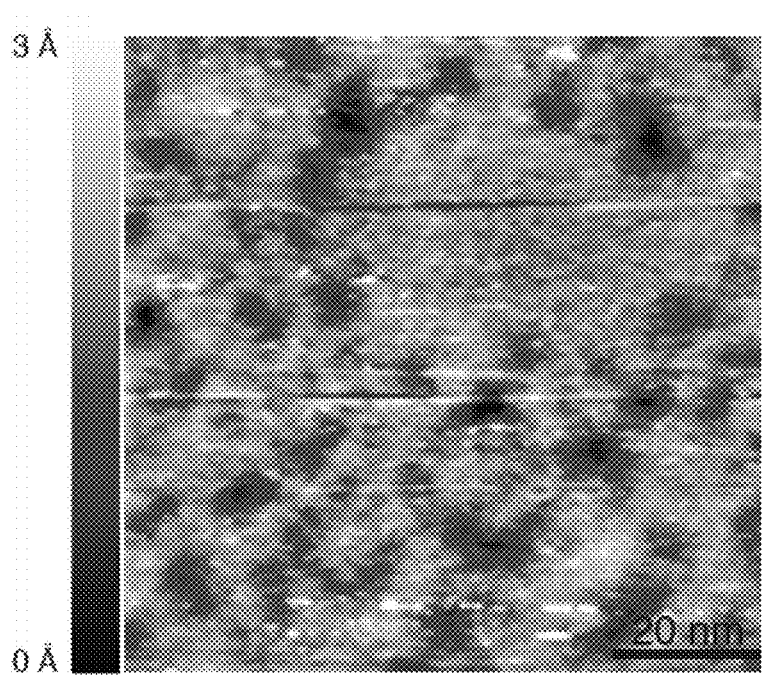
Figure 7A:
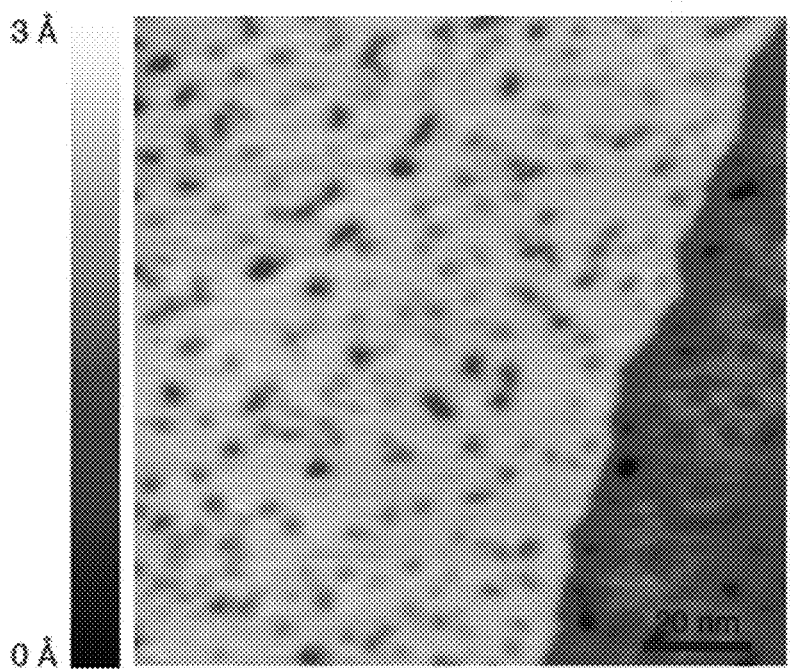
Figure 7B:
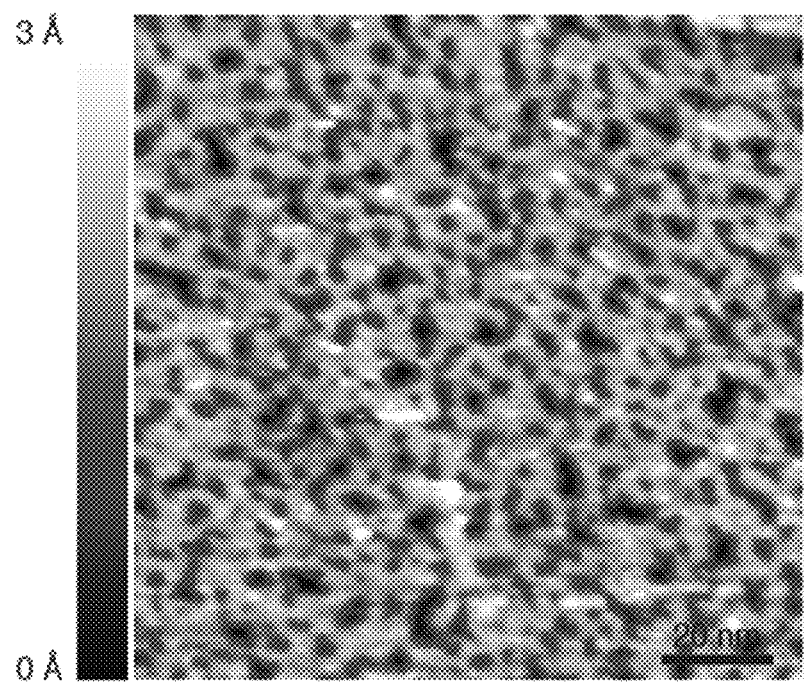
Figure 8:
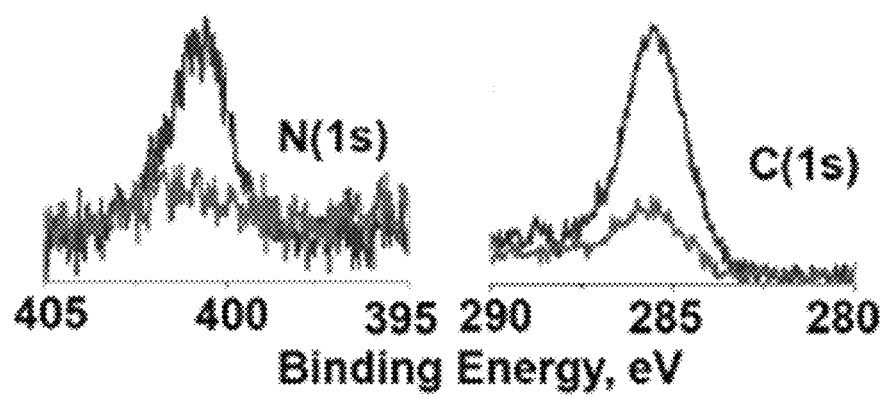
Figure 9:
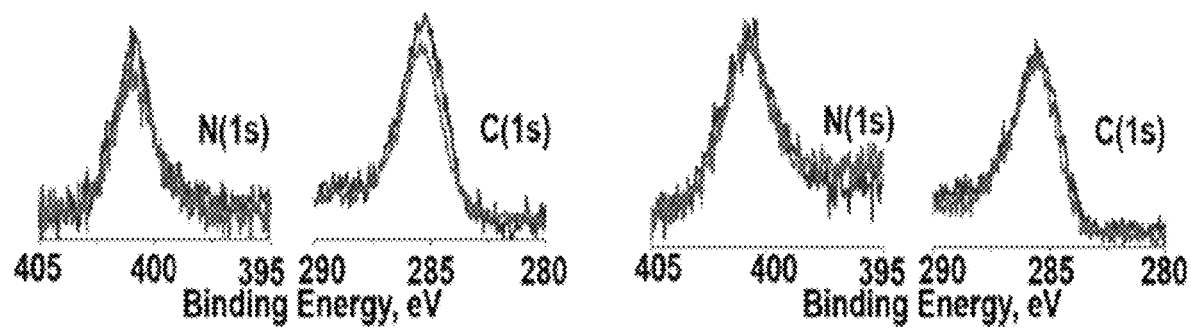
Figure 10:
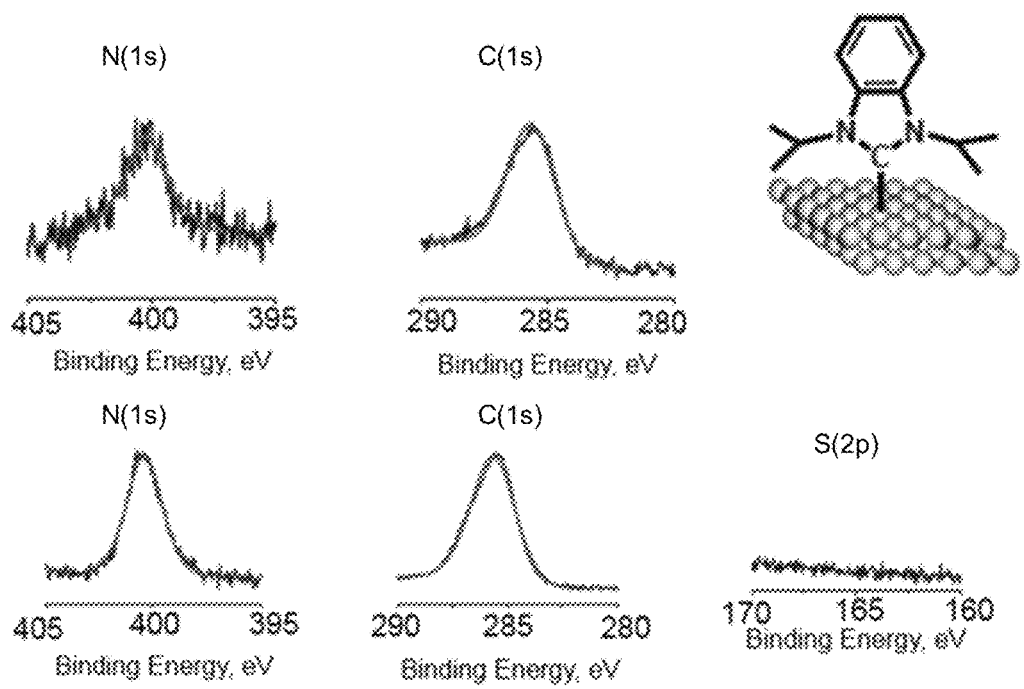
Figure 11:
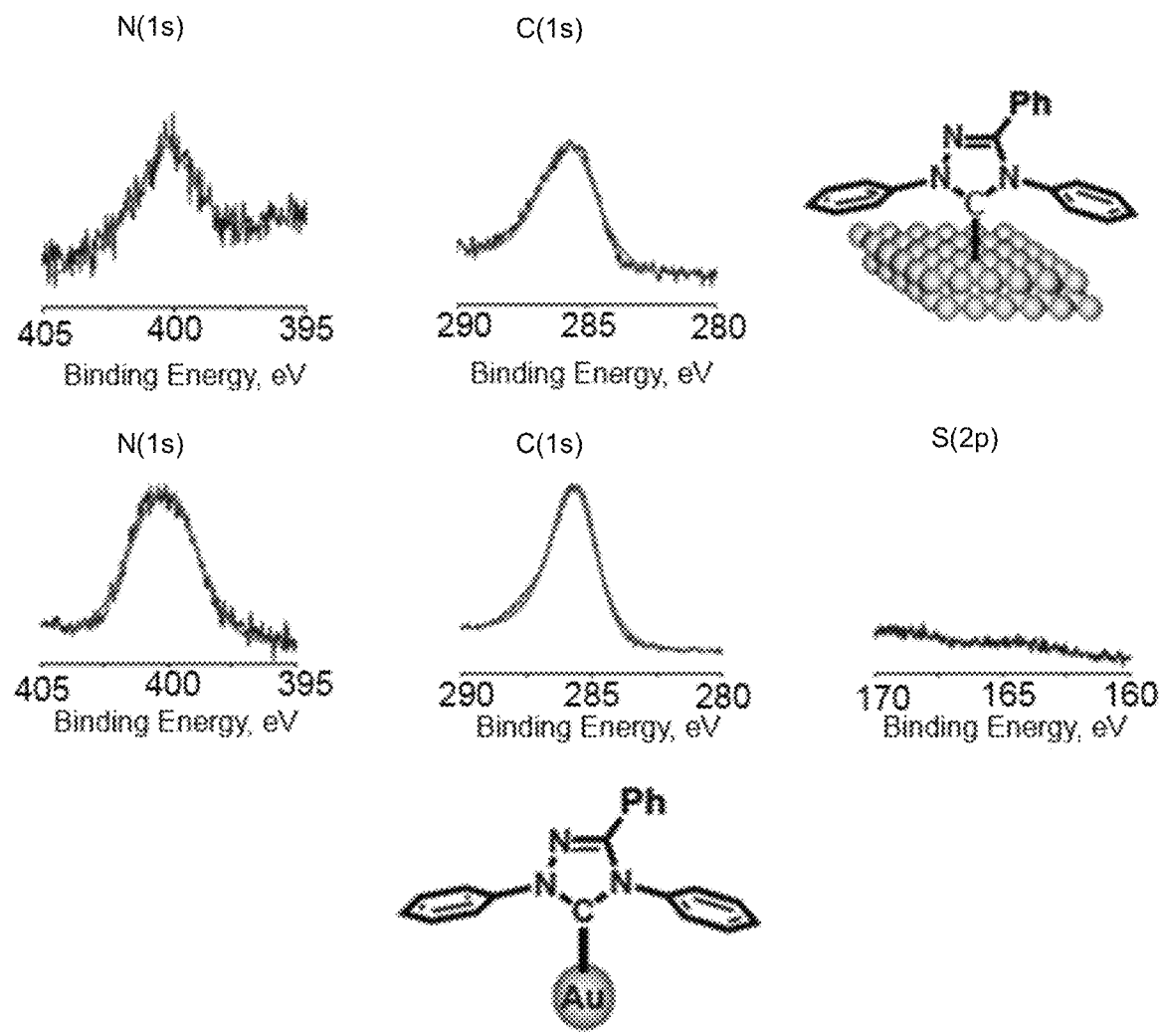
Figure 12:
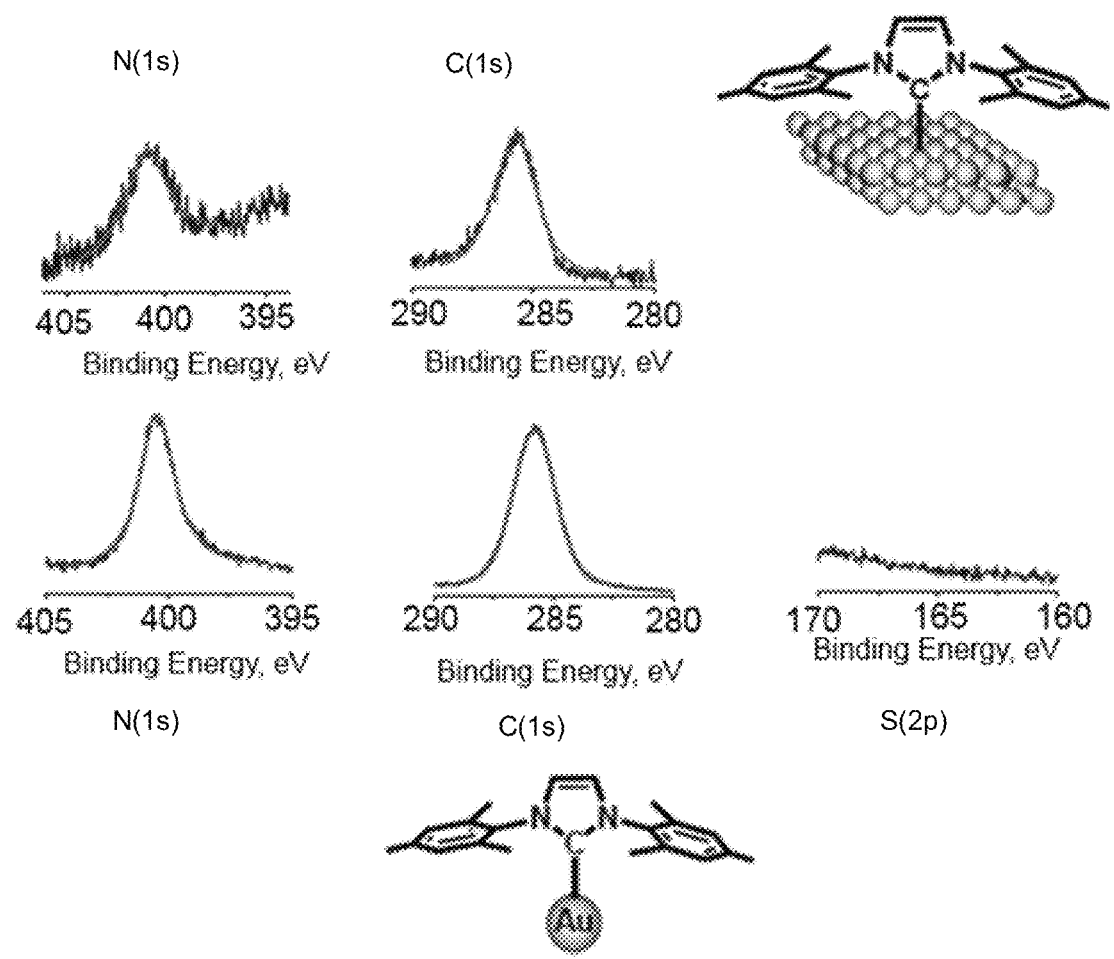
Figure 13:
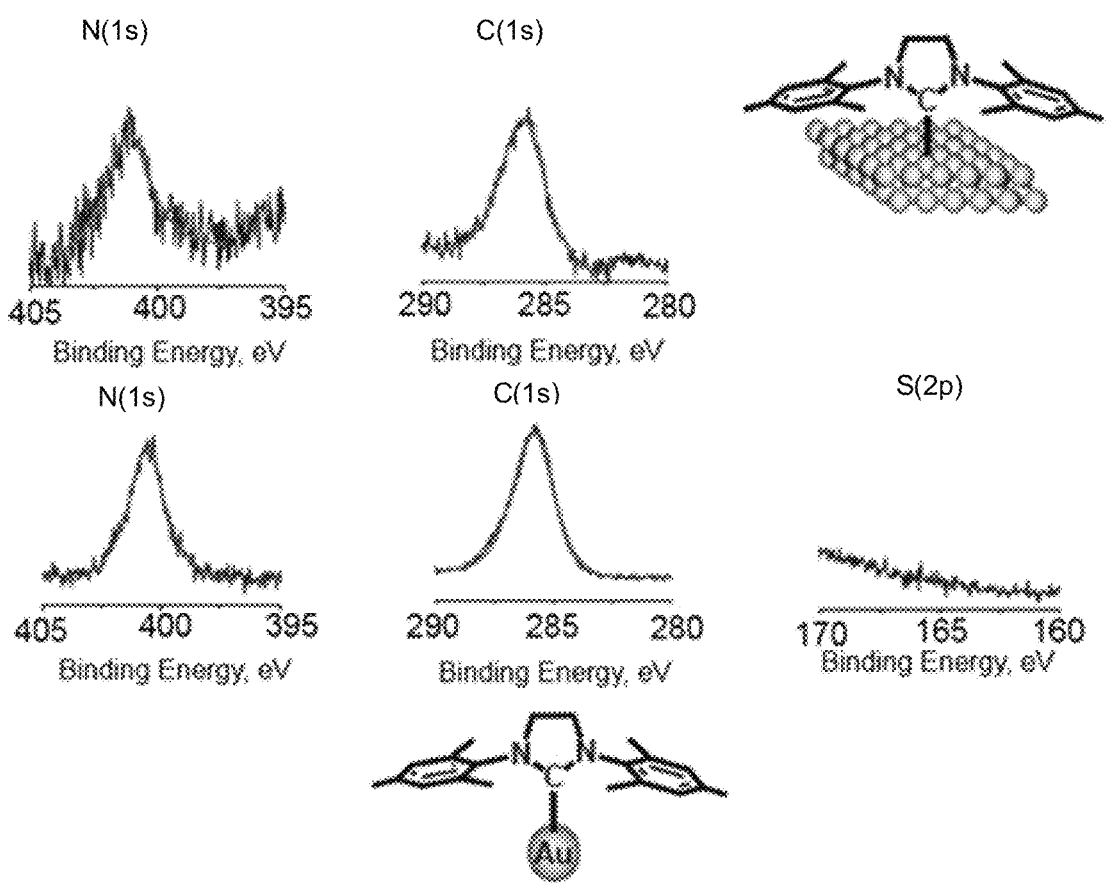
Figure 14:
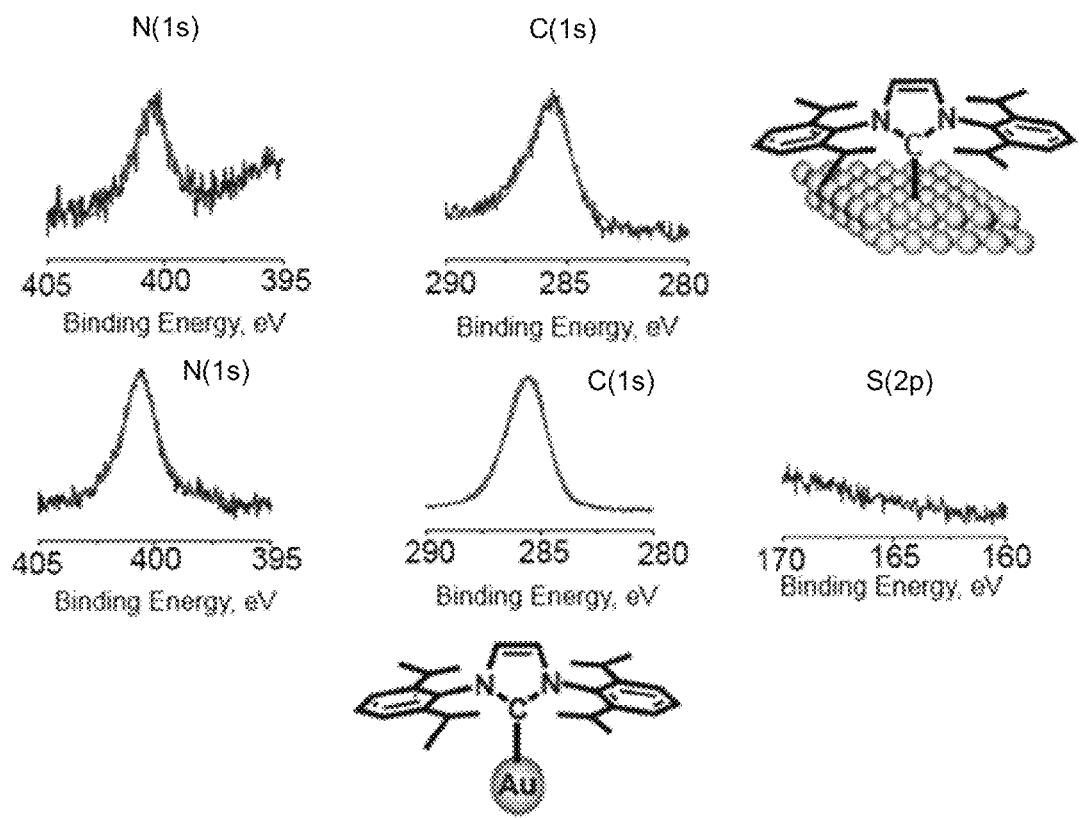
Figure 15:
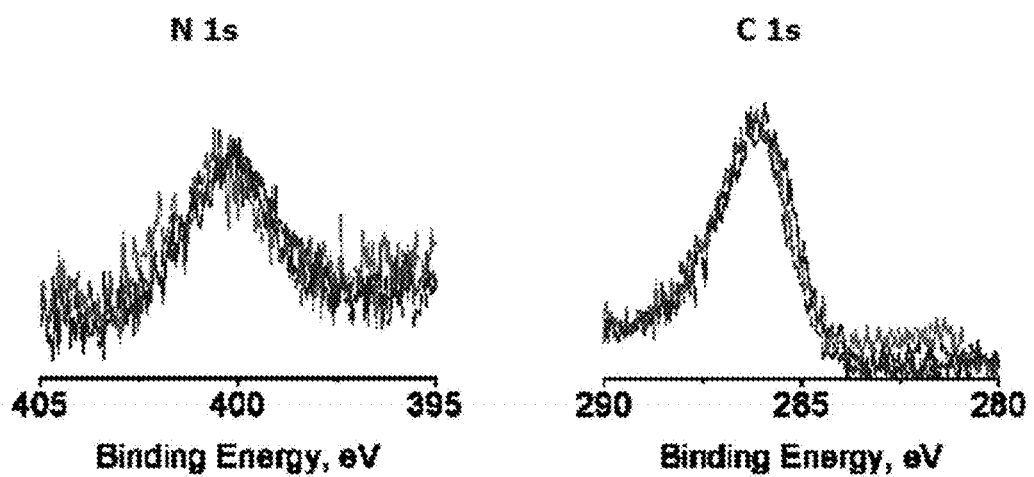
Figure 16A:
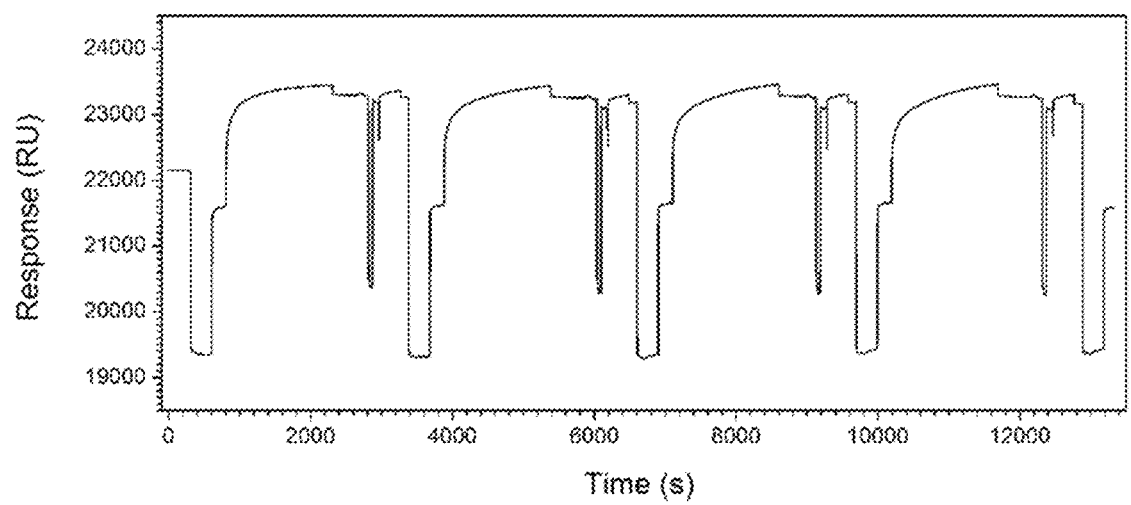
Figure 16B:
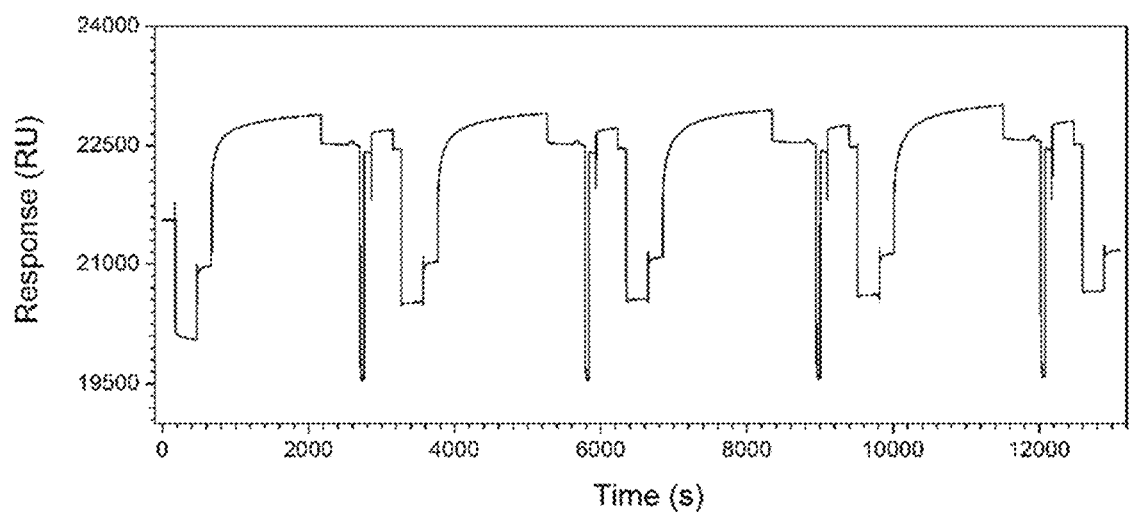
Figure 17A:
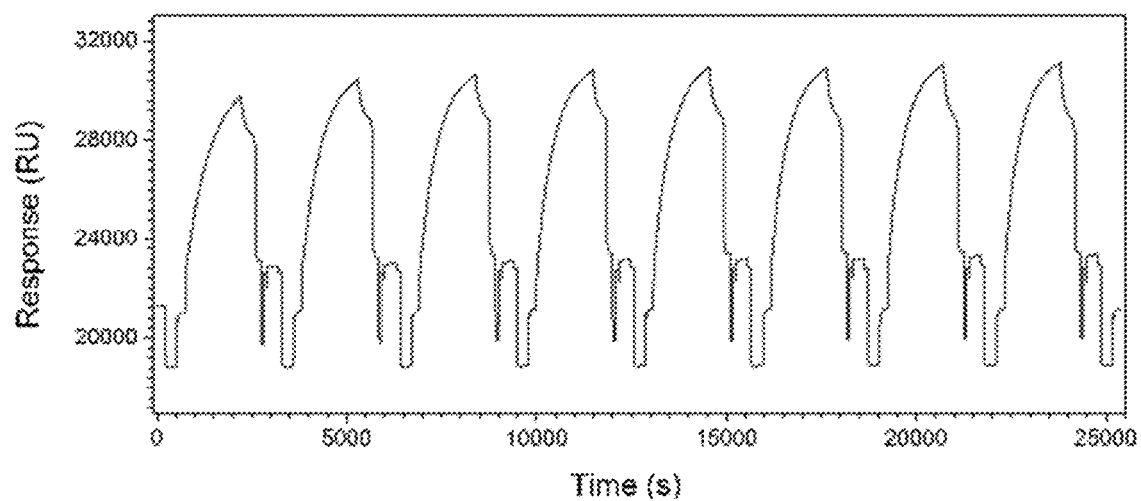
Figure 17B:
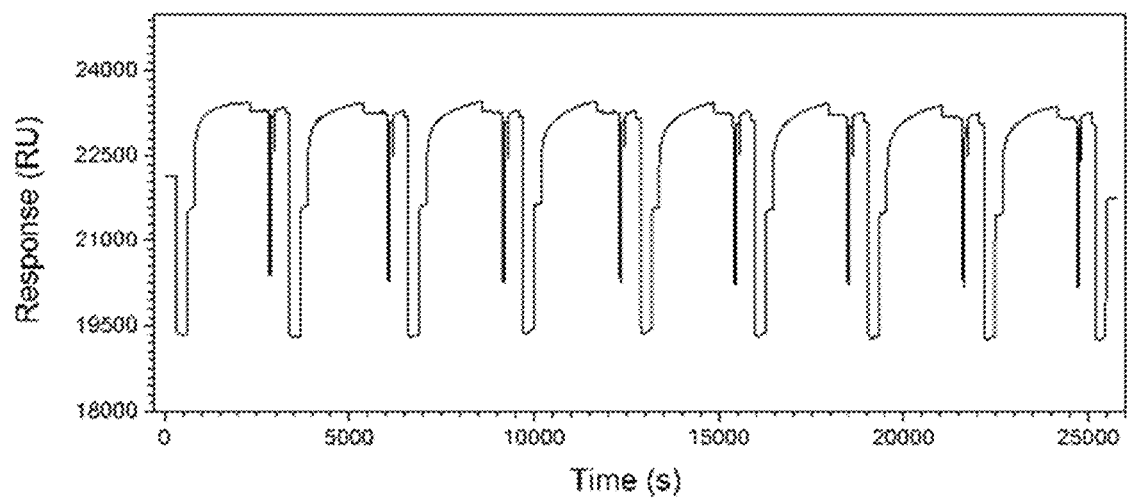
Figure 18A:
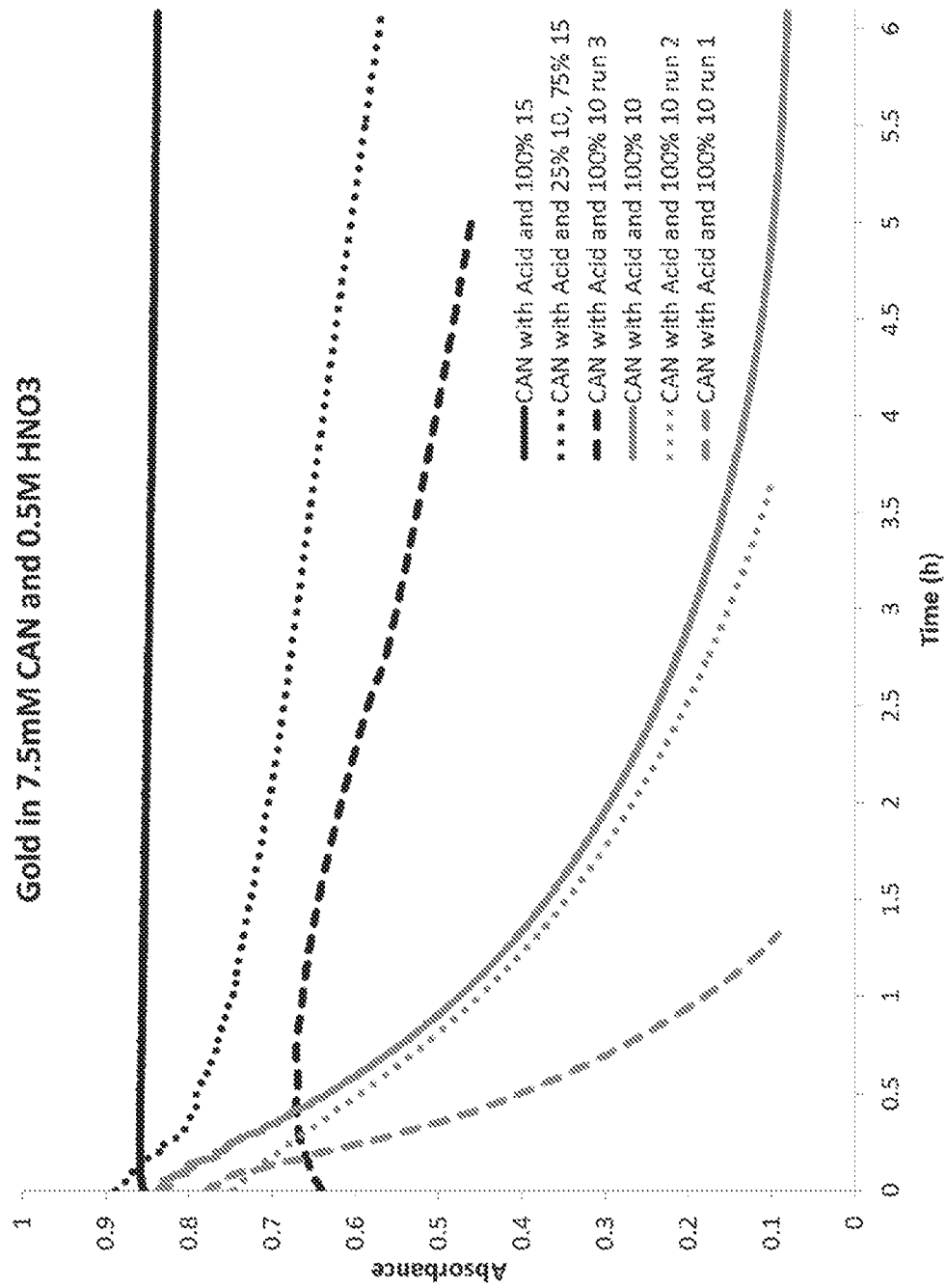
Figure 18B:
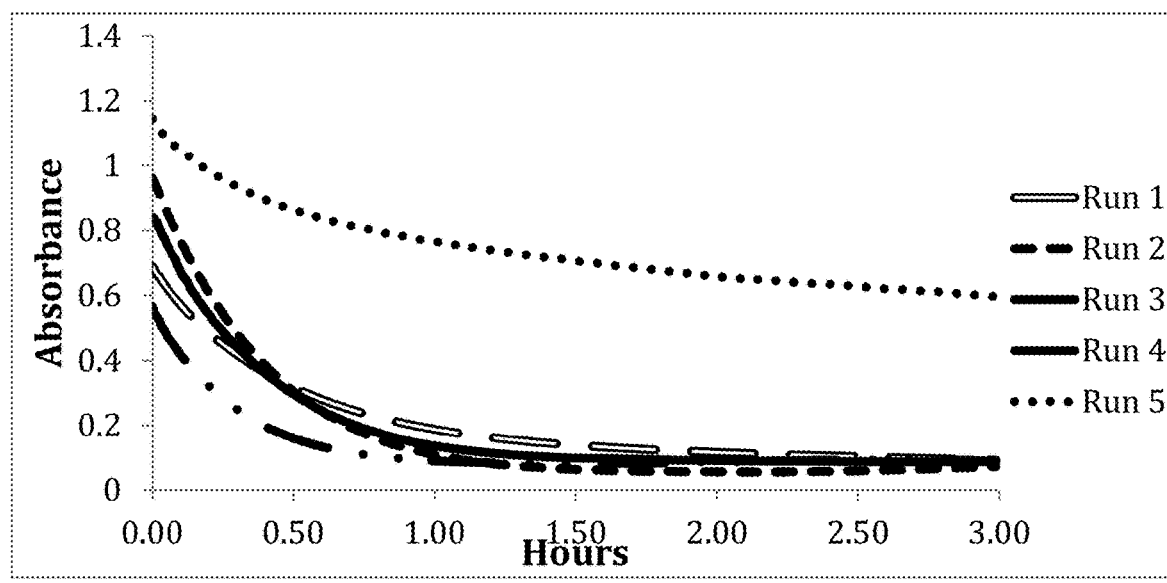
Figure 19:
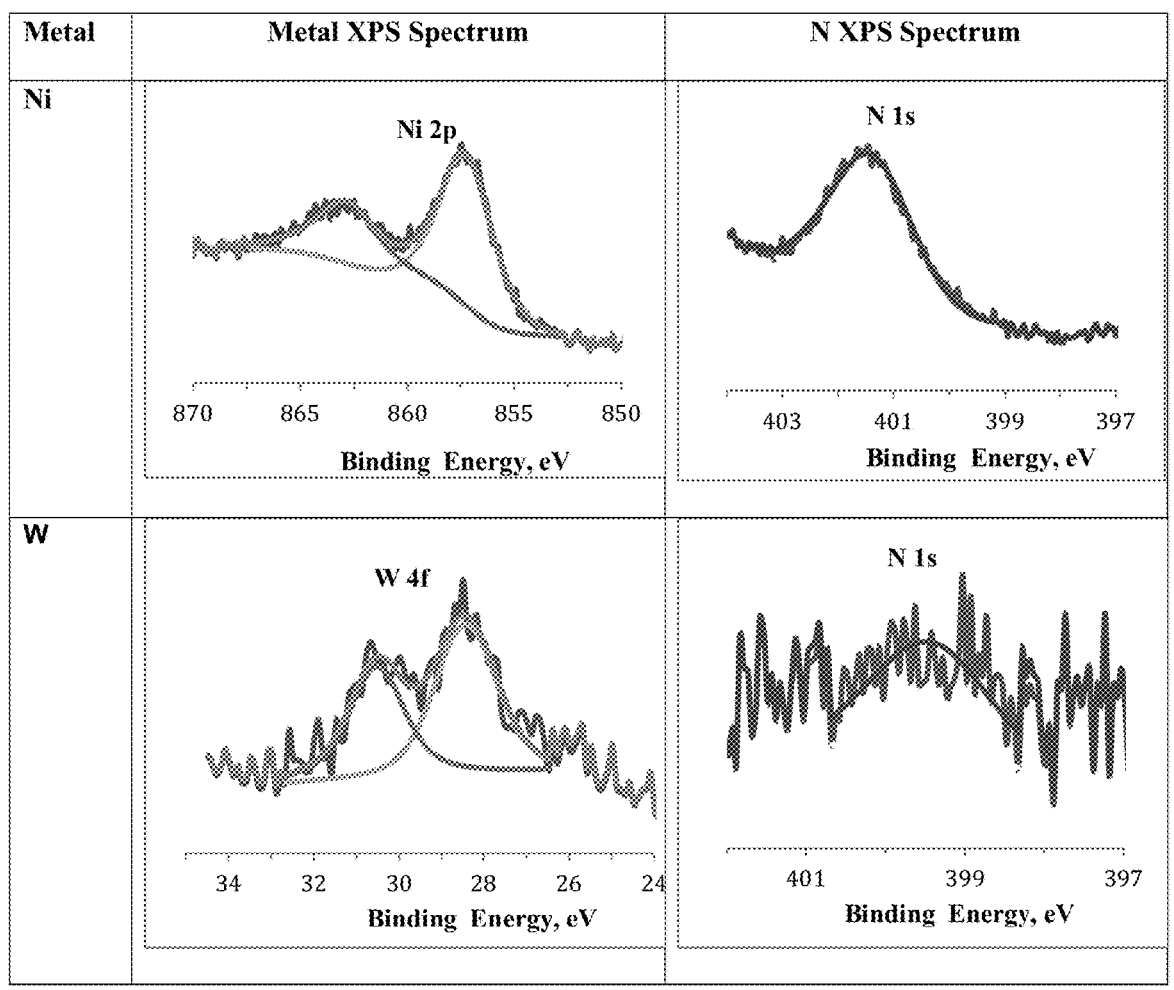
Figure 20:
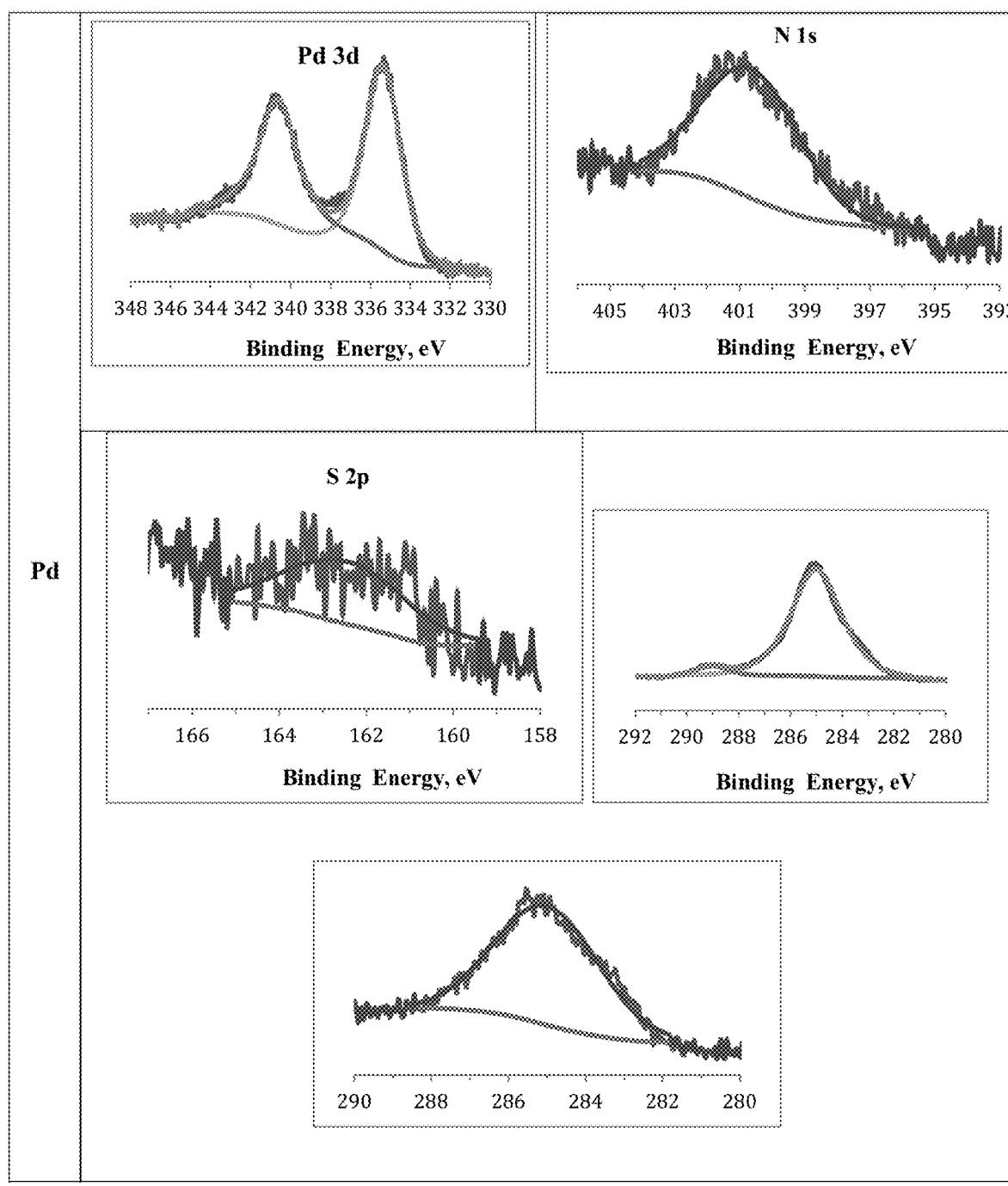
Figure 21A:
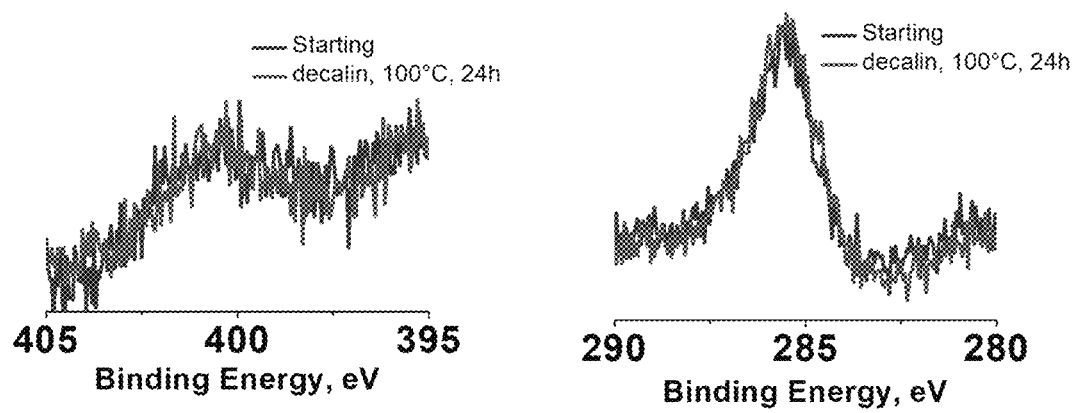

FIG. 2B depicts an STM image of the monolayer prepared from the carbonate salt of NHC-1 on Au(111) demonstrating highly ordered self-assembly. A repeating lattice unit 2.65 times the length of the underlying Au lattice was observed. In each repeat unit, bright regions corresponded to the NHC molecule, while the dark regions represented the underlying Au layer;

FIG. 2C depicts N(1s) and C(1s) XPS data that indicate chemical stability of NHC-1 on Au(111) to treatment with boiling non-aqueous and aqueous solutions (left and centre), and only slight erosion of the surface after treatment with 1% $H_2O_2$ for 24 h (right);

FIG. 2D depicts N(1s) and C(1s) XPS data that indicate complete stability of NHC-3 on Au(111) films (see Table 1) in hot solvent (left), but decomposition of the film in boiling water (right), which is indicative of a lower stability of surfaces formed from NHC-3;

FIG. 2E depicts representative XPS data for the treatment of NHC-1-terminated Au(111) surfaces with 1 mM solutions of dodecanethiol for 24 h at room temperature; the XPS spectra showed no S(2p) signal, indicating no thiol incorporation, while the N(1s) and C(1s) spectra suggest that the NHC-1 remained bound;

FIG. 3A depicts the reaction of azide-terminated NHC-6 with Au(111) (see Table 1) and subsequent conversion into a triazole by a Cu-catalyzed click reaction with propargyl alcohol;

FIG. 3B depicts XPS measurements on the azide-terminated NHC surface that showed a contact angle of 78±3°, and XPS analysis of the surface showed three N signals as expected: one for the two virtually equivalent nitrogen atoms of the NHC portion, one for the central nitrogen of the azide (at approximately 406 eV) and one signal for the remaining two, highly similar nitrogen atoms of the azide;

FIG. 3C depicts XPS measurements of the same surface after reaction with propargyl alcohol; the contact angle decreased to 45±3°, consistent with an alcohol-terminated surface and the XPS analysis of N(1s) changed, indicating triazole formation, such that only two types of N atoms were observed and the diagnostic, central N atom of the azide at 406 eV was absent;

FIG. 3D depicts representative XPS data for the treatment of dodecanethiol-protected Au(111) surfaces with solutions of NHC-1 for 24 h at room temperature; the XPS spectra showed that approximately 40% of the S(2p) signal remained (the asymmetric peak was due to the presence of two electronic states, $S(2p^{3/2})$ and $S(2p^{1/2})$), and an N(1s) signal was observed, which indicated a displacement of approximately 60% of the thiol by the NHC;

FIG. 3E depicts representative XPS data for the treatment of dodecanethiol-protected Au(111) surfaces with solutions of NHC-3 for at 0 min and at 24 h at room temperature; the XPS spectra showed that approximately 45% of the S(2p) signal remained after 24 hrs and an N(1s) signal, which was not observable initially, was apparent after 24 hrs. This indicated a displacement of approximately 55% of the thiol by the NHC (the asymmetric peak was due to the presence of two electronic states, $S(2p^{3/2})$ and $S(2p^{1/2})$);

FIG. 4 depicts various bonding modes calculated for NHC-1 on Au(111) and Au—C bond energies calculated by DFT; bonding of the NHC to the surface via an a-top site provided the most stable complex with a bond length in the region expected for molecular NHC-Au complexes (note that any stabilizing effect of stacking of the benzimidazolylidene units was not factored into these calculations which featured isolated NHCs on Au(111));

FIG. 5 depicts a high magnification image of NHC-3 on Au(111) that showed the presence of disorganized NHC-3 molecules, which appear as small light regions rather than stacks as observed in FIG. 2B;

FIG. 6 depicts a low magnification image of NHC-1 on Au(111) that showed a low density of dark areas that indicated sites where the lower level gold atoms had been removed and redistributed, likely to step edges (one step edge was shown);

FIG. 7A depicts a low magnification image of NHC-1 on Au(111) that showed a low density of dark areas that indicated sites where the lower level gold atoms had been removed and redistributed, likely to step edges (one step edge was shown);

FIG. 7B depicts a low magnification image of NHC-3 on Au(111) that showed a high density of dark areas compared to FIG. 6; the dark areas indicated sites where the lower level gold atoms were removed and redistributed, potentially to step edges, which was possibly promoted by the bulky size of NHC-3 compared to NHC-1; islanding was also shown by white spots, which were more significant for films of NHC-3 than NHC-1;

FIG. 8 depicts XPS data of films of NHC-1 on Au(111) before (tall peaks) and after (small peaks) it was exposed to 3% $H_2O_2$ for 24 h, and showed decomposition;

FIG. 9 depicts XPS data of films of NHC-1 on Au(111) before and after (overlapping peaks) it was exposed to pH 2 (left) and pH 12 (right) for 24 h; both cases showed stability;

FIG. 10 depicts representative XPS data (experimental and fitted) for NHC-1 on Au(111) and Au nanoparticles, the top row shows N(1s) and C(1s) on Au(111), the bottom row of spectra shows N(1s), C(1s), and S(2p) on Au nanoparticles;

FIG. 11 depicts representative XPS data (experimental and fitted) for NHC-2 on Au(111) and Au nanoparticles (see Table 1): the top row shows N(1s) and C(1s) on Au(111); the bottom row of spectra shows N(1s), C(1s), and S(2p) on Au nanoparticles;

FIG. 12 depicts representative XPS data for NHC-3 on gold surfaces and shows experimental and fitted spectra. The top row shows N(1s) and C(1s) on Au(111), the bottom row of spectra shows N(1s), C(1s), and S(2p) on Au nanoparticles;

FIG. 13 depicts representative XPS data for NHC-4 on gold surfaces (see Table 1) and shows experimental and fitted spectra. The top row shows N(1s) and C(1s) on flat Au (111), the bottom row of spectra shows N(1s), C(1s), and S(2p) on Au nanoparticles;

FIG. 14 depicts representative XPS data for NHC-5 on gold surfaces (see Table 1) and shows experimental and fitted spectra. The top row shows N(1s) and C(1s) on flat gold Au(111), the bottom row of spectra shows N(1s), C(1s), and S(2p) on Au nanoparticles;

FIG. 15 depicts the XPS spectroscopy results for the deposition of NHC-3, which was obtained from a hydrogen carbonate salt of NHC-3 on Au(111) from wet methanol under air, dry methanol under air, and dry methanol under a $N_2$ atmosphere. These spectra were not different within experimental error, as shown by the overlapping data;

FIGS. 16A and 16B depict a comparison of surface plasmon resonance (SPR) scans for a NHC-16 carbene chip (see Table 1) before (16A) and after (16B) heating at 65° C. for 24 hours (4 cycles in phosphate buffered saline (PBS) buffer);

FIG. 17A depicts SPR data from a commercial HPA chip in PBS buffer;

FIG. 17B depicts SPR data from a NHC-16 carbene chip in PBS buffer;

FIG. 18A depicts a plot of absorbance versus time for an experiment showing that NHC-functionalized gold samples (for example, NHC-10 gold samples (see Table 1)) are capable of decomposing ceric ammonium nitrate, which may be occurring by water oxidation;

FIG. 18B depicts a plot of absorbance versus time for an experiment showing that NHC-15 gold samples (see Table 1) are capable of decomposing ceric ammonium nitrate, which may be occurring by water oxidation;

FIG. 19 depicts XPS spectra of NHC-1 on Ni foil (upper panels) and on W wire (lower panels, N is present in both cases, indicating deposition of the N-containing NHC;

FIG. 20 depicts XPS spectra for NHC-1-coated Pd nanoparticles;

FIG. 21A depicts XPS spectra for NHC-X deposited on Au(111) from a hydrogen carbonate precursor before (red) and after (green) treatment in decalin at 100° C. for 24 h.

Figure 21B:
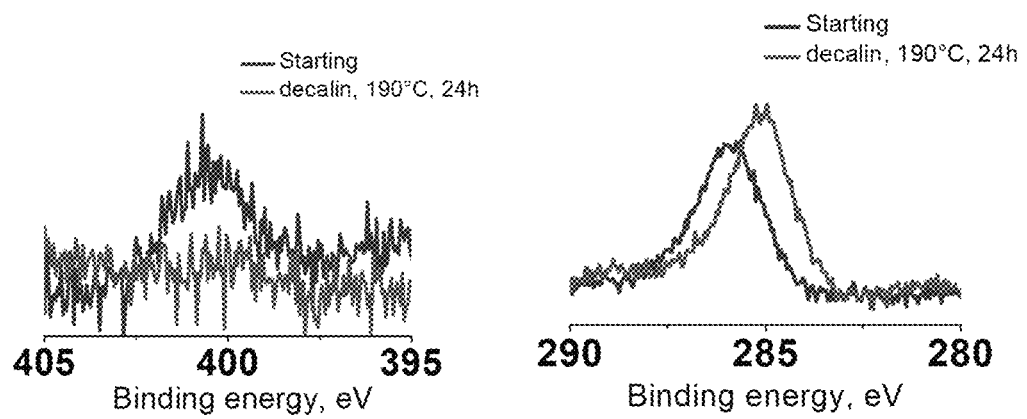
Figure 22:
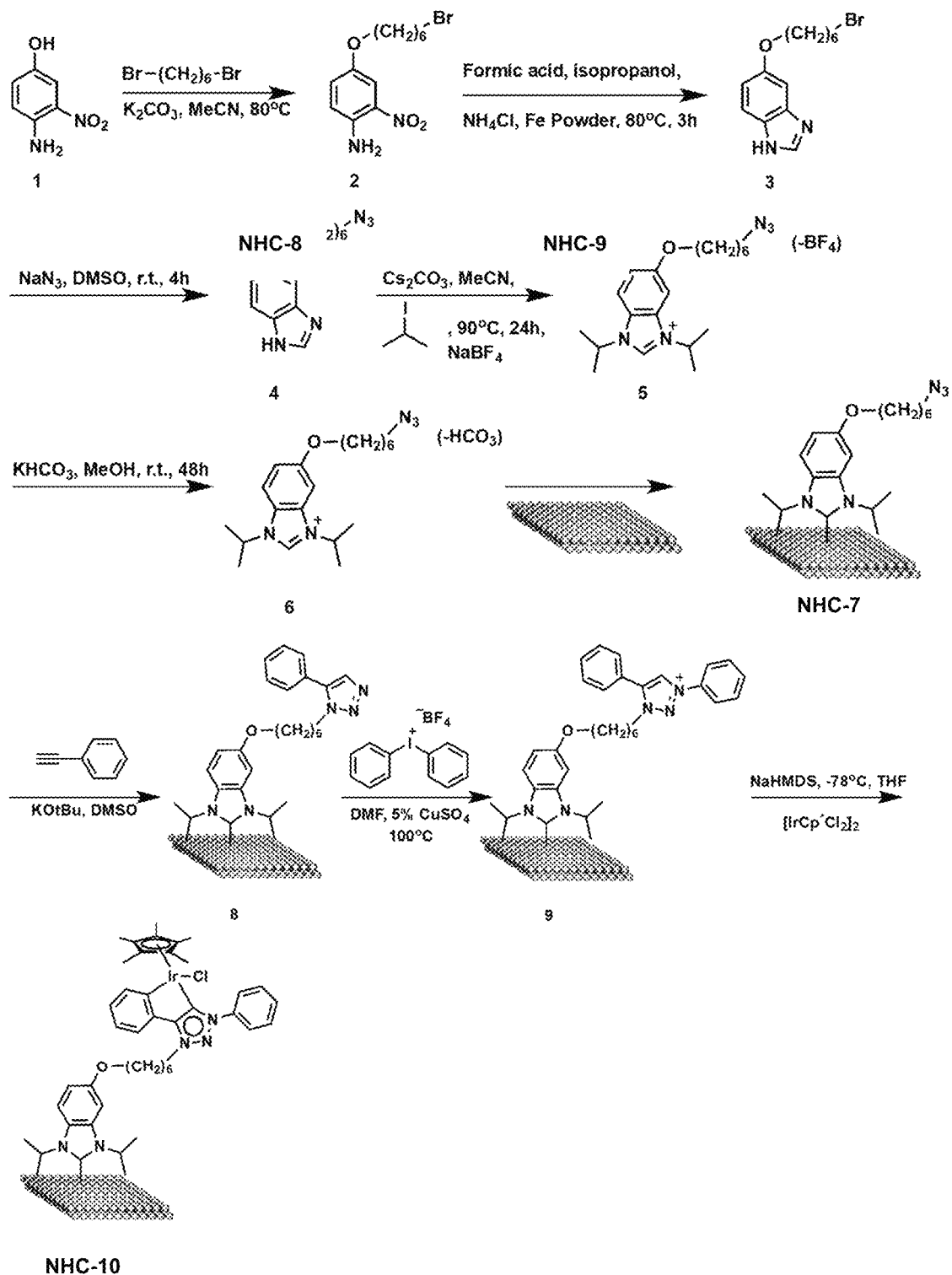

FIG. 21B depicts XPS spectra for NHC-X deposited on Au(111) from a hydrogen carbonate precursor before (red) and after (green) treatment in decalin at 190° C. for 24 h FIG. 22 depicts Scheme 1, synthesis of NHC-10.

Figure 23:
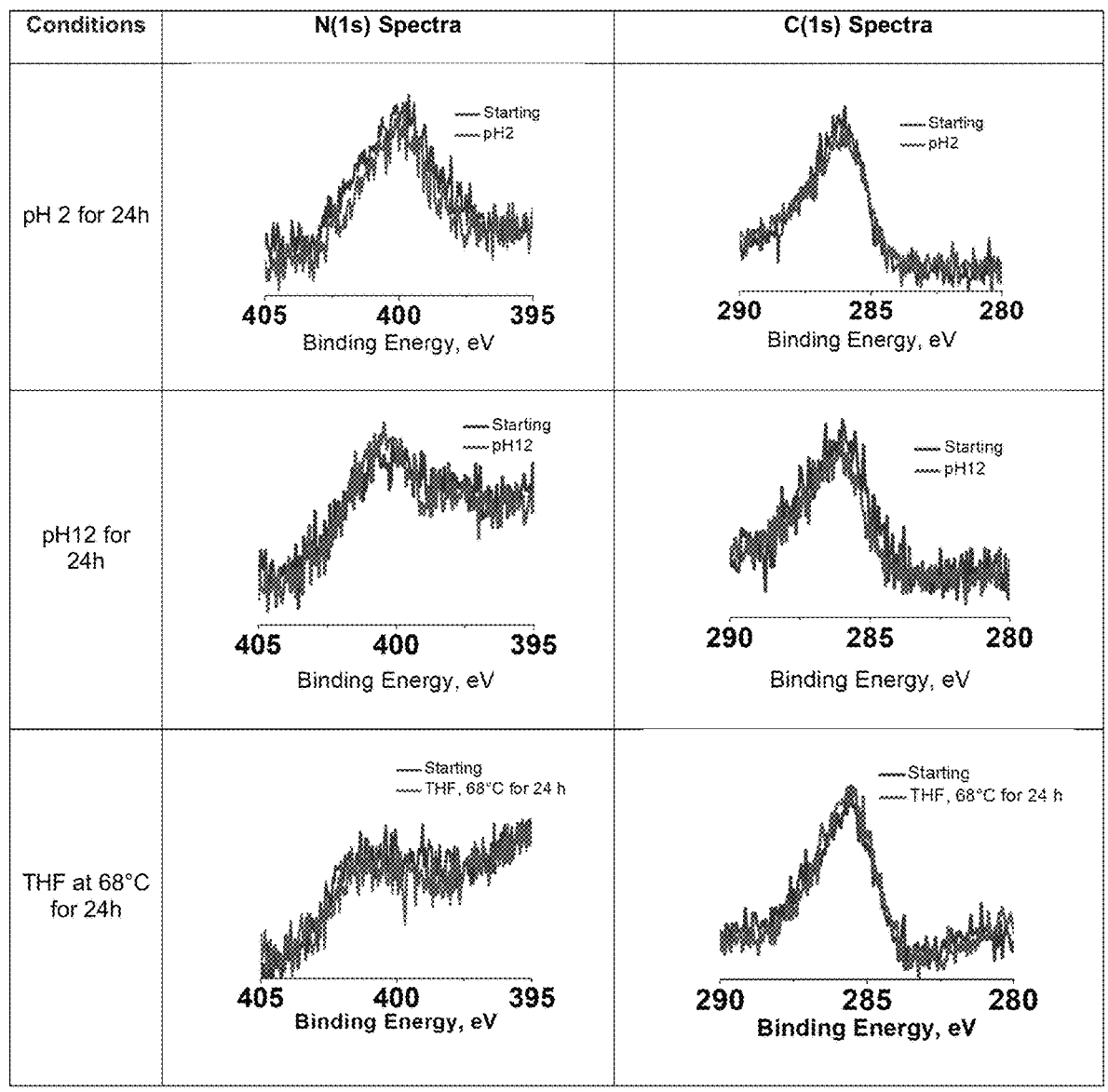
Figure 23:
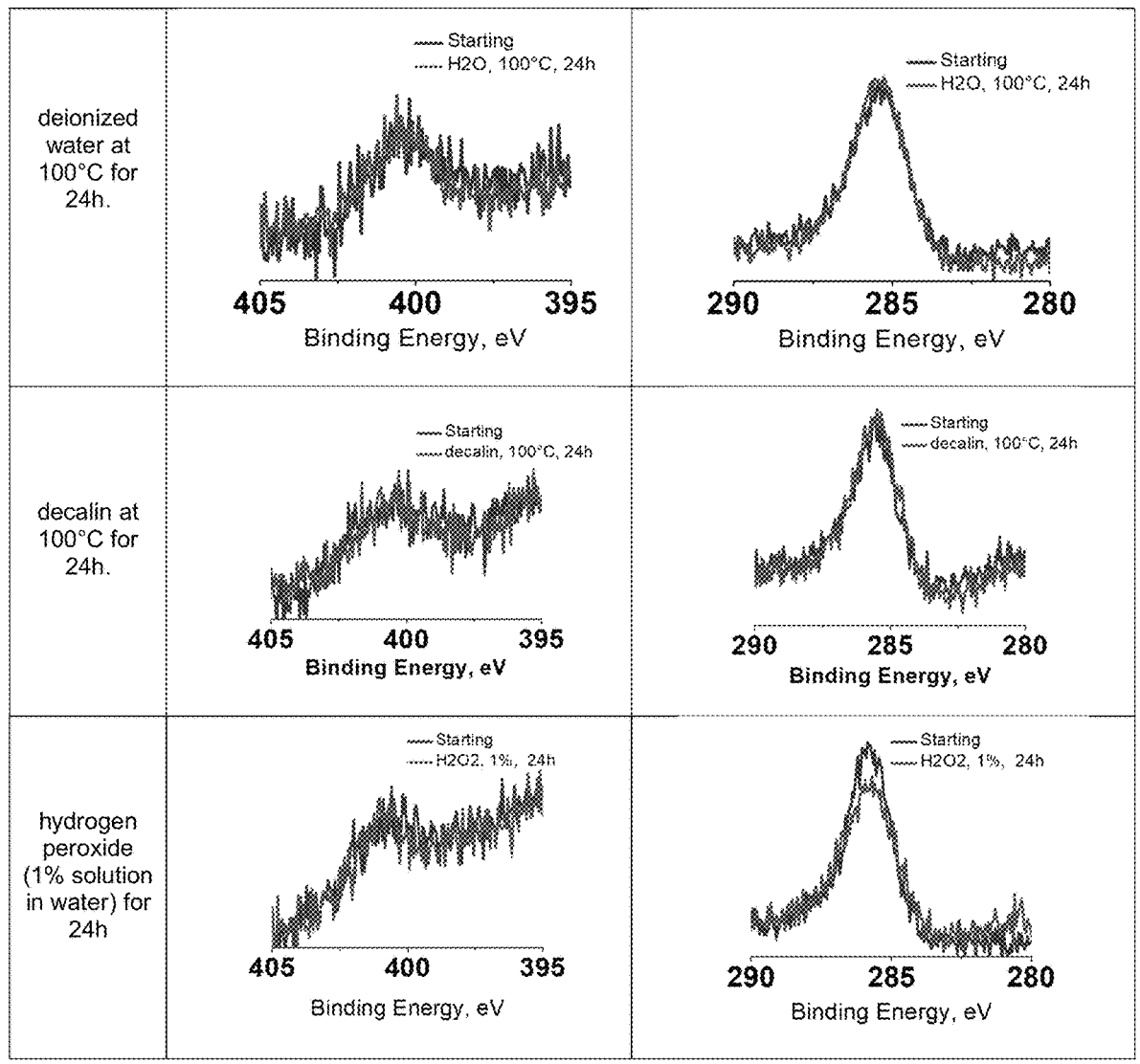

FIG. 23 shows Table 3, which presents results of stability tests of a representative NHC on Au(111). For most of these XPS spectra, there is a high degree of overlap, suggesting no change following exposure to the stated conditions. In the C(1s) spectra on the last line, the upper spectrum is under starting conditions, and the lower spectrum is after 24 hrs.

DETAILED DESCRIPTION

Definitions

Unless defined otherwise, all technical and scientific terms used herein have the same meaning as commonly understood by one of ordinary skill in the art to which this invention belongs.

As used in the specification and claims, the singular forms "a", "an" and "the" include plural references unless the context clearly dictates otherwise.

The term "comprising" as used herein will be understood to mean that the list following is non-exhaustive and may or may not include any other additional suitable items, for example one or more further feature(s), component(s) and/or ingredient(s) as appropriate.

As used herein, "substituted" means having one or more substituent moieties whose presence either facilitates or improves the desired reaction, or does not impede the desired reaction. A "substituent" is an atom or group of bonded atoms that can be considered to have replaced one or more hydrogen atoms attached to a parent molecular entity. Examples of substituents include alkyl, alkenyl, alkynyl, aryl, aryl-halide, heteroaryl, cycloalkyl (non-aromatic ring), Si(alkyl)$_3$, Si(alkoxy)$_3$, halo, alkoxyl, amino, alkylamino, alkenylamino, amide, amidine, hydroxyl, thioether, alkylcarbonyl, alkylcarbonyloxy, arylcarbonyloxy, alkoxycarbonyloxy, aryloxycarbonyloxy, carbonate, alkoxycarbonyl, aminocarbonyl, alkylthiocarbonyl, phosphate, phosphate ester, phosphonato, phosphinato, cyano, acylamino, imino, sulfhydryl, alkylthio, arylthio, thiocarboxylate, dithiocarboxylate, sulfate, sulfato, sulfonate, sulfamoyl, sulfonamide, nitro, nitrile, azido, heterocyclyl, ether, ester, silicon-containing moieties, thioester, or a combination thereof. The substituents may themselves be substituted. For instance, an amino substituent may itself be mono or independently disubstituted by further substituents defined above, such as alkyl, alkenyl, alkynyl, aryl, aryl-halide and heteroaryl cycloalkyl (non-aromatic ring).

As used herein, "aliphatic" refers to hydrocarbon moieties that are linear, branched or cyclic, may be alkyl, alkenyl or alkynyl, and may be substituted or unsubstituted. "Alkenyl" means a hydrocarbon moiety that is linear, branched or cyclic and contains at least one carbon to carbon double bond. "Alkynyl" means a hydrocarbon moiety that is linear, branched or cyclic and contains at least one carbon to carbon triple bond.

As used herein, "alkyl" refers to a linear, branched or cyclic, saturated or unsaturated hydrocarbon, which consists solely of single-bonded carbon and hydrogen atoms, which can be unsubstituted or is optionally substituted with one or more substituents, for example a methyl or ethyl group. Examples of saturated straight or branched chain alkyl groups include, but are not limited to, methyl, ethyl, 1-propyl, 2-propyl, 1-butyl, 2-butyl, 2-methyl-1-propyl, 2-methyl-2-propyl, 1-pentyl, 2-pentyl, 3-pentyl, 2-methyl-1-butyl, 3-methyl-1-butyl, 2-methyl-3-butyl, 2,2-dimethyl-1-propyl, 1-hexyl, 2-hexyl, 3-hexyl, 2-methyl-1-pentyl, 3-methyl-1-pentyl, 4-methyl-1-pentyl, 2-methyl-2-pentyl, 3-methyl-2-pentyl, 4-methyl-2-pentyl, 2,2-dimethyl-1-butyl, 3,3-dimethyl-1-butyl and 2-ethyl-1-butyl, 1-heptyl and 1-octyl. As used herein the term "alkyl" encompasses cyclic alkyls, or cycloalkyl groups.

The term "cycloalkyl" as used herein refers to a non-aromatic, saturated or partially saturated, monocyclic, bicyclic or tricyclic hydrocarbon ring system containing at least 3 carbon atoms. Examples of $C_3$-$C_n$ cycloalkyl groups include, but are not limited to, cyclopropyl, cyclobutyl, cyclopentyl, cyclohexyl, cycloheptyl, cyclooctyl, norbornyl, adamantyl, bicyclo[2.2.2]oct-2-enyl, and bicyclo[2.2.2]octyl.

As used herein, "alkenyl" means a hydrocarbon moiety that is linear, branched or cyclic and comprises at least one carbon to carbon double bond which can be unsubstituted or optionally substituted with one or more substituents. "Alkynyl" means a hydrocarbon moiety that is linear, branched or cyclic and comprises at least one carbon to carbon triple bond which can be unsubstituted or optionally substituted with one or more substituents.

As used herein, "aryl" and/or "aromatic ring" refers to hydrocarbons derived from benzene or a benzene derivative that are unsaturated aromatic carbocyclic groups from 6 to 100 carbon atoms, or from which may or may not be a fused ring system, in some embodiments 6 to 50, in other embodiments 6 to 25, and in still other embodiments 6 to 15. The aryls may have a single or multiple rings. The term "aryl" and/or "aromatic ring" as used herein also includes substituted aryls and/or aromatic rings. Examples include, but are not limited to, phenyl, naphthyl, xylene, phenylethane, substituted phenyl, substituted naphthyl, substituted xylene, substituted 4-ethylphenyl and the like.

As used herein, the term "Au(111)" refers to a single crystal of gold, either alone or supported on a substrate (e.g. mica) that has a particularly flat orientation of its atoms on the surface of the crystal. (111) refers to a dominant arrangement of exposed surface atoms to form a 1,1,1 crystal plane (Miller indices x=y=z=+1).

As used herein, "polycrystalline gold" refers to a gold sample that has many small crystals of the same or different crystal structure adhered to a substrate, such as, but not limited to, a silicon wafer (the silicon wafer may be pre-coated with a chromium or titanium layer for improved adhesion). Such polycrystalline gold can be used for electrochemical applications. The surface texture of polycrystalline gold can be rougher than the smooth Au(111) referred to above; however, polycrystalline gold's dominant arrangement of exposed surface atoms is typically (111). The rms-roughness (rms=root mean squared) of the polycrystalline samples used herein was less than 2.5 nm As used herein, "cycle" refers to an aromatic or nonaromatic monocyclic, bicyclic, or fused ring system of carbon atoms, which can be substituted or unsubstituted. Included within the term "cycle" are cycloalkyls and aryls, as defined above.

As used herein, "heteroaryl" or "heteroaromatic" refers to an aryl (including fused aryl rings) that includes heteroatoms selected from oxygen, nitrogen, sulfur and phosphorus. A "heteroatom" refers to an atom that is not carbon or hydrogen, such as nitrogen, oxygen, sulfur, or phosphorus. Heteroaryl or heteroaromatic groups include, for example, furanyl, thiophenyl, pyrrolyl, imidazoyl, benzamidazoyl, 1,2- or 1,3-oxazolyl, 1,2- or 1,3-diazolyl, 1,2,3- or 1,2,4-triazolyl, and the like.

As used herein, a "heterocycle" is an aromatic or non-aromatic monocyclic or bicyclic ring of carbon atoms and heteroatoms selected from oxygen, nitrogen, sulfur and phosphorus. Included within the term "heterocycle" are heteroaryls, as defined above. Also included within this term are monocyclic and bicyclic rings that include one or more double and/or triple bonds within the ring. Examples of 3- to 9-membered heterocycles include, but are not limited to, aziridinyl, oxiranyl, thiiranyl, azirinyl, diaziridinyl, diazirinyl, oxaziridinyl, azetidinyl, azetidinonyl, oxetanyl, thietanyl, piperidinyl, piperazinyl, morpholinyl, pyrrolyl, oxazinyl, thiazinyl, diazinyl, triazinyl, tetrazinyl, imidazolyl, benzimidazolyl, tetrazolyl, indolyl, isoquinolinyl, quinolinyl, quinazolinyl, pyrrolidinyl, purinyl, isoxazolyl, benzisoxazolyl, furanyl, furazanyl, pyridinyl, oxazolyl, benzoxazolyl, thiazolyl, benzthiazolyl, thiophenyl, pyrazolyl, triazolyl, benzodiazolyl, benzotriazolyl, pyrimidinyl, isoindolyl and indazolyl.

As used herein, the term "mesityl" refers to the substituent derived from mesitylene, or 1,3,5-trimethylbenzene.

As used herein, "diisopropylphenyl" is the substituent

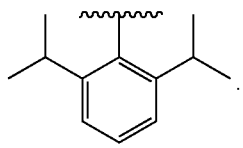 [SMILES: *c1c(C(C)C)cccc1C(C)C]

As used herein, "NHC" refers to a N-heterocyclic carbene. For convenience herein, certain N-heterocyclic carbenes are referred to as NHC-1, NHC-2, etc. Structural formulae and names of these NHCs and NHCs on metal are presented in Table 1.

As used herein, a "chemically derivatizable group" is any functional group capable of participating in a chemical reaction, such as, but not limited to, electrophilic/nucleophilic substitution, addition, elimination, acid/base, reduction, oxidation, radical, pericyclic, Diels-Alder, metathesis or click chemistry reactions.

As used herein, the term "unsubstituted" refers to any open valence of an atom being occupied by hydrogen. Also, if an occupant of an open valence position on an atom is not specified then it is hydrogen.

As used herein, a "functional group" is a specific group of atoms within a molecule that are responsible for characteristic chemical reactions. Thus functional groups are moieties within a molecule that are likely to participate in chemical reactions.

As used herein, "carbene" is an electronically neutral species comprising a carbon having two nonbonding electrons (i.e., form a lone pair), which is referred to as the "carbene carbon." In the carbenes used in the method and materials of the present application, this carbon having the two nonbonding electrons is the carbon that will be bound to a metal surface and is divalent; in other words, this carbon is covalently bonded to two substituents of any kind, and bears two nonbonding electrons that may be spin-paired (singlet state), such that the carbon is available for formation of a dative bond.

As used herein, "N-heterocyclic carbene" refers to heterocyclic moiety that includes a carbene, as defined above, which is electronic and/or resonance stabilized, typically by the presence of one or more carbene-adjacent heteroatoms, and/or is sterically stabilized by substituents adjacent to the carbene. A non-limiting example of such a stabilized carbene is provided below:

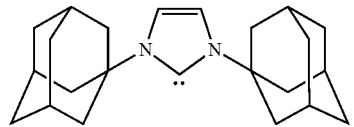

As would be well appreciated by a worker skilled in the art, there are many alternative substituents that would stabilize the carbene. Furthermore, as would be readily apparent to a worker skilled in the art, in the case of two stabilizing substituents, it is not necessary for the two substituents to be the same.

As used herein, a "carbene precursor" refers to a non-carbenic species that, under appropriate conditions, will generate a carbene in situ, such as an N-heterocyclic carbene, as defined above, either directly, or indirectly through a transient or intermediate species.

As used herein, a "self-assembled monolayer" is a molecular assembly formed spontaneously, from the vapour or liquid phase, onto surfaces by adsorption or chemisorption, and are organized into large, essentially ordered domains.

As used herein, the term "composite material" refers to materials made from two or more constituent materials having different physical or chemical properties. Such materials may be preferred for many reasons, such as materials, which are stronger, lighter or less expensive when compared to traditional materials. Typical composite materials are generally but not exclusively used for buildings, bridges and structures such as boat hulls, automotive and aircraft bodies, and storage tanks. Advanced examples perform on spacecraft in demanding environments.

As used herein, the term "dative bond" refers to a bond (a shared pair of electrons) forms between two atoms wherein both of the electrons that make up the bond came from the same atom.

As used herein, the term "uniform" when used to refer to a monolayer, as defined above, indicates that the monolayer is generally consistent, or without significant variation, across substantially the entirety of the functionalized surface.

As used herein, the term "stability" refers to both the physical and chemical stability of the herein described carbene monolayers. "Physical stability" refers to retention of improved physical properties of carbene monolayers on a timescale of their expected usefulness in the presence of air, moisture or heat, and under the expected conditions of application. This physical stability is relative to other self-assembled monolayer-functionalized surfaces, such as thio-functionalized surfaces. "Chemical stability" refers to thermodynamic stability of the carbene monolayers upon exposure to different chemicals or mixtures of chemicals, including but not limited to air, oxygen, water, acid, base, oxidant, reductant, etc. It may refer to a lack of undesired chemical reactivity exhibited by the carbene monolayers in the environment, or under the conditions, of normal use. That is, it retains its useful properties on the timescale of its expected usefulness in the presence of air, moisture or heat, and under the expected conditions of application. This chemical stability may be defined relative to other self-assembled monolayer-functionalized surfaces, such as thio-functionalized surfaces.

As used herein, the term "contaminant" or "contamination" refers to any elemental, atomic or molecular species, or combination thereof, whose presence impedes the desired reactions to form the herein described composite materials, or impedes the desired purity, stability, or properties of the final composite materials.

As used herein, a "metal film" refers to a metal layer that has lateral dimensions (i.e., thickness) in the range of 0.1-100 nm, or alternatively 0.1-100 µm, or alternatively >100 µm.

As used herein, "Au(NP)" refers to gold nanoparticles. As used herein, a "nanoparticle" is a plurality of metal atoms, with at least one dimension less than 100 nm, that together form a nano-scale geometric shape that is optionally multi-faceted. Properties of a metal nanoparticle typically deviate from the properties of a bulk metal.

As used herein, a "single crystal metal" refers to an entire metal sample in which a crystal lattice is continuous and unbroken to the edges of the sample.

The term "immersing" or "immersion" as used herein will be understood to mean any method of contacting a metal-containing material with carbenes, as described herein, and/or carbene precursors, as described herein, in such a manner that a metal surface of the metal-containing material is fully or partially covered by the carbenes and/or carbene precursors.

Immersing can include, but is not limited to, dipping a metal material into a solution, pouring or flowing a solution over a metal surface, spraying a metal surface with a solution, or roll coating a surface.

As used herein, the term "vapour depositing" refers to deposition of a film, coating, or self-assembled monolayer onto a surface in a vacuum environment, at temperatures≤0° C., or alternatively between 0-25° C., or alternatively between 25-100° C., or alternatively ≥100° C.

As used herein, "microelectronic devices" refers to very small electronic designs and/or components that are made from semiconducting materials and manufactured on the micrometer scale, or smaller, Examples of such devices include, but are not limited to, transistors, capacitors, inductors, resistors, diodes, insulators, conductors or combinations thereof.

As used herein, the term "surface properties" refers to properties imparted to a surface as a result of being functionalized by heterocyclic carbenes, as described herein. Examples of said surface properties include, but are not limited to, hydrophobicity/hydrophilicity, conductivity, electrical impedance, piezoelectricity, absorbance, radiance, fluorescence, chemical or biochemical reactivity, or luminescence.

As used herein, the term "sensing applications" refers to systems, methods, procedures, and/or instruments that use sensors to receive and respond to signals and/or stimuli. Examples of sensors can include, but are not limited to, optical sensors (based on, for example, absorbance, reflectance, luminescence, fluorescence, or light scattering effects); electrochemical sensors (based on, for example, voltammetric, amperometric, and potentiometric effects, chemically sensitized field effect transistors, or potentiometric solid electrolyte gas sensors); electrical sensors (based on, for example, metal oxide semiconductors or organic semiconductors); mass-sensitive sensors (based on, for example, piezoelectric or surface acoustic wave effects); magnetic sensors (based on, for example, paramagnetic properties); thermometric sensors (based on, for example, heat effects of a specific chemical reaction, or adsorption); radiation sensitive sensors (based on, for example, absorbance or radiation emission); biosensors (based on, for example, signal transduction, biological recognition elements, or an analyte being sensed) [D. Buenger, F. Topuz, J. Groll, *Progress in Polymer Science* 37, 1678 (2012)]. Specific sensing applications can include, but are not limited to, surface plasmon resonance.

As used herein the abbreviation "XPS" is used to refer to X-ray photoelectron spectroscopy. A typical XPS spectrum is a plot of number of electrons detected as a function of the binding energy of detected electrons. Each element produces a characteristic set of XPS peaks at characteristic binding energy values. The peaks identify each element, and often its oxidation state, that exists on, or some 100 nm below, a surface being analyzed. XPS reveals the number of detected electrons in each of the characteristic peaks. This number is related to the amount of an element within the sample, and it reveals whether contamination, if any, exists at the surface or in the bulk of the sample.

As used herein, the term 'metal chip' refers to a composite material in which a glass substrate has had a metal film deposited on it, comprising appropriate connections such that it can be incorporated into a commercial surface plasmon resonance instrument.

Description

Formation of reactive, surface-bound alkylidenes has been reported [E. M. Zahidi, et al. *Nature* 409, 1023 (2001); G. S. Tulevski, et al. *Science* 309, 591 (2005)]. In one example, an NHC containing a reactive metal alkylidene was prepared on gold, but achieved only a 20% monolayer coverage that demonstrated no stability or ordering [A. V. Zhukhovitskiy, et al. *J. Am. Chem. Soc.* 135, 7418 (2013)]. In another report of a non-reactive NHC carbene on flat Au surfaces, an ordered NHC film was inferred from near edge X-ray adsorption fine structure (NEXAFS) C K-edge spectroscopy, but no stability studies were performed and no potential for derivatization illustrated [T. Weidner et al., *Aust. J. Chem.* 64, 1177 (2011)]. With respect to nanoparticles, examples of NHC-Au species have been reported, wherein stability was either poor, required rigorous conditions to achieve, or was undetermined [J. Vignolle, et al. *Chem. Commun.* 7230 (2009); E. C. Hurst, et al. *New J. Chem.* 33, 1837 (2009); R. T. W. Huang, et al. *Dalton Trans.* 7121 (2009)].

The present application provides composite materials that comprise a carbene-functionalized metal surface. In one aspect, the composite material comprises a metal-containing component having a metal surface on which a carbene monolayer has been generated. The monolayer interacts with the metal surface via dative bonds formed between the carbene carbon and the metal atoms. As described herein, such carbene monolayers are stable, uniform and generally free from contaminants. In certain embodiments, the carbene monolayer is a self-assembled monolayer.

In terms of uniformity, examples of the herein described carbene-functionalized composite materials comprise a monolayer that exhibits uniformity across an entire treated area of a metal surface. In examples described herein, any variation across the monolayer that was detected was minimal.

In terms of stability, it has been determined that certain carbene monolayers produced according to the methods described herein are stable to a variety of conditions. Certain of these monolayers have been determined to be stable since they did not degrade under ambient conditions for at least 3 months. Certain other monolayers did not degrade under ambient conditions for at least 2 months. Furthermore, studies have been performed to demonstrate that certain monolayers are stable even with exposure for at least 24 hours to aqueous solutions having pHs in the range of 2-12. Similarly, exposure of composite materials to refluxing tetrahydrofuran ("THF"), at the boiling point of THF (66° C.), or to boiling water, showed that certain monolayers were stable to THF and/or boiling water for at least 24 hours. Exposure of composite materials to 1% $H_2O_2$ for 24 hours resulted in minimal degradation (<5%) of certain carbene monolayers.

In accordance with certain embodiments, carbene monolayers of the present composite materials contain less than 15% contaminants, by weight, or less than 10%, or less than 5%, or less than 2%, or less than 1%, or less than 0.5%. In a specific example, the carbene monolayer of the present composite materials comprises about 5% contaminants by weight, or less.

Carbene monolayers can be manufactured by contacting (for example, by immersing) a metal surface with a carbene-containing liquid composition (or pure liquid carbene if possible, depending on a carbene's physical properties). Alternatively, certain carbene monolayers can be formed from carbene precursors, which form carbenes in situ.

In accordance with one embodiment, certain carbene monolayers comprise one or more carbenes of formula I

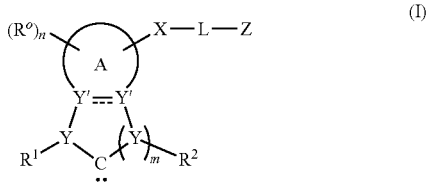

(I)

wherein:
n is an integer from 1 to 8, or from 1 to 4;
m is an integer from 0 to 4;
A is absent, an aliphatic cycle, a heterocycle, an aromatic ring, a fused aromatic ring system, a heteroaromatic ring, and/or a fused heteroaromatic ring system, each of which is optionally substituted;
X-L-Z is absent, or
X is C or a heteroatom,
L is a divalent moiety, such as $C_1$-$C_{10}$ alkylene, $C_{10}$-$C_{20}$ alkylene, $C_1$-$C_{10}$ alkenylene, $C_{10}$-$C_{20}$ alkenylene, $C_1$-$C_{10}$ alkynylene, $C_{10}$-$C_{20}$ alkynylene, or dextran, a simple sugar, complex sugar, carbohydrate, ether, thioether, amine, polyamine, polyether, and/or polythioether, each of which is optionally substituted;
Z is H, an aliphatic cycle, a heterocycle, an aromatic ring, a fused aromatic ring system, a heteroaromatic ring, a fused heteroaromatic ring system, an organometallic complex, a transition-metal catalyst, a metal-oxide catalyst, a simple sugar, a complex sugar, a carbohydrate, or a chemically derivatizable group, such as —OH, azide, carboxylic acid, carbonyl chloride, anhydride, ester, aldehyde, alcohol, amine, halogen, epoxide, thiirane, aziridine, amino acid, nucleic acid, alkene, alkyne, conjugated diene, thiol, or thioester, each of which is optionally substituted;
each Y or Y' is independently C or a heteroatom;
each R° is independently H, halogen, the substituent X-L-Z as defined above, $C_1$-$C_{10}$ alkyl, $C_{10}$-$C_{20}$ alkyl, $C_1$-$C_{10}$ alkenyl, $C_{10}$-$C_{20}$ alkenyl, $C_1$-$C_{10}$ alkynyl, or $C_{10}$-$C_{20}$ alkynyl, $C_1$-$C_{10}$ alkoxyl, $C_{10}$-$C_{20}$ alkoxyl, $C_3$-$C_{20}$ cyclic aliphatic moiety, aryl, heteroaryl, ether, thioether, amine, polyamine, polyether, or polythioether, each of which is optionally substituted; or, two of R°, together with the atoms to which they are attached, are connected to form a cycle, or heterocycle, each of which is optionally substituted; and $R^1$ and $R^2$ are independently absent, at least one lone pair of electrons, H, $C_1$-$C_{10}$ alkyl, $C_{10}$-$C_{20}$ alkyl, $C_1$-$C_{10}$ alkenyl, $C_{10}$-$C_{20}$ alkenyl, $C_1$-$C_{10}$ alkynyl, $C_{10}$-$C_{20}$ alkynyl, $C_3$-$C_{20}$ cyclic aliphatic moiety, aryl, heteroaryl, ether, thiol, thioether, amine, polyamine, polyether, polythioether, or polythiol, each of which is optionally substituted; or, one of $R^1$ or $R^2$, with one of R°, together with the atoms to which they are attached, are connected to form a cycle, or heterocycle, each of which is optionally substituted; wherein, when A is absent or non-aromatic, the dashed line represents an optional double bond; and/or
when A is absent, each Y' is independently bonded to R° or X-L-Z, as defined above.

In one embodiment, the carbene is a compound of formula Ia

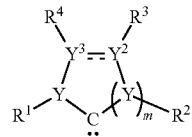

(Ia)

wherein:
m is an integer from 0 to 4;
each Y is independently C or a heteroatom;
$Y^2$ and $Y^3$ are independently C or a heteroatom, and the dashed line represents an optional double bond;
$R^1$ and $R^2$ are independently absent, at least one lone pair of electrons, H, $C_1$-$C_{10}$ alkyl, $C_{10}$-$C_{20}$ alkyl, $C_1$-$C_{10}$ alkenyl, $C_{10}$-$C_{20}$ alkenyl, $C_1$-$C_{10}$ alkynyl, $C_{10}$-$C_{20}$ alkynyl, $C_3$-$C_{20}$ cyclic aliphatic moiety, aryl, heteroaryl, ether, thiol, thioether, amine, polyamine, polyether, polythioether, or polythiol, each of which may be optionally substituted;
$R^3$ and $R^4$ are independently H, halogen, the substituent X-L-Z as defined for Formula I, $C_1$-$C_{10}$ alkyl, $C_{10}$-$C_{20}$ alkyl, $C_1$-$C_{10}$ alkenyl, $C_{10}$-$C_{20}$ alkenyl, $C_1$-$C_{10}$ alkynyl, $C_{10}$-$C_{20}$ alkynyl, $C_3$-$C_{20}$ cyclic aliphatic moiety, $C_1$-$C_{10}$ alkoxyl, $C_{10}$-$C_{20}$ alkoxyl, $C_3$-$C_{20}$ cyclic aliphatic moiety, aryl, heteroaryl, ether, thioether, amine, polyamine, polyether, or polythioether, each of which is optionally substituted; or, any one of $R^3$ or $R^4$, with any one of $R^1$ or $R^2$, together with the atoms to which they are attached, are connected to form a cycle, or heterocycle, each of which is optionally substituted.

In certain embodiments, $R^1$ and $R^2$ are independently methyl, ethyl, propyl, butyl, isopropyl, phenyl, mesityl, or diisopropylphenyl, each of which may be optionally substituted.

In an alternative embodiment, certain monolayers are formed from a carbene precursor, such that a carbene is formed in situ in preparation of carbene monolayers. In one example of this embodiment, the carbene precursor is contacted with a metal surface (for example, by immersion and/or thermal decomposition) to form a carbene monolayer. This process is suitable, for example, when the carbene precursor is a compound of formula II

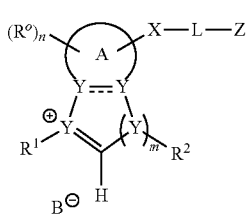

(II)

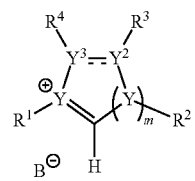

(IIa)

wherein:
- m is an integer from 0 to 4;
- B is a counter ion that optionally acts as a base;
- each Y is independently C or a heteroatom;
- $Y^2$ and $Y^3$ are independently C or a heteroatom, and the dashed line is an optional double bond;
- $R^1$ and $R^2$ are independently absent, at least one lone pair of electrons, H, $C_1$-$C_{10}$ alkyl, $C_{10}$-$C_{20}$ alkyl, $C_1$-$C_{10}$ alkenyl, $C_{10}$-$C_{20}$ alkenyl, $C_1$-$C_{10}$ alkynyl, $C_{10}$-$C_{20}$ alkynyl), cycloalkyl, aryl, heteroaryl, ether, thiol, thioether, amine, polyamine, polyether, polythioether, or polythiol, each of which is optionally substituted;
- $R^3$ and $R^4$ are independently H, halogen, the substituent X-L-Z as defined for Formula II, $C_1$-$C_{10}$ alkyl, $C_{10}$-$C_{20}$ alkyl, $C_1$-$C_{10}$ alkenyl, $C_{10}$-$C_{20}$ alkenyl, $C_1$-$C_{10}$ alkynyl, $C_{10}$-$C_{20}$ alkynyl, $C_1$-$C_{10}$ alkoxyl, $C_{10}$-$C_{20}$ alkoxyl, $C_3$-$C_{20}$ cyclic aliphatic, aryl, heteroaryl, ether, thioether, amine, polyamine, polyether, or polythioether, each of which is optionally substituted; or, any one of $R^3$ or $R^4$, with any one of $R^1$ or $R^2$, together with the atoms to which they are attached, are connected to form a cycle, or heterocycle, each of which is optionally substituted;

or, the carbene precursor is a compound of formula III:

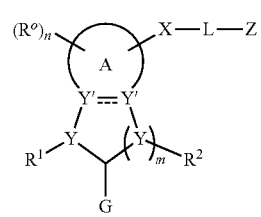

(III)

wherein:
- n is an integer from 1 to 4, or alternatively 1 to 8;
- m is an integer from 0 to 4;
- G is a perhalogenated alkyl, perhalogenated alkenyl, perhalogenated alkynyl, a perhalogenated aryl, or OR', wherein R' is an aliphatic group, for example, an alkyl group.
- A is absent, an aliphatic cycle, a heterocycle, an aromatic ring, a fused aromatic ring system, a heteroaromatic ring, and/or a fused heteroaromatic ring system, each of which is optionally substituted;
- X-L-Z is absent, or
- X is C or a heteroatom,
- L is a divalent moiety, such as $C_1$-$C_{10}$ alkylene, $C_{10}$-$C_{20}$ alkylene, $C_1$-$C_{10}$ alkenylene, $C_{10}$-$C_{20}$ alkenylene, $C_1$-$C_{10}$ alkynylene, $C_{10}$-$C_{20}$ alkynylene, or dextran, a simple sugar, complex sugar, carbohydrate, ether, thioether, amine, polyamine, polyether, and/or polythioether, each of which is optionally substituted;
- Z is H, an aliphatic cycle, a heterocycle, an aromatic ring, a fused aromatic ring system, a heteroaromatic ring, a wherein:
- n is an integer from 1 to 8, or from 1 to 4;
- m is an integer from 0 to 4;
- B is a counter ion that optionally acts as a base;
- A is absent, an aliphatic cycle, a heterocycle, an aromatic ring, a fused aromatic ring system, a heteroaromatic ring, and/or a fused heteroaromatic ring system, each of which is optionally substituted;
- X-L-Z is absent, or
- X is C or a heteroatom,
- L is a divalent moiety, such as $C_1$-$C_{10}$ alkylene, $C_{10}$-$C_{20}$ alkylene, $C_1$-$C_{10}$ alkenylene, $C_{10}$-$C_{20}$ alkenylene, $C_1$-$C_{10}$ alkynylene, $C_{10}$-$C_{20}$ alkynylene, or dextran, a simple sugar, complex sugar, carbohydrate, ether, thioether, amine, polyamine, polyether, and/or polythioether, each of which is optionally substituted;
- Z is H, an aliphatic cycle, a heterocycle, an aromatic ring, a fused aromatic ring system, a heteroaromatic ring, a fused heteroaromatic ring system, an organometallic complex, a transition-metal catalyst, a metal-oxide catalyst, a simple sugar, a complex sugar, a carbohydrate, or a chemically derivatizable group, such as —OH, azide, carboxylic acid, carbonyl chloride, anhydride, ester, aldehyde, alcohol, amine, halogen, epoxide, thiirane, aziridine, amino acid, nucleic acid, alkene, alkyne, conjugated diene, thiol, or thioester, each of which is optionally substituted;
- each Y or Y' is independently C or a heteroatom;
- each R° is independently H, halogen, the substituent X-L-Z as defined above, $C_1$-$C_{10}$ alkyl, $C_{10}$-$C_{20}$ alkyl, $C_1$-$C_{10}$ alkenyl, $C_1$-$C_{20}$ alkenyl, $C_1$-$C_{10}$ alkynyl, $C_{10}$-$C_{20}$ alkynyl, $C_1$-$C_{10}$ alkoxyl, $C_{10}$-$C_{20}$ alkoxyl, $C_3$-$C_{20}$ cyclic aliphatic moiety, aryl, heteroaryl, ether, thioether, amine, polyamine, polyether, or polythioether, each of which is optionally substituted; or, two of R°, together with the atoms to which they are attached, are connected to form a cycle, or heterocycle, each of which is optionally substituted; and
- $R^1$ and $R^2$ are independently absent, at least one lone pair of electrons, H, $C_1$-$C_{10}$ alkyl, $C_{10}$-$C_{20}$ alkyl, $C_1$-$C_{10}$ alkenyl, $C_{10}$-$C_{20}$ alkenyl, $C_1$-$C_{10}$ alkynyl, $C_{10}$-$C_{20}$ alkynyl, $C_3$-$C_{20}$ cyclic aliphatic moiety, aryl, heteroaryl, ether, thiol, thioether, amine, polyamine, polyether, polythioether, or polythiol, each of which is optionally substituted; or, one of $R^1$ or $R^2$, with one of R°, together with the atoms to which they are attached, are connected to form a cycle, or heterocycle, each of which is optionally substituted; wherein, when A is absent or non-aromatic, the dashed line represents an optional double bond; and/or
- when A is absent, each Y' is independently bonded to R° or X-L-Z, as defined above; or, the carbene precursor is a compound of formula IIa fused heteroaromatic ring system, an organometallic complex, a transition-metal catalyst, a metal-oxide catalyst, a simple sugar, a complex sugar, a carbohydrate, or a chemically derivatizable group, such as —OH, azide, carboxylic acid, carbonyl chloride, anhydride, ester, aldehyde, alcohol, amine, halogen, epoxide, thiirane, aziridine, amino acid, nucleic acid, alkene, alkyne, conjugated diene, thiol, alkyl thiol, or thioester, each of which is optionally substituted;

each Y or Y' is independently C or a heteroatom;

each R° is independently H, halogen, the substituent X-L-Z as defined above, $C_1$-$C_{10}$ alkyl, $C_{10}$-$C_{20}$ alkyl, $C_1$-$C_{10}$ alkenyl, $C_{10}$-$C_{20}$ alkenyl, $C_1$-$C_{10}$ alkynyl, or $C_{10}$-$C_{20}$ alkynyl, $C_1$-$C_{10}$ alkoxyl, $C_{10}$-$C_{20}$ alkoxyl, $C_3$-$C_{20}$ cyclic aliphatic moiety, aryl, heteroaryl, ether, thioether, amine, polyamine, polyether, or polythioether, each of which is optionally substituted; or, two of R°, together with the atoms to which they are attached, are connected to form a cycle, or heterocycle, each of which is optionally substituted; and $R^1$ and $R^2$ are independently absent, at least one lone pair of electrons, H, $C_1$-$C_{10}$ alkyl, $C_{10}$-$C_{20}$ alkyl, branched $C_1$-$C_{10}$ alkyl, $C_{10}$-$C_{20}$ alkenyl, $C_1$-$C_{10}$ alkynyl, or $C_{10}$-$C_{20}$ alkynyl), $C_3$-$C_{20}$ cyclic aliphatic moiety, aryl, heteroaryl, ether, thiol, thioether, amine, polyamine, polyether, polythioether, or polythiol, each of which is optionally substituted; or, one of $R^1$ or $R^2$, with one of R°, together with the atoms to which they are attached, are connected to form a cycle, or heterocycle, each of which is optionally substituted;

wherein, when A is absent or non-aromatic, the dashed line represents an optional double bond; and/or when A is absent, each Y' is independently bonded to R° or X-L-Z, as defined above; or, the carbene precursor is a compound of formula IIIa:

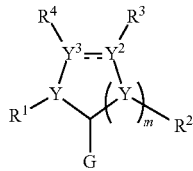

(IIIa)

wherein:

m is an integer from 0 to 4;

G is a perhalogenated alkyl, perhalogenated alkenyl, perhalogenated alkynyl, a perhalogenated aryl, or OR', wherein R' is an aliphatic group, for example, an alkyl group.

each Y or Y' is independently C or a heteroatom;

$Y^2$ and $Y^3$ are independently C or a heteroatom, and the dashed line represents an optional double bond;

$R^1$ and $R^2$ are independently absent, at least one lone pair of electrons, H, $C_1$-$C_{10}$ alkyl, $C_{10}$-$C_{20}$ alkyl, $C_1$-$C_{10}$ alkenyl, $C_{10}$-$C_{20}$ alkenyl, $C_1$-$C_{10}$ alkynyl, $C_{10}$-$C_{20}$ alkynyl, cycloalkyl, aryl, heteroaryl, ether, thiol, thioether, amine, polyamine, polyether, polythioether, or polythiol, each of which may be optionally substituted;

$R^3$ and $R^4$ are independently H, halogen, the substituent X-L-Z as defined for Formula III, $C_1$-$C_{10}$ alkyl, $C_{10}$-$C_{20}$ alkyl, branched $C_1$-$C_{10}$ alkyl, branched $C_{10}$-$C_{20}$ alkyl, $C_1$-$C_{10}$ alkenyl, $C_{10}$-$C_{20}$ alkenyl, $C_1$-$C_{10}$ alkynyl, $C_{10}$-$C_{20}$ alkynyl, $C_1$-$C_{10}$ alkoxyl, $C_{10}$-$C_{20}$ alkoxyl, $C_3$-$C_{20}$ cyclic aliphatic, aryl, heteroaryl, ether, thioether, amine, polyamine, polyether, or polythioether, each of which is optionally substituted; or, any one of $R^3$ or $R^4$, with any one of $R^1$ or $R^2$, together with the atoms to which they are attached, are connected to form a cycle, or heterocycle, each of which is optionally substituted.

In one example, the carbene precursor is as defined above, wherein $R^1$ and $R^2$ are independently methyl, ethyl, propyl, butyl, isopropyl, phenyl, mesityl, or diisopropylphenyl, each of which may be optionally substituted.

In an alternative embodiment, certain carbene monolayers are prepared by vapour depositing a carbene, or carbene precursor, as defined above, on a metal surface.

Carbene-functionalized composite materials are prepared from a material that comprises a metal surface. The material can be a solid metal, a metal film, a metal sheet or metal nanoparticles (pure or mixed metal). By way of further example, the metal surface can be on a metal film or layer on a support material, a surface of a metal particle or nanoparticle, a surface of a solid metal or a surface of a single crystal metal. A metal surface can comprise an alloy such as steel (including stainless steel), brass, bronze, tungsten carbide, calcium carbide, or any combination thereof. Alternatively, or in combination, a metal surface can comprise Fe, Rh, Ir, Ni, Pd, Pt, Cr, Cu, Ag, Au, W, or any combination thereof. In an example, in which a metal surface is a film or a layer on a solid support, the solid support can comprise, for example, mica, alumina, silica, titania, silicon, glass or indium tin oxide. Gold is used as an example metal in many of the studies described herein. It was chosen for surface studies since it does not react with $O_2$ to form an oxide and since it can be obtained as single crystals with clean surfaces. Other studies herein use palladium, copper, nickel and tungsten. Gold, palladium, nickel, copper and tungsten were used merely as examples of metals that can be coated with carbenes and are not meant to be limiting.

In certain embodiments, carbene-functionalized composite materials are prepared as described herein, using carbenes or carbene precursors that comprise one or more chemically derivatizable groups. Composite materials prepared using such carbenes or carbene precursors comprise a carbene monolayer that can be chemically modified by treatment of the chemically derivatizable groups, for example, to obtain desired composite material properties.

Carbene-functionalized composite materials of the present application are useful for, or can be configured for use in, various applications. In general, the process and materials described herein may be used to modify the properties of a metal surface of a material. For example, it may be desirable to modify a metal surface of a material by changing its surface properties (e.g., its surface wettability), by protecting the metal surface, by chemically activating or deactivating the metal surface to make it reactive or unreactive to a selected reagent or combination of reagents, or by displacing existing chemical groups or moieties from the metal surface (e.g., thio-containing compounds or groups). More specifically, the presently described process and materials can be used in the following, non-limiting, examples of applications:

making nano-patterns on semi-conducting surfaces;
fabricating electronic or microelectronic devices;
drug delivery;
electrochemically detecting molecules including biomolecules such as DNA, proteins, lipids or glucose, via, for example, non-specific adsorption;

surface plasmon resonance for detecting molecules, or specifically biomolecules such as DNA, proteins, lipids or glucose via, for example, non-specific adsorption;

making electrochemical sensors;

sensing applications;

colorimetric analysis of molecules, such as biomolecules; or protecting metal surfaces from, for example, oxidation or corrosion.

Described herein is a new method for functionalizing metal surfaces by forming a metal-carbon dative bond with carbenes, such as, but not limited to, N-heterocyclic carbene, which results in stable monolayer films that are chemically derivatizable. Although not wishing to be bound by theory, it has been suggested that the carbene-carbon's selection of a-top gold atoms means the resultant functionalized surfaces are characterized by a novel bonding mode and ligand class, and are more stable in air, solvents, and higher temperatures than the current metal-thiol systems (for example, in the gas phase Au—C is 557 kJ/mol, and Au—S is 295 kJ/mol).

One important factor to many technological applications, such as nano-patterned semiconducting surfaces, drug delivery, and biomolecule detection, is surface functionalization, wherein a single layer of molecules is chemically bound to a surface to change its physical and chemical properties. Thus, the herein described method of surface functionalization using modified carbenes was developed, which has been demonstrated on gold (FIGS. 1-4), palladium (FIG. 20), copper, tungsten and nickel (FIG. 19) and, may be applied to silver, palladium, and other metals. Various metal surfaces have been amenable to this functionalization, such as bulk metal, thin films, atomically ordered surfaces, and metal nanoparticles. Through the herein described method of surface functionalization, any functional group could be grafted to a metal surface to form a stable, uniform, single-molecular layers (also known as a self-assembled monolayer).

One method to functionalize gold, and to a lesser degree silver and copper, is to expose them to a solution of an alkanethiol [C. D. Bain, E. D. Troughton, Y.-T. Tao, J. Evall, G. M. Whitesides, R. G. Nuzzo, J. Am. Chem. Soc. 111, 321 (1989)]. The alkanethiol spontaneously forms a continuous, ordered, single-layer of the alkanethiol at the surface, attached to the metal via a metal-sulfur bond, resulting in a self-assembled monolayer (SAM). Alternatively, the alkanethiol may be deposited electrochemically on the surface. One described variant of this method is one in which either graphite or gold surfaces may be functionalized by electrochemical deposition of a diazonium salt, wherein a Au—C bond is formed [J. Pinson, et al. Chem. Soc. Rev. 34, 429, (2005)]. These functionalized surface films tend to be less ordered and less continuous than for alkanethiols, and tend to be more than one molecular layer thick. Reports make no comment on the stability of these films. Functionalization of gold nanoparticles via a Au—C bond using diazonium salts is limited by formation of a radical intermediate that reacts to form disordered and multilayer molecular films [L. Laurentius, et al. ACS Nano. 5, 4219 (2011)].

Other workers have successfully functionalized alkylidene species to molybdenum carbide (MoC) or ruthenium (Ru) surfaces [G. S. Tulevski, et al. Science 309, 591 (2005); G. A. Ozin, et al. Nanochemistry: A Chemical Approach to Nanomaterials, RSC Publishing, Cambridge, UK, (2005)]. In these cases, linkage was via a metal-carbon double bond.

Other technologies can be used to form SAMs on semiconductor, glass or metal oxide surfaces [G. S. Tulevski, et al. Science 309, 591 (2005)]. In some cases, a siloxane linkage (C—Si—O) is formed. However, such technologies are ineffective for functionalizing pure metal surfaces. Functionalizing pure metal surfaces has some advantages: it allows for binding of a ligand (or analyte) to be detected electrochemically. Gold is interesting because it is a biocompatible and relatively inert metal.

A limitation of using alkanethiols is that they can be unstable; they are expected to desorb from a bulk Au or thin Au film surfaces at temperatures of 70° C. or higher. They are particularly unstable in hydrophobic solvents at higher temperatures [C. D. Bain, et al. J. Am. Chem. Soc. 111, 321 (1989)], and they are known to begin decomposing in air at room temperature within a week. They can also be susceptible to exchange with amines or other thiol. This can pose a particular challenge if amino acid or protein species are to be bound to the surface and in in vivo biological systems where thiols abound. Thiol monolayers have been shown to begin decomposing by oxidation in air at room temperature after as little as 1-2 weeks [C. Vericat, et al. J. Phys. Condens. Matter 20, 184004 (2008); Y. Li, et al. J. Am. Chem. Soc., 114, 2428 (1992); M. H. Schoenfisch, et al. J. Am. Chem. Soc. 120, 4501 (1998); J. B. Schlenoff, et al. J. Am. Chem. Soc. 117, 12528 (1995)]. This limits the stability of such surfaces and thus the ability of thiol monolayers to protect surfaces. Furthermore, an Au—S bond can be a poor conductor where compared to certain Au—C bonding configurations [J. M. Seminario, et al. J. Am. Chem. Soc. 123, 5616 (2001)]; coupling a hydrocarbon-based compound to a metal via a carbon-metal bond, particularly one adjacent to a delocalised electronic system as is exhibited by the carbenes described herein, could be useful in maintaining a high conductivity at any metal/organic interface used in an electronic device.

In general, alkylidenes form stable monolayers on substrates that are good conductors (non-limiting examples include Ru or MoC). However, unlike gold, Ru and MoC are not materials that are routinely incorporated as part of the microelectronic fabrication industry. It is possible that alkylidenes will not form stable monolayers on Au, as compared to those formed with Ru or MoC, and thus use of alkylidenes may not be as straightforward as with N-heterocyclic carbenes, as described herein.

On MoC, the Mo=C double bond appears to be stable up to approximately 600° C. in vacuum. Stability of alkylidene monolayers on Ru under ambient conditions is similar to the gold carbene monolayers described herein. Alkylidenes are stable at room temperature in non-aqueous solvents. However, the gold carbene monolayers described herein are stable at higher temperatures in such solvents, and are also stable in boiling water for at least 24 hours. These are conditions that a SAM must be able to withstand if it were to act as a structural support for catalytic reactions on a surface. Alkylidene monolayers are primarily utilized as catalytic platforms for methathesis reactions, in which the carbon-meal bond itself takes part in the reaction. The herein described carbene monolayers on gold, by contrast, have been specifically designed to be unreactive; they can therefore act as a structural platform to support other functional groups that will be able to modify various properties of the metal surface, including its catalytic activity, and thus should support a much wider range of applications. In addition, the carbenes discussed herein are much more general in terms of the type of metal they bond to. The herein described carbene monolayers can be removed by various means. For example, to remove the herein described carbenes from a surface, they can be physically abraded, together with some or all of the underlying metal film, or exposed to strong oxidizing conditions such as, but not limited to, exposure to 3% $H_2O_2$ for 24 hours. Further, it has been shown that the herein described carbenes can be removed with heat (~190° C.) and decalin, or the like, as solvent.

With the method of surface functionalization described herein, it has been demonstrated that Au surfaces or nanoparticles can be functionalized by SAM formation through the displacement of surface thioethers. The resultant carbene-functionalized surface was found to be stable against incorporation of thiols or thioethers, as determined by XPS analyses that show no S on the surface (FIG. 1A-D). It was also demonstrated that Au surfaces or nanoparticles could be functionalized by displacement of surface thiols; some thiols, remained, however.

The stability of these carbene SAM-functionalized metal surfaces has been demonstrated. Carbenes bound to gold surfaces were resistant to exchange by sulfur ligands, indicating that the Au—C bond is more stable than the Au—S bond. The nanoparticles were stable for at least 15 weeks under ambient conditions, and surfaces were stable in non-aqueous solvents such as THF at temperatures of up to 70° C. for 24 hours. Surfaces modified by carbenes were stable after boiling in water in air for 24 hrs, they were stable to pH 2 and pH 12 at room temperature and 100° C., and, 85% of the film has been shown to survive overnight in 1% hydrogen peroxide (FIGS. 8-9).

The ability of these carbene monolayer-functionalized metal surfaces to adjust surface properties has been demonstrated by modifying the carbene backbone to impart hydrophobic or hydrophilic properties to a surface (FIG. 3). The ability to modify said carbene monolayers and affect surface properties can be relevant to sensing applications.

NHCs necessary to affect this surface functionalization are stable relative to other carbenes, which decompose, often violently, under non-cryogenic conditions or when exposed to a variety of simple chemicals. Comparatively, NHCs are stable enough to be bottled, crystallized, and even distilled. It has been shown that NHCs can be stored in a regular freezer, under nitrogen without any evidence of decomposition for upwards of four years.

Additionally, precursors of the herein described NHCs are stable under ambient conditions; conversion to the desired carbenes typically requires treatment with base and filtration. Resulting solutions can be used directly in the formation of self-assembled monolayers on metal. Monolayer formation has been shown to occur in just a few hours or less at room temperature by immersing the gold substrate in a solution of the desired carbene; thus, preparation of a stable monolayer on gold can be simple and readily accomplished.

While there have been a few studies of reactive carbenes (alkylidenes) on metal surfaces, which bind via a reactive metal-carbon double bond, [E. M. Zahidi, et al., *Nature* 409, 1023 (2001); G. S. Tulevski, et al., *Science* 309(5734), 591-594 (2005)] there have been few reports on the use of stable, bottleable NHC-type carbenes for the formation of single bonds to metal surfaces resulting in non-reactive surfaces.

In terms of NHC-type carbenes, there are two reports [T. Weidner et al., *Aust. J. Chem.* 64, 1177 (2011); A. V. Zhukhovitskiy, et al. *J. Am. Chem. Soc.* 135, 7418 (2013)]. In the more recent report, a NHC containing an appended reactive metal alkylidene was prepared on gold; however, only a 20% monolayer coverage was achieved and no stability or ordering was demonstrated. In the only other report of NHCs on flat Au surfaces, an ordered NHC film was inferred from NEXAFS C K-edge spectroscopy, but no stability studies were performed and no potential for derivatization illustrated. With respect to nanoparticles, examples of NHC-Au species have been described [J. Vignolle, et al. *Chem. Commun.* 7230 (2009); E. C. Hurst, et al. *New J. Chem.* 33, 1837 (2009); R. T. W. Huang, et al. *Dalton Trans.* 7121 (2009)]. In these reports, the stability of the functionalized surface was either determined to be low, to require aging via multiple dissolution/precipitation cycles, or was not largely assessed.

There are many applications envisioned for the herein described carbene-functionalized metal surfaces. One application in which SAMs on Au are used routinely on a commercial basis is surface plasmon resonance (SPR). In SPR, a thin Au film functionalized with an appropriate protein or antibody is used to detect biomolecules in solution: as analytes from solution are adsorbed onto a film, reflectance of the film changes, and the quantity of analyte adsorbed can be detected optically. Currently, thiol SAMs are used to functionalize Au films, which are subject to degradation. An N-heterocyclic carbene monolayer could substitute for the thiol, in principle forming a more stable film with a longer detector lifetime. Further, SPR detector chips have to be stored in a freezer under $N_2$ to preserve functionality, and have a shelf life of 6-12 months. Substitution of thiol SAMs with NHC SAMs can provide detectors that can be stored under ambient conditions, with longer shelf lives. It has been demonstrated, using NHC-16 on a Au film, that the NHC-functionalized metal surface will adsorb a lipid overlayer film, as measured using SPR, with stability and reproducibility greater than that of a commercially available alkanethiol-based Au film (Table 5 and FIGS. 15 and 16).

Functionalized gold nanoparticles have also demonstrated promise in the detection or analysis of molecules via colorimetric analysis [J. Liu, et al. *Agnew. Chem., Int. Ed.* 45, 90, (2006)]. Nanoparticles are functionalised with a DNA aptamer, which is designed to bind an analyte. Once bound, the nanoparticles aggregate, changing colour.

Opportunities exist in other applications that are less commercially developed, such as the use of functionalized Au nanoparticles for cancer treatment [B. Kang, et al. *J. Am. Chem. Soc.* 132, 1517, (2010)]. In this case, use of a more stable N-heterocyclic carbene functionalised surface may prolong shelf life of any drug compound formed. Coupling organic molecules to metals is also an important step in building novel electronic devices. The ability to form stable patterns on a surface could potentially be an important step in bottom-up approaches for the semiconductor industry [R. K. Smith, et al. *Prog. Surf. Sci.* 75, 1, (2004); Rahul Bhure, et al. *ACS Symposium Series*, Vol. 1054 Chapter 4 (2010); A. Kumar, et al. *Langmuir* 10, 1498 (1994)]. Further, the herein described carbene SAMs can be used to aid in selectively functionalizing materials containing both metal and non-metal surfaces. For example, the carbene-monolayer can be applied as a nano-scale protecting group, coating the metal surface to allow selective etching or functionalization of the non-metal surface, after which the carbene SAM can be selectively removed.

Envisioned applications include the use of carbene-functionalized surfaces in the field of supported catalysis, including electrocatalysis, wherein the carbene SAM on the metal surface is itself further functionalized with active metal catalysts. It has been demonstrated using, for example, NHC-10 on a gold film, that this compound will successfully catalyze the reproducible and repeatable decomposition of ceric ammonium nitrate in aqueous acidic solution, which may occur through water oxidation (FIG. 18A). In further embodiments, the carbene-functionalized surfaces can be employed to immobilized or bind catalysts useful for catalytic reactions, such as in H₂ production or CO oxidation. As would be readily within the skill of a worker skilled in the art, selection of the appropriate catalyst, such as a transition metal catalyst, will be based on the type of reaction to be catalyzed.

In a further embodiment, the composite materials described herein are electrochemically stable (C. M. Crudden, et al. *Nature Chem.* 6, 409-414 (2014), which is incorporated herein in its entirety).

To gain a better understanding of the invention described herein, the following working examples are set forth. It should be understood that these examples are for illustrative purposes only. Therefore, they should not limit the scope of this invention in any way. Examples of several NHCs having the above general formulas are provided herein. Stability test data is summarized in Table 3 of FIG. 23. Characterization data for NHC-coated Palladium is presented in Table 4. Synthetic information and characterization are provided in the Working Examples. A comparison of HPA sensor chips and NHC sensor chips is provided in Tables 5A and 5B. In addition, details of successful application of NHCs on metal surfaces are provided. For more information, see Crudden, C. M., Horton, J. H. et al. *Nature Chem.* 6(5): 409-414 (2014) including supplementary material.

WORKING EXAMPLES

Synthesis and deposition of carbenes were carried out in a nitrogen atmosphere in a glovebox (M. Braun) with oxygen and water levels≤2 ppm. Solvents were purified on a PureSolv Solvent Purification system, distilled, degassed and stored over 4 Å molecular sieves prior to use. Reactants were obtained from Aldrich Chemical Company (Oakville, Ontario, Canada) unless otherwise specified. Hydrogen tetrachloroaurate [HAuCl₄] was synthesized by the oxidation of gold metal through dissolution in aqua regia. Aqua regia was prepared as a mixture of concentrated nitric and hydrochloric acid (1:3 ratio v/v). Gold wire was dissolved in an appropriate volume of aqua regia solution such that no solid remained. Careful evaporation of the solution after 24 hours yielded chloroauric acid tetrahydrate as a yellow solid. Au(111) was purchased from Georg Albert PVD—Beschichtungen of Hauptstr, Germany. Polycrystalline gold refers to gold that was adhered to a silicon wafer (available from Western nanofabrication facility, University of Western Ontario, London, ON, Canada). The wafer was precoated with a chromium or titanium layer for improved adhesion.

$^1$H and $^{13}$C{$^1$H} Nuclear Magnetic Resonance (NMR) spectra were recorded on a BrukerAvance-400 or 500 MHz spectrometer (available from Milton, Ontario, Canada). Chemical shifts were reported in delta (δ) units, expressed in parts per million (ppm) downfield from tetramethylsilane using residual protonated solvent as an internal standard (C₆D₆, 7.15 ppm; CDCl₃, 7.24, CD₂Cl₂, 5.32 ppm). Chemical shifts were reported as above using solvent as an internal standard (C₆D₆, 128.0 ppm; CDCl₃, 77.23, CD₂Cl₂, 53.8 ppm). All 2D spectra (gs-COSY, gs-HSQC, gs-HMBC) were acquired in phase-sensitive mode. All data were acquired, processed, and displayed using Bruker XWinNMR and ACD Labs software and a standard pulse-sequence library. All measurements were carried out at 298 K unless otherwise stated.

Mass-spectrometry was carried out using a Micromass Platform LCZ 4000 system (available from Waters, Mississauga, Ontario, Canada). Elemental analyses were performed using Flash 2000 CHNS-O analyzer (available from Thermo Scientific). XPS measurements were performed using a Thermo Microlab 310F ultrahigh vacuum (UHV) surface analysis instrument (available from ThermoScientific) using Mg Kα X-rays (1253.6 eV) at 15 kV anode potential and 20 mA emission current with a surface/detector take off angle of 75°. The binding energy of all spectra was calibrated to the Au 4f line at 84.0 eV. A Shirley background subtraction algorithm was used as the background subtraction method for all peaks. The Powell peak-fitting algorithm was used, with peak areas normalized between different elements using the relative XPS sensitivity factors of Scofield [Scofield, J. H. Hartree-Slater subshell photoionization cross-sections at 1254 and 1487 eV. *J. Electron Spectrosc. Relat. Phenom.* 8, 129-137 (1976)]. In cases where absolute peak intensities for a single element were compared between different samples, a standard sample size and orientation with respect to X-ray source and detector within the analysis chamber were used. Calibration using Au thiol SAMs of known surface concentration showed that peak areas were reproducible within ±5% between sample runs.

Scanning tunnelling microscope (STM) measurements were performed in ultra-high vacuum at room temperature using a custom Pan-style STM. Mechanically-formed platinum-iridium tips were used for all experiments. GXSM [Zahl, P., et al. *J. Vac. Sci. Tech.* B 28, C4E39 (2010)] was used as control software using the Signal Ranger A810 DSP and Nanonis HVA4 high-voltage amplifier.

Example 1. Synthesis of N-Heterocyclic Carbenes

Example 1A. Synthesis of 1,3-Dihydro-1,3-bisisopropyl-2H-benzimidazol-2-ylidene, ("IPrBenz" or "NHC-1")

1,3-Diisopropyl-1H-benzo[d]imidazole-3-ium iodide (317 mg, 0.908 mmol) [Huynh, H. V., et al. *Organometallics* 25, 3267-3274 (2006)] was dissolved in 10 mL of anhydrous THF in a glove box. A solution of KOtBu (108 mg, 0.908 mmol) in THE (20 mL) was added dropwise over an hour. The reaction was stirred for an additional hour. The THF was then evaporated under vacuum, and the resulting residue was dissolved in toluene and filtered through Celite®. Evaporation of the filtrate gave the desired free carbene as a yellow oil in 68% yield. $^1$H NMR (C₆D₆) δ (ppm): 7.3-7.2 (br, 4H, PhH), 4.52 (sept, J$_{HH}$=6.6 Hz, 2H, CH—(CH₃)₃), 1.63 (d, J$_{HH}$=6.65 Hz, 12H, CH₃).

Example 1B. Synthesis of 2,4-Dihydro-2,4,5-triphenyl-3H-1,2,4-triazol-3-ylidene ("Enders Carbene" or "NHC-2"); 1,3-dihydro-1,3-bis(2,4,6-trimethylphenyl)-2H-imidazol-2-ylidene ("IMes" or NHC-3); 1,3-bis(2,4,6-trimethylphenyl)-2-imidazolidinylidene ("SIMes" or "NHC-4"); and 1,3-dihydro-1,3-bis(2,6-diisopropylphenyl)-2H-imidazol-2-ylidene ("IPr" or NHC-5)

These carbenes were prepared using a similar method as described in Enders, D., et al. *Angew. Chem. Int. Ed.* 34, 1021 (1995); Arduengo, A. J., et al. *J. Am. Chem. Soc.* 114, 5530 (1992); Arduengo, A. J., et al. *Tetrahedron* 55, 14523-14534(1999); and Jafarpour, J., et al. *J. Organomet. Chem.* 606, 49-54 (2000). Structural formulae are shown in Table 1. As a person of skill in the art will recognize, structural formula of free NHCs can be deduced by looking at a structural formula of an NHC on gold, and changing the bond that links the carbene carbon to the gold surface into the absence of a bond, with a lone pair of electrons on the carbene carbon.

Example 1C. Five Step Synthesis of 1,3-diisopropyl-5-(12-(azido)dodecyloxy)-1H-benzo[d]imidazole-2-ylidene, ("NHC-6")

(i) Synthesis of 4-(12-Bromododecyloxy)-2-nitroaniline

To a solution of 4-amino-3-nitrophenol (616 mg, 4 mmol) and 1,12-dibromo-dodecane (2.624 g, 8 mmol) in anhydrous acetonitrile (40 mL), potassium carbonate (552 mg, 4 mmol) was added. The mixture was stirred at 80° C. for 8 h under argon. The solvent was then evaporated and the crude product was separated by flash-chromatography using hexane-ethyl acetate gradient mixtures. Yield: 1.130 g (70%). Anal. Calc. for $C_{18}H_{29}BrN_2O_3$: C, 53.87; H, 7.28; N, 6.98. Found: C, 53.31; H, 7.12; N, 7.10. $^1H$ NMR (CDCl$_3$) δ (ppm): 7.54 (d, 1H, $J_{HH}$=2.7 Hz, ArH), 7.07 (dd, 1H, $J_{HH}$=9.0 Hz, $J_{HH}$=2.7 Hz, ArH), 6.76 (d, 1H, $J_{HH}$=9.1 Hz, ArH), 5.88 (s, 2H, NH$_2$), 3.92 (t, 2H, $J_{HH}$=6.5 Hz, 0-CH$_2$), 3.41 (t, 2H, $J_{HH}$=6.8 Hz, Br—CH$_2$), 1.86 (t, 2H, $J_{HH}$=7.3 Hz, $J_{HH}$=7.0 Hz), 1.77 (tt, 2H, $J_{HH}$=7.6 Hz, $J_{HH}$=6.6 Hz), 1.43 (m, br, 4H), 1.29 (m, br, 12H). $^{13}C\{^1H\}$ NMR (CDCl$_3$) S (ppm): 150.27 (s, $C_q$, CO—CH$_2$), 139.74 (s, $C_q$, C—NO$_2$), 131.54 (s, $C_q$, C—NH$_2$), 127.06 (s, Ar), 119.96 (s, Ar), 107.11 (s, Ar), 68.76 (s, CH$_2$—O), 34.04 (s), 32.80 (s), 29.47 (m), 29.39 (s), 29.30 (s), 29.07 (s), 28.72 (s), 28.14 (s), 25.94 (s).

(ii) Synthesis of 5-(12-Bromododecyloxy)-1H-benzo[d]imidazole

This synthetic procedure was adapted from Hanan, E. J., et al. *Synlett*, 2759-2764 (2010). Formic acid (25 mL) was added to a mixture of 4-(12-bromododecyloxy)-2-nitroaniline (2.005 g, 5 mmol), iron powder (2.790 g, 50 mmol), and ammonium chloride (2.670 g, 50 mmol) in isopropanol (35 mL). The resulting mixture was stirred at 80° C. for 3 h under argon, then cooled to room temperature and filtered. A resultant solid material was washed with isopropanol (3×5 mL). A resultant filtrate was evaporated to dryness and a residue was partitioned between saturated NaHCO$_3$ (20 mL) and CHCl$_3$ (20 mL). The water phase was additionally extracted with chloroform (3×20 mL). Combined non-aqueous layers were evaporated in vacuo to give a product that was used in the next step without further purification. Yield 1.735 g (91%). Anal. Calc. for $C_{19}H_{29}BrN_2O$: C, 59.84; H, 7.66; N, 7.35. Found: C, 58.07; H, 7.85; N, 7.34. ES-MS (m/z) for $C_{19}H_{29}N_2OBr$: 380.1475, Calc.: 380.1463. $^1H$ NMR (DMSO-d$_6$) δ (ppm): 8.14 (s, 1H, NH), 8.08 (s, 1H, N—CH=N), 7.44 (d, 1H, $J_{HH}$=8.8 Hz, ArH), 7.04 (s, 1H, ArH), 6.79 (d, 1H, $J_{HH}$=8.8 Hz, ArH), 3.95 (t, 2H, $J_{HH}$=6.3 Hz, 0-CH$_2$), 3.50 (t, 2H, $J_{HH}$=6.6 Hz, Br—CH$_2$), 1.77 (m, 2H), 1.71 (m, 2H), 1.42-1.33 (m, br, 4H), 1.25 (m, br, 12H). $^{13}C\{^1H\}$ NMR (CDCl$_3$) δ (ppm): 156.63 (s, N—CH=N), 139.71 (s, $C_q$), 136.37 (s, $C_q$), 131.18 (s, $C_q$), 116.11 (s, Ar), 114.07 (s, Ar), 97.96 (s, Ar), 68.69 (s, CH$_2$—O), 34.03 (s), 32.80 (s), 29.50 (m), 29.39 (s), 28.72 (s), 28.14 (s), 26.04 (s).

(iii) Synthesis of 5-(12-Azidododecyloxy)-1H-benzo[d]imidazole 5-(12-Bromododecyloxy)-1H-benzo[d]imidazole (381 mg, 1 mmol) was stirred with sodium azide (78 mg, 1.2 mmol) in DMSO (5 mL) for 4 h. The resultant mixture was poured into 25 mL of a saturated solution of NaHCO$_3$ in water and centrifuged. The desired product was extracted from precipitate with CHCl$_3$ (3×25 mL). Yield 237 mg (69%). ES-MS (m/z) for $C_{19}H_{29}N_5O$: 343.2387, Calc.: 343.2372. $^1H$ NMR (DMSO-d$_6$) δ (ppm): 8.06 (s, 1H, N—CH=N), 7.44 (d, 1H, $J_{HH}$=8.5 Hz, ArH), 7.05 (s, 1H, ArH), 6.78 (d, 1H, $J_{HH}$=7.9 Hz, ArH), 3.95 (t, 2H, $J_{HH}$=6.5 Hz, —O—CH$_2$), 3.28 (m, 2H, $J_{HH}$=6.8 Hz, N$_3$—CH$_2$), 1.70 (m, 2H), 1.50 (m, 2H), 1.41 (m, br, 2H), 1.23 (m, br, 14H). $^{13}C\{^1H\}$ NMR (CDCl$_3$) δ (ppm): 154.88 (s, N—CH=N), 141.39 (s, $C_q$), 137.78 (s, $C_q$), 133.45 (s, $C_q$), 116.27 (s, Ar), 111.75 (s, Ar), 98.19 (s, Ar), 67.89 (s, CH$_2$—O), 50.61 (s, CH$_2$—N$_3$), 28.98 (s), 28.89 (s), 28.78 (m), 28.50 (s), 28.21 (s), 26.11 (s), 25.58 (s).

(iv) Synthesis of 1,3-Diisopropyl-5-(12-(azido)dodecyloxy)-benzo[d]imidazolium iodide To a suspension of 5-(12-azidododecyloxy)-1H-benzo[d]imidazole (34.4 mg, 0.1 mmol) and Cs$_2$CO$_3$ (39 mg, 0.11 mmol) in acetonitrile (4 mL), 2-iodopropane (250 μL, 2.5 mmol) was slowly added. The mixture was stirred at 90° C. in a sealed pressure tube under a nitrogen atmosphere for 24 h. The excess of 2-iodopropane, solvent and volatiles were evaporated in vacuo. The resulting oil was triturated with diethyl ether (2 mL) to give the desired product as a gray powder. Yield 36 mg (65%). ES-MS (m/z) for $C_{25}H_{42}N_5O$: 428.3397, Calc.: 428.3389. $^1H$ NMR (CDCl$_3$) δ (ppm): 10.67 (s, 1H, N—CH=N), 7.65 (d, 1H, $J_{HH}$=9.2 Hz, ArH), 7.22 (d, 1H, $J_{HH}$=9.3 Hz, ArH), 7.11 (s, 1H, ArH), 5.12 (sept, $J_{HH}$=6.6 Hz, 2H, CH—(CH$_3$)$_3$), 4.06 (t, 2H, $J_{HH}$=6.1 Hz, O—CH$_2$), 3.24 (t, 2H, $J_{HH}$=6.6 Hz, N$_3$—CH$_2$), 1.84 (m, 12H), 1.59 (m, 2H), 1.49 (m, 2H), 1.28 (m, br, 16H). $^{13}C\{^1H\}$ NMR (CDCl$_3$) δ (ppm): 158.76 (s, $C_q$), 138.52 (s, N—CH=N), 132.01 (s, $C_q$), 124.70 (s, $C_q$), 117.29 (s, Ar), 114.46 (s, Ar), 96.62 (s, Ar), 69.30 (s, CH$_2$—O), 52.37 (s, CH$_3$—CH—CH$_3$), 51.94 (s, CH$_3$—CH—CH$_3$), 51.41 (S, CH$_2$—N$_3$), 29.43 (s), 29.27 (s), 29.04 (s), 28.97 (s), 28.74 (s), 26.61 (s), 25.91 (s), 22.26 (s, CH$_3$), 22.18 (S, CH$_3$).

(v) Synthesis of 1,3-Diisopropyl-5-(12-(azido)dodecyloxy)-1H-benzo[d]imidazole-2-ylidene, ("NHC-6")

Free carbene was obtained by dissolving 1,3-diisopropyl-5-(12-(azido)dodecyloxy)-benzo[d]imidazolium iodide (5.5 mg, 0.01 mmol) in 2 mL of anhydrous THF in a round bottomed flask with stirring in a glove box. Separately, a basic solution was prepared of KO$^t$Bu (1.1 mg, 0.01 mmol) dissolved in 0.7 mL of anhydrous THF. Both solutions were cooled to −40° C. The basic solution was then added dropwise over 30 min. The reaction was stirred for an additional hour. THE was then evaporated in vacuo, and a resulting solid was dissolved in toluene and filtered through Celite® and used directly for surface functionalization.

Example 1D. Four Step Synthesis of 5-(dodecyloxy)-1,3-diisopropyl-1H-benzo[d]imidazol-3-ium Hydrogen Carbonate (NHC-1 Hydrogen Carbonate Salt)

(i) 4-(dodecyloxy)-2-nitroaniline

To a solution of 4-amino-3-nitrophenol (1.540 g, 10 mmol) and 1-bromododecane (2.739 g, 2.633 mL, 11 mmol) in anhydrous acetonitrile (50 mL), potassium carbonate (1.380 g, 10 mmol) was added. The mixture was stirred at 80° C. for 8 h under argon. Then the solvent was evaporated and crude product was separated by flash-chromatography using hexane-ethylacetate gradient mixtures. Yield: 2.444 g (76%). Anal. Calc. for $C_{18}H_{30}N_2O_3$: C, 67.05; H, 9.38; N, 8.69. Found: C, 66.44; H, 9.42; N, 8.61. TOF MS (m/z) for $C_{18}H_{30}N_2O_3$: 322.2247, Calc.: 322.2256 $^1$H NMR (CDCl$_3$): δ 7.35 (d, 1H, $J_{HH}$=2.8), 7.23 (s, 2H, NH$_2$), 7.13 (dd, 1H, $J_{HH}$=9.3, $J_{HH}$=2.8), 6.97 (d, 1H, $J_{HH}$=9.3), 3.89 (t, 2H, $J_{HH}$=6.6, —O—CH$_2$—), 1.67 (tt, 2H, $J_{HH}$=6.8), 1.38 (m, 2H), 1.24 (m, 16H), 0.85 (t, 3H, $J_{HH}$=6.8). $^{13}$C{$^1$H} NMR (CDCl$_3$): δ 148.99 (s, C$_q$, >CO—CH$_2$—), 142.29 (s, Co, >C—NH$_2$), 129.59 (s, C$_q$, >C—NO$_2$), 127.90 (s, C$_{Ar}$), 121.15 (s, C$_{Ar}$), 106.28 (s, C$_{Ar}$), 68.50 (s, —CH$_2$—O), 31.75, 29.4, 29.45, 29.41, 29.17, 29.15, 29.00, 25.89, 22.54, 14.38.

(ii) 5-(dodecyloxy)-1H-benzo[d]imidazole

Formic acid (35 mL) was added to a mixture of 4-(dodecyloxy)-2-nitroaniline (2.257 g, 7 mmol), iron powder (3.906 g, 70 mmol), and ammonium chloride (3.738 g, 70 mmol) in isopropyl alcohol (49 mL). Resulting mixture was stirred at 80° C. for 3 h, then cooled to room temperature and filtered off. Solid phase on the filter was washed by isopropyl alcohol (3×5 mL). Filtrate was evaporated to dryness and 30 mL of saturated sodium bicarbonate solution was added (foamy). Then sodium bicarbonate (powder) was added portion-wise until pH 6 was reached. Then the suspension was extracted by chloroform (5×30 mL). Combined non-aqueous layers were dried over anhydrous magnesium sulfate, and evaporated to give 1.715 g of product. Yield 81%. Anal. Calc. for $C_{19}H_{30}N_2O$: C, 75.45; H, 10.00; N, 9.26. Found: C, 75.09; H, 10.03; N, 9.08. TOF MS (m/z) for $C_{19}H_{30}N_2O$: 302.2348, Calc.: 302.2358. $^1$H NMR (CDCl$_3$): δ 8.00 (s, 1H), 7.55 (d, 1H, $J_{HH}$=8.6), 7.09 (s, 1H), 6.95 (d, 1H, $J_{HH}$=7.4), 3.89 (t, 2H, $J_{HH}$=6.5, —O—CH$_2$—), 1.81 (tt, 2H, $J_{HH}$=7.3), 1.46 (m, 2H), 1.35 (m, 2H), 1.27 (m, 14H), 0.89 (t, 3H, $J_{HH}$=6.9). $^{13}$C{$^1$H} NMR (CDCl$_3$): δ 155.84 (s, C$_q$, >CO—CH$_2$—), 140.34 (s, C$_{Ar}$, N=CH—NH), 133.64 (s, C$_q$), 130.76 (s, CO$_q$), 116.32 (s, C$_{Ar}$), 112.64 (s, C$_{Ar}$), 97.86 (s, C$_{Ar}$), 68.52 (s, 1C, —CH$_2$—O—), 31.74, 29.44, 29.27, 29.17, 25.96, 22.49, 13.88.

(iii) 5-(dodecyloxy)-1,3-diisopropyl-1H-benzo[d]imidazol-3-ium iodide

To a suspension of 5-(dodecyloxy)-1H-benzo[d]imidazole (302.4 mg, 1 mmol) and Cs$_2$CO$_3$ (325.8 mg, 1 mmol) in acetonitrile (50 ml), 2-iodopropane (4.25 g, 2.5 mL, 25 mmol) was slowly added. The mixture was stirring at 90° C. in a flask with reflux condenser under nitrogen atmosphere for 24 h. Then the excess of 2-iodopropane, solvent and volatile sub-products were evaporated under vacuum. The residual solid was triturated and sonicated in diethyl ether (2×4 mL), which was then decanted off. Subsequent drying under vacuum afforded the desired product as an off-white powder (342 mg, 66% yield). Anal. Calc. for $C_{25}H_{43}N_2OI$: C, 58.36; H, 8.42; N, 5.44. Found: C, 56.80; H, 8.39; N, 5.52. TOF MS (m/z) for $C_{25}H_{43}N_2O$: 387.3389, Calc.: 387.3375. $^1$H NMR (CDCl$_3$): δ 10.59 (s, 1H, N—CH=N), 7.67 (d, 1H, $J_{HH}$=9.0), 7.21 (d, 1H, $J_{HH}$=9.0), 7.13 (s, 1H), 5.15 (sept, $J_{HH}$=6.8, 2H, CH—(CH$_3$)$_2$), 4.06 (t, 2H, $J_{HH}$=6.3, —O—CH$_2$—), 1.84 (tt, 12H, $J_{HH}$=6.5, CH—(CH$_3$)$_2$), 1.82 (m, br, 2H), 1.25 (m, 16H), 0.86 (t, 3H, $J_{HH}$=6.6). $^{13}$C{$^1$H} NMR (CDCl$_3$): δ 158.88 (s, CO$_q$, >CO—CH$_2$—), 138.45 (S, C$_{Ar}$, N=CH—NH), 132.10 (s, CO$_q$), 124.79 (S, CO$_q$), 117.41 (S, C$_{Ar}$), 114.58 (S, C$_{Ar}$), 96.79 (s, C$_{Ar}$), 69.45 (s, 1C, —CH$_2$—O—), 52.42 (s, CH—(CH$_3$)$_2$), 52.0 (S, CH—(CH$_3$)$_2$), 31.88, 29.62, 29.59, 29.55, 29.51, 29.34, 29.30, 29.03, 25.98, 22.64, 22.35 (s, CH—(CH$_3$)$_2$), 22.27 (s, CH—(CH$_3$)$_2$), 14.06 (s. CH$_3$).

(iv) 5-(dodecyloxy)-1,3-diisopropyl-1H-benzo[d]imidazol-3-ium Hydrogen Carbonate A mixture of 5-(dodecyloxy)-1,3-diisopropyl-1H-benzo[d]imidazol-3-ium iodide (257.1 mg, 0.5 mmol) and dry KHCO3 (55.0 mg, 0.55 mmol) in anhydrous MeOH (12 mL) was stirred at room temperature for 48 h. The resulting yellow solution was filtered, and its filtrate was evaporated to dryness under vacuum. The residue was extracted with dichloromethane (6 mL), and the solution was filtered through a Celite® pad. Evaporation to dryness of the filtrate gave the product as a yellowish solid (203 mg, 90%). Time-of-flight mass spectrometry ("TOF MS") (m/z) for $C_{25}H_{43}N_2O$: 387.3389, Calc.: 387.3375. $^1$H NMR (CDCl$_3$): δ 10.74 (s, 1H, N—CH=N), 7.65 (d, 1H, $J_{HH}$=9.0), 7.22 (d, 1H, $J_{HH}$=9.0), 7.10 (s, 1H), 5.15 (sept, $J_{HH}$=6.8, 2H, CH—(CH$_3$)$_2$), 4.06 (t, 2H, $J_{HH}$=6.3, —O—CH$_2$—), 1.84 (m, 12H, CH—(CH$_3$)$_2$), 1.81 (m, br, 2H), 1.49 (tt, 2H, $J_{HH}$=7.4), 1.37 (tt, 2H, $J_{HH}$=7.5), 1.26 (m, 14H), 0.88 (t, 3H, $J_{HH}$=6.6). $^{13}$C{$^1$H} NMR (CDCl$_3$): δ 158.79 (s, C$_q$, >CO—CH$_2$—), 138.71 (s, C$_{Ar}$, N=CH—NH), 132.04 (s, C$_q$), 124.74 (s, C$_q$), 117.28 (s, C$_{Ar}$), 114.47 (s, C$_{Ar}$), 96.69 (s, C$_{Ar}$), 69.34 (s, 1C, —CH$_2$—O—), 52.43 (s, CH—(CH$_3$)$_2$), 52.0 (s, CH—(CH$_3$)$_2$), 31.85, 29.60, 29.58, 29.53, 29.31, 29.29, 28.99, 25.95, 22.62, 22.28 (s, CH—(CH$_3$)$_2$), 22.20 (s, CH—(CH$_3$)$_2$), 14.05 (s. CH$_3$).

Example 1E. General Experimental Protocol for Benizimidazole Carbonate Synthesis

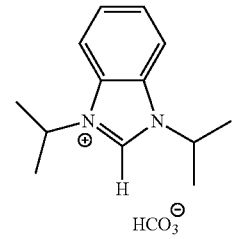

Preparation of [iPr$_2$BIMY(H)][HCO$_3$] ("Carbonate Salt of NHC-1"):

A similar procedure to Taton, Fèvre, M., et al. J. Am. Chem. Soc. 2012, 134 (15), 6776-6784 and Fèvre, M., et al. J. Org. Chem. 2012, 77 (22), 10135-10144 was followed. 1,3-Diisopropyl-1H-benzo[d]imidazol-3-ium iodide (258 mg, 0.781 mmol) and KHCO$_3$ (86.1 mg, 0.859 mmol) were dried for several hours under vacuum at room temperature. 5 mL of dry methanol was added under argon and this was stirred for 48 hours at room temperature. The methanol was removed in vacuo and 5 mL of dichloromethane was added. This suspension was filtered through Celite®, the resulting filtrate was evaporated under vacuum. A resulting powder was washed with hexanes to yield an off-white powder (99+% yield). The above procedure was used to prepare carbonate salts of other NHCs.

As will be recognized by a person of ordinary skill in the art of the invention, $^1$H NMR and $^{13}$C NMR characterization data for a carbonate salt of an NHC is substantially identical to the characterization data of the corresponding NHC's iodo salt from which it was prepared. For this reason, mass spectroscopy was used to show that the carbonate salt was obtained. Representative characterization data is provided below for the carbonate salt of NHC-1.

Carbonate salt of NHC-1 also known as [Pr$_2$BIMY(H)][HCO$_3$]: $^1$H NMR (600 MHz, Methanol-d$_4$) δ 1.74 (d, 12H, (CH$_3$)$_2$, J=6.7 Hz), 5.10 (m, CH(CH$_3$)$_2$), 7.71 (dd, J=3.1 Hz, 6.3 Hz, 2H, Hbenz), 8.04 (m, J=2.5 Hz, 5.7 Hz, 2H, Hbenz), 9.63 (br, 1H, N$_2$CH). HCO$_3$-proton could not be observed due to rapid exchange with the deuterated solvent on the NMR time scale, N$_2$CH could be detected as broad signal from the same reasons. $^{13}$C NMR (150.8 MHz, Methanol-d$_4$) δ 21.1, 51.4, 113.6, 126.2, 132.9. High Resolution Mass Spectrometry: Positive mode: calc for [C$_{13}$H$_{19}$N$_2$]$^+$ [M]$^+$ 203.1543, found 203.1532; negative mode: calc for [HCO$_3$]$^-$ 60.9931; found 60.9939.

Example 1F. Synthesis of 1,3-Dimethylbenzimidazolium Hydrogen Carbonate, [Me$_2$BIMY(H)][HCO$_3$], NHC-17

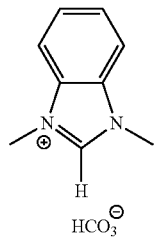

1,3-dimethylbenzimidazolium iodide [Rodriguez-Castillo, M. et al., *Dalton Trans*. 2014, 43, 5978-5982] (200 mg, 0.730 mmol) and KHCO$_3$ (76.71 mg, 0.766 mmol) were dried for several hours under vacuum at room temperature. Dry methanol (5 mL) was added under argon and a resultant mixture was stirred for 48 hours at room temperature. The mixture's volume was removed in vacuo and dichloromethane (5 mL) was added to form a suspension. This suspension was filtered through CELITE® and a filtrate was collected. The filtrate's volume was reduced under vacuum and a resulting powder was obtained. The powder was washed with hexanes and an off-white powder was collected by filtration (NHC-17, 112.5 mg, 74%). $^1$H NMR (400 MHz, methanol-d$_4$) δ 9.48 (br, 1H, N$_2$CH), 7.97 (dd, J=6.3, 3.1 Hz, 1H, CH$_{Ar}$), 7.73 (dd, J=6.3, 3.1 Hz, 1H, CH$_{Ar}$), 4.17 (s, 3H, CH$_3$). $^{13}$C NMR (100 MHz, methanol-d$_4$) δ 133.47 (C$_q$), 128.11 (CH$_{Ar}$), 114.23 (CH$_{Ar}$), 34.03 (CH$_3$). The HCO$_3^-$'s proton and carbon could not be observed due to rapid exchange with the deuterated solvent. HRMS (ESI): Positive mode: calcd. for [C$_{11}$H$_{15}$N$_2$]$^+$ 147.0917, found 147.0910; negative mode: calcd. for [CO$_3$]$^-$ 59.9847, found 59.9861. XPS: N:C ratio found 2:10; N:C ratio expected 2:9.

Example 2. Deposition of Carbenes on Gold Surfaces

Self-assembled monolayers were prepared by immersion of gold substrates in a 1 mM solution of a NHC-carbene in anhydrous toluene, for 4 h at room temperature in a glove box. Substrates then were rinsed in anhydrous THF (5×2 mL) and dried under a nitrogen gas stream.

To test NHCs' ability to form stable monolayers, Au(111) films on mica and thioether-protected gold nanoparticles were treated with representative NHCs: NHC-1, NHC-2, NHC-3, NHC-4, NHC-5A, NHC-5B, NHC-6, NHC-7, NHC-8, NHC-9, NHC-10, NHC-11, NHC-13, NHC-14, NHC-15, NHC-16, NHC-17, and NHC-18 (see Table 1 for structural formulae).

Each carbene was found to react with Au surfaces after simple room temperature immersion of Au(111) or Au nanoparticles in a solution of the carbene or the corresponding carbonate salt in an appropriate solvent. Despite considerable variety in structure, C/N ratios, as determined by X-ray photoelectron spectroscopy (XPS), were in agreement with the representative NHCs within error, indicating clean reaction with the surface (see Table 2A and 2B). Scanning tunneling microscopy (STM) was also used to analyze selected films (FIGS. 2B and 5).

Figure 1A:
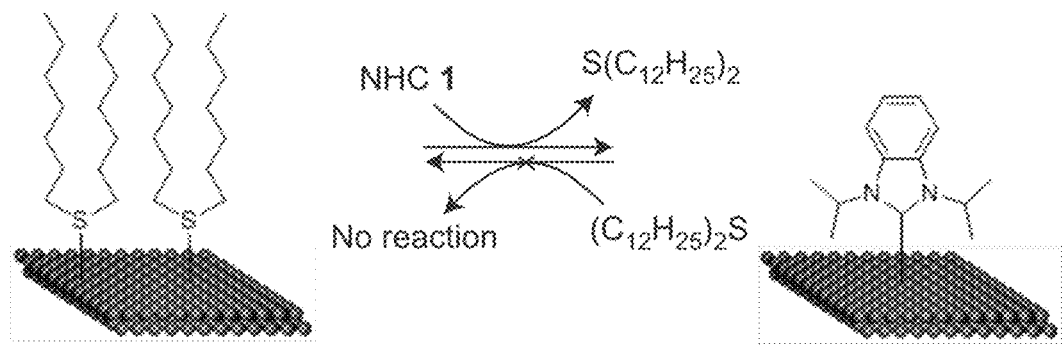
FIG. 1A depicts reaction of free carbene NHC-1 (see Table 1) with dodecylsulfide-protected Au surfaces, which resulted in displacement of sulfide. Once formed, NHC-protected surfaces did not show incorporation of sulfur upon treatment with dodecyl sulfide or dodecanethiol under the conditions specified as determined by XPS analysis.
Figure 1B:
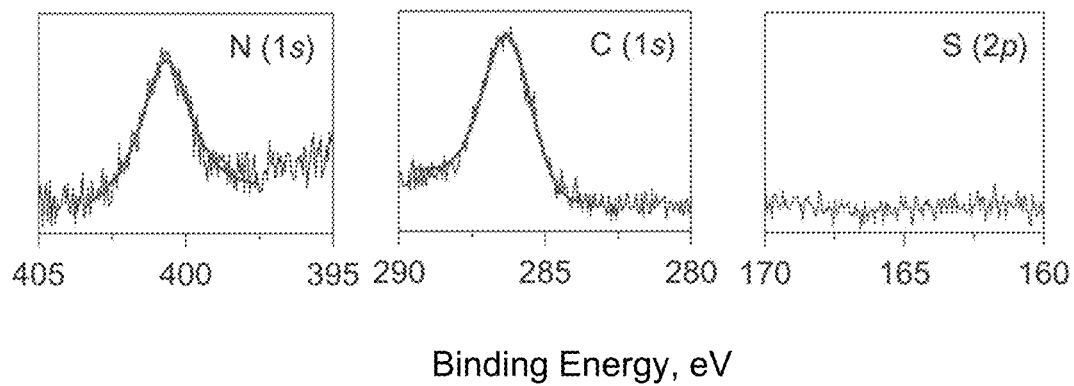
FIG. 1B depicts N(1s), C(1s) and S(2p) XPS spectra of the product of the forward direction reaction shown in FIG. 1A ($Au_{NP}$(NHC-1)). Loss of dodecylsulfide is demonstrated by a lack of S(2p) signal.
Figure 1C:
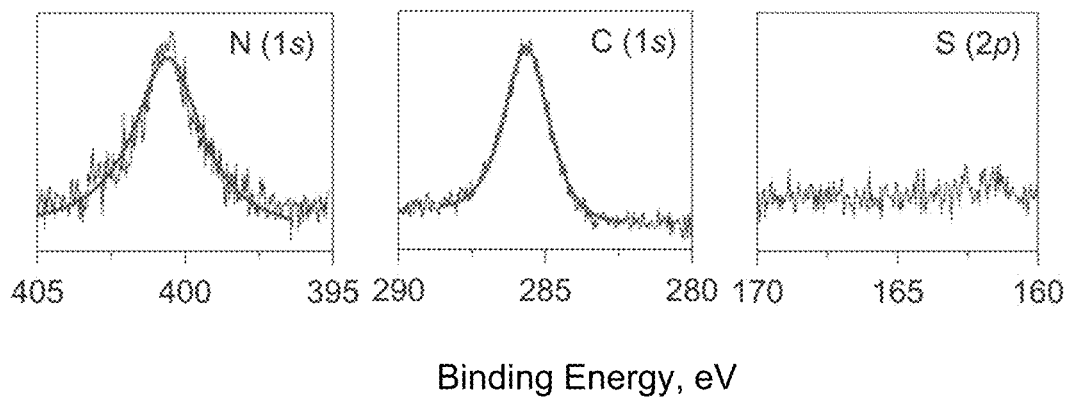
FIGS. 1C and 1D depict XPS spectra of the product of $Au_{NP}$(NHC-1) (FIG. 1C) and Au(111)(NHC-1) (FIG. 1D) exposed to $S(C_{12}H_{25})_2$ as shown in the reverse reaction in FIG. 1A. In both cases, lack of incorporation of dodecylsulfide is demonstrated by the absence of S(2p) signal, while retention of the NHC is demonstrated by the expected N(1s)/C(1s) area ratio.
Figure 1D:
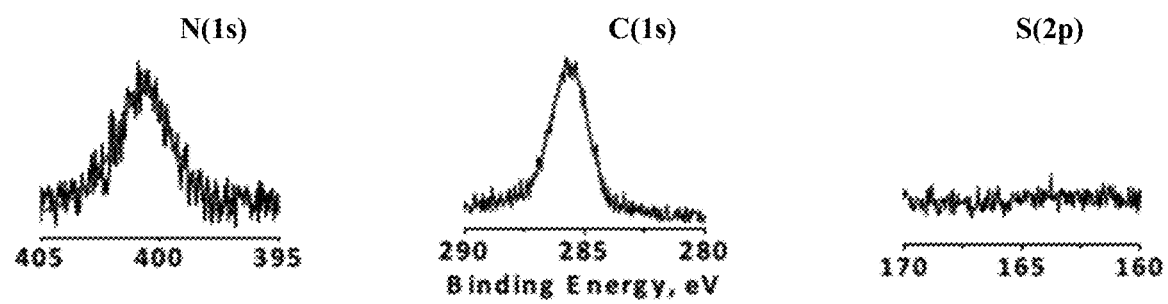

XPS data showed complete removal of dodecylsulfide from the surface of gold nanoparticle surfaces upon treatment with a 1 mM solution of a NHC in toluene at room temperature for as little as 4 h (see FIGS. 1A and 1B). XPS spectra obtained after reacting NHC 1 (IPrBenz) with gold nanoparticles protected with dodecylsulfide showed that no S(2p) XPS signal was observed, indicating complete displacement of dodecylsulfide by NHC-1 within an XPS' limits of detection (FIG. 1C). Similarly, once NHC-protected Au nanoparticles were formed, treatment with dodecyl sulfide resulted in no incorporation of sulfur within the limits of detection. Thiols such as dodecanethiol were also incapable of removing representative carbenes from NHC-terminated Au(111). After treating NHC-1-protected Au(111) surfaces with a 1 mM solution of dodecanethiol for 24 h at room temperature, no sulfur was detected by XPS (FIG. 2E).

Although dodecyl sulfide was completely removed upon treatment with NHCs, gold surfaces initially functionalized with dodecanethiol were more resistant to displacement by NHC. Only a 60% loss in the S(2p) signal was observed following 24 h exposure of dodecanethiol protected Au(111) surfaces to a solution of NHC-1 or NHC-3 (FIGS. 3D and 3E). Concomitant with the decreased S(2p) signal, an N(1s) signal appeared, which indicated that NHCs were deposited on the Au surface, but complete thiol-displacement was not achieved under the same conditions as the dialkylsulfides. Without wishing to be bound by theory, lowered steric bulk of the thiol vs. sulfide and the specific bonding mode of the thiol compared to the carbene, as described below, were considered potentially responsible for this phenomenon.

Example 3. Studies of pH Stability Tests

Since stability in thiol-based SAMs was closely related to ordering [C. Vericat, M. E. Vela, G. Benitez, P. Carro, R. C. Salvarezza, *Chem. Soc. Rev.* 39, 1805 (2010)], and NHC-1-based films displayed molecular level ordering, the stability of these films was explored. SAMs formed from NHC-1 showed no change by XPS after heating in boiling solvent (e.g., THF) for 24 hours. For stability test results see FIG. 2C and Table 3. SAMs of NHC-1 also showed no discernible change upon heating in boiling water for 24 hours in air, demonstrating thermal and oxidative stability. A large fraction of the surface even remained upon treatment with 1% H$_2$O$_2$ for 24 h. Although decomposition was observed at 3% H$_2$O$_2$ (see FIG. 8), the fact that 80±5% of the film survived treatment with 1% H$_2$O$_2$ for 24 h was notable and would not be possible with thiol-based SAMs. Films of NHC-1 were also completely stable in aqueous solutions ranging from pH 2 to 12 for 24 h (see FIG. 9 and Table 3 of FIG. 23).

When the bulkier carbene 3 was employed to generate a SAM, complete stability to boiling THF (66° C.) was still observed (FIG. 2D), however greater than 50% loss of the film was observed in boiling water (FIG. 2D). These observations were consistent with the higher ordering of NHC-1-based films seen in the STM images. Similar to regular alkyl thiol-based SAMs, where stability was provided by both gold thiolate bonds and van der Waals interactions between the alkyl groups [R. G. Nuzzo, et al. *J. Am. Chem. Soc.* 105, 4481 (1983); B. D. Gates, et al. *Chem. Rev.* 105, 1171 (2005); J. C. Love, et al. *Chem. Rev.*, 105, 1103 (2005); U. Drechsler, et al. *Chem.—Eur. J.* 10, 5570 (2004); C. D. Bain, et al. *J. Am. Chem. Soc.* 111, 321 (1989)], the ability to stack provided enhanced stability for benzimidazole-based SAMs based on NHC-1. In addition, the smaller isopropyl wing-tip substituents of NHC-1 compared to the mesityl substituents on NHC-3 likely provided for greater packing density on the surface.

NHC-1-functionalized gold surfaces were submerged in freshly prepared unbuffered solutions of certain pHs for 24 h. Experiments were conducted under $N_2$ gas to minimize the possibility of pH change due to adsorption of atmospheric $CO_2$. After this time, functionalized surfaces were rinsed in deionized water (3×2 mL) and dried in an $N_2$ gas stream. pH values were adjusted using NaOH and HCl solutions. Unbuffered solutions were employed in order to avoid potential adsorption effects of buffer ions from solution. Ionic strength of all solutions was maintained at $10^{-3}$ M for all solutions, except those under the extreme pH 2 and 12 regimes. See Table 3 of FIG. 23 for a summary of the results of these stability tests.

Example 4. Deposition of Carbenes from Carbene Precursors on Gold Surfaces

Example 4A. Initial Studies

Bis(mesityl)immidazolium salt (IMesHCO$_3$) was prepared in 52% yield by following a reported literature procedure [Taton, D., et al. *J. Am. Chem. Soc.* 2012, 134, 6776.] Three different IMesHCO$_3$-gold deposition methods were investigated: (1) IMesHCO$_3$ (4 mg) was dissolved in wet methanol under air and a gold slide was completely submerged into the methanolic solution. Reaction was left under Argon for 48 h at room temperature. The gold slide was then washed with 4 mL of methanol, dried under air and XPS data were recorded; (2) IMesHCO$_3$ (2 mg) was dissolved in dry methanol under air atmosphere and a gold slide was completely submerged into the methanolic solution. Reaction was left under argon for 48 h at room temperature. The gold slide was then washed 15 times×4 mL of methanol dried under air and XPS data were recorded; (3) IMesHCO$_3$ (2 mg) was dissolved in dry methanol under argon (using a Schlenk line) and a gold slide was completely submerged into the methanolic solution. Reaction was left under argon for 48 h at room temperature. The gold slide was then washed 15 times×4 mL of methanol dried under air and XPS data were recorded. XPS spectra clearly showed deposition of NHC-3 carbene on all three gold surfaces and no difference in signal intensity was observed for all experiments (see FIG. 15).

Example 4B. Studies of Carbene Precursors Including Carbonate Salts of Various NHCs Studies have been conducted of carbene precursor compounds such as, for example, carbonate salt of benzimidazole and several of its derivatives. Carbonate salts of NHCs offer an improved means of forming carbene self-assembled monolayers on a metal surface, since carbonate salts and solutions of carbonate salts are air stable. Furthermore, carbonate salts of NHCs enable deposition that can take place in solvents that have not undergone any special treatment to exclude water or oxygen. Therefore, a carbene monolayer precursor (e.g., carbonate salts of NHCs) can be stored under ambient conditions, and no special conditions (such as exclusion of water or oxygen) are required to prepare a carbene self-assembled monolayer. This is an improvement over simple carbenes, which must be stored under an oxygen-reduced atmosphere (e.g., in a glovebox) and reacted with a dry surface under anaerobic conditions.

Resulting carbene self-assembled monolayers on Au prepared using carbonate salts of NHCs exhibited identical XPS spectra and stability towards extremes of pH, solvent and oxidizing agents ($H_2O_2$) as self-assembled monolayers prepared from NHCs.

Self-assembled monolayers were prepared by immersion of the gold substrates in solutions of the corresponding hydrogen carbonate precursor (up to 2 mM) in methanol for up to 24 h at room temperature. Substrates then were rinsed in methanol (5×2 mL) and dried under a nitrogen gas stream.

Example 5. Nanoparticles Studies

Example 5A. Preparation of Gold Nanoparticles

Chloroauric acid tetrahydrate 52 mg, 0.126 mmol of in water (5.1 mL) was added to a solution of tetraoctylammonium bromide (167 mg, 0.306 mmol) in toluene (3.06 mL). The resulting mixture was stirred vigorously until the aqueous layer became colourless. Following this, a solution of dodecyl sulfide (170 mg, 0.459 mmol) in toluene (11.5 mL) was added and allowed to stir for another 5 minutes. A solution of sodium borohydride (69.5 mg, 1.837 mmol) in water (18 mL) was added in one aliquot to the mixture while stirring. A fast colour change from red-orange to dark purple-brown was observed, indicating colloid formation. The solution was allowed to stir for another hour before a non-aqueous layer was separated and reduced to a minimum amount through rotary evaporation at room temperature (to prevent nanoparticle decomposition). The colloids were then suspended in anhydrous ethanol and left at room temperature overnight to precipitate. The resulting solution was then centrifuged (2500 rpm, 1 hour), decanted and dried in vacuo. The nanoparticles were then suspended in ethanol (3×10 mL), centrifuged, dried and stored at −40° C. in solid form.

Example 5B. Studies of Dodecyl Sulfide Exchange by NHCs in Gold Nanoparticle

Gold nanoparticles stabilized by dodecyl sulfide (3 mg) were dissolved in anhydrous toluene (5 mL) under an inert atmosphere in a glove box and then a 20-fold molar excess of carbene relative to gold was added. This mixture was allowed to react overnight at room temperature. Nanoparticles (except NHC-1 stabilized) were collected by centrifugation, washed with toluene (3×0.5 mL) and dried in vacuo. NHC-1 stabilized nanoparticles in toluene were mixed with hexane (2 mL) collected by centrifugation, washed with hexane (3×0.5 mL), centrifuged, and dried in vacuo.

Example 5C. Studies of NHCs in Palladium Nanoparticles Including Functionalization of Dodecylsulfide Stabilized Pd Nanoparticles with NHCs Palladium nanoparticles were prepared from PdCl$_2$ by a method demonstrated by Brust et al. [Brust, M., et al.,

*Journal of the Chemical Society—Chemical Communications* 1994, 801]. Dodecyl sulfide was used as a stabilizer in a two-phase preparation. $PdCl_2$ (0.24 mM) was mixed with 10 ml diluted HCl (0.5M) to form a Pd solution. Separately, tetraoctylammonium bromide (TOABr) (0.30 g), a phase transfer catalyst, was added to 20 mL of toluene. This TOABr mixture was added to the Pd solution and the resulting reaction mixture was stirred vigorously for 20 min. 0.5 mM of dodecyl sulfide was added to the reaction mixture and it was stirred for a further 20 minutes. An aqueous solution of $NaBH_4$ (1 mM, in 5 mL water) was added to the reaction mixture to reduce Pd(II) ions to Pd(0). Within a few seconds, the reaction mixture solution turned dark black confirming formation of Pd(0). Stirring was continued for 2 hrs to allow docecylsulfide stabilized Pd nanoparticles ("Pd-NP") to form. Size of the nanoparticles was controlled by varying the concentration of stabilizing agents. Table 4 lists concentration of stabilizing agents and size of resulting Pd nanoparticles.

Resulting dodecyl sulfide-stabilized Pd nanoparticles were treated with a NHC-1 solution. Dodecylsulfide-stabilized Pd nanoparticles (6 mg) were dispersed in 2 mL toluene by sonication for 5 minutes. A 10 mM solution of NHC-1 was prepared in 2 mL isopropanol. 2 mL of the Pd nanoparticle dispersion and 2 mL of the NHC-1 solution were then mixed together. The reaction mixture was maintained at room temperature for 24 hours with vigorous stirring. Following this time period, the nanoparticles were separated by centrifugation. Then the nanoparticles were washed in toluene using a sonicator and then separated by centrifugation. This washing and separating was repeated three times to remove loosely bound or mobile reagents.

FIG. 20 shows XPS data for NHC-terminated Pd nanoparticles. Spectra were identical from all nanoparticle size distributions. Residual S was observed for the NHC-1-Pd nanoparticles, as evidenced by the presence of the S 2p peak in the XPS spectra. A strong N 1s signal was also observed, which is consistent with binding of NHC-1 to the Pd nanoparticle surface. The relative atomic ratios of N:S and C:N as determined by XPS are indicated in Table 4. The C:N ratio in the two smaller nanoparticles is only slightly larger than the expected stoichiometric value of 6.5 (wherein only NHC would be on the surface). Unlike the Au nanoparticles, the S signal was not completely missing for the Pd nanoparticles. However, it was considered likely that dodecyl sulfide was no longer present in large quantities, otherwise a much higher C:N ratio would have been observed. The relatively small N:S ratio of the experimental results indicated that some S remains. Without wishing to be bound by theory, the inventors suggest that there may be some PdS within the outer shell of the nanoparticle.

Example 6. Computational Studies

Density functional theory (DFT) calculations were performed to examine structural features and binding energies of NHC-1 on gold slabs presenting the (111) surface (FIG. 4). To construct slabs, the face-centered cubic (fcc) unit cell of gold was optimized according a method described below. Resulting lattice constant was 4.107 Å, which is in good agreement with literature values of 4.080 Å [C. Kittel *Introduction to Solid State Physics*, 7$^{th}$ed. (John Wiley & Sons, New York, 1996)]. An Au (111) surface was cleaved from a bulk structure and a resulting hexagonal cell was repeated twice in lateral directions. The slabs used in these calculations were four layers thick. These tests showed this thickness was sufficient to converge surface energies to better than 1 $mJ/m^2$. The monomer was then added to the upper surface of the slab at positions corresponding to a-top, bridging, and three-fold sites. These structures were relaxed while keeping the positions of the gold atoms in the bottom two layers of the slab fixed at their bulk positions. Analogous calculations were performed on the bare slab, i.e. atoms in the upper two layers were relaxed while keeping those in the bottom two layers at fixed positions, and on the monomer, where all atoms were allowed to relax. The heights of the cells used in the calculations with the slab models were selected to ensure that at least 10 Å of vacuum space was present between periodic images. In addition, dipole correction techniques [Bengtsson, L. *Physical Review B* 59, 12301 (1999)] were employed to eliminate spurious electrostatic interactions between periodic images along a direction normal to the slabs.

All DFT calculations were performed using the PBEsol exchange correlation functional [Perdew, J. P., et al. *Phys. Rev. Lett.* 100, 136406 (2008)]. Core electrons were treated with projector augmented wavefunction potentials [Blöchl, P. E. *Physical Review B*, 50, 17953 (1994)] including scalar relativistic effects on all atoms. The valence states were represented with a planewave basis set expanded up to a kinetic energy cutoff of 40 Ry (Rydberg constant), and a kinetic energy cutoff of 400 Ry was used to represent the augmentation charges. This level of theory reproduces experimental Au—C bond lengths of selected compounds [Xu, X., et al. *Organometallics* 32, 164 (2013)] to within 0.012 Å. A 3×3×1 set of k-points was used in the calculations involving slabs. These details were sufficient to converge the total energies of the systems examined to better than 1 meV/atom. All calculations were performed with the Quantum-Espresso simulation package [Giannozzi, P., et al. *J. Phys.: Condensed Matter* 21, 395502 (2009)].

Example 6A: DFT Studies on C—Au Bond Strength

Bonding of NHC-1 at an Au(111) surface was simulated by DFT methods and was characterized by a very different bonding mode as compared to thiol SAMs. Details of the strength and nature of the interactions of NHC 1 with an Au(111) film on mica appear in FIG. 4. With respect to thiol-modified gold surfaces, thiols were typically expected to bind to gold via three-fold hollow (tetrahedral) sites [H. Häkkinen, *Nature Chem.* 4, 443 (2012)], with a reported binding energy of 127 kJ/mol [D. J. Lavrich, et al. *J. Phys. Chem. B* 102, 3456 (1998)]. However, with respect to the current DFT studies, the calculations indicated that this geometry lead to the least stable configuration for the NHC-gold surface, with an Au—C bond strength of 70.3 kJ/mol (FIG. 4, right). NHC-1 preferred to bind to a-top sites via a single gold-carbon bond (FIG. 4, centre), with a calculated bond strength of 149 kJ/mol, 22 kJ/mol greater than that of thiols on Au(111) [H. Häkkinen *Nature Chem.* 4, 443 (2012)]. The Au—C bond length was calculated to be 2.118 Å, which was fully consistent with that observed in molecular gold-NHC species [X. Xu, et al. *Organometallics* 32, 164 (2013)].

DFT results were consistent with the observation that an NHC-protected Au(111) surface was impervious to adsorption of thiols, but that a thiol-terminated surface could not be completely exchanged for NHC. Without wishing to be bound by theory, it has been suggested that both species compete for different binding sites on the surface, and the smaller thiol, sitting in the lower threefold hollow site, was more readily retained, while the larger NHC sits above it on the a-top site. The fact that a preformed NHC—Au surface was not affected by treatment with thiols under the conditions described as determined by XPS analysis implies that: (i) a gold-carbene bond was at least as strong as a gold-thiol bond; and (ii) once formed, NHC surface coverage was dense enough to prevent even dodecanethiol from penetrating and binding to sites not covered by the NHC.

Example 7. STM Characterization of Monolayer Formation

STM images of NHC-1 deposited on Au(111) films were characterized by densely packed SAMs with molecular-level resolution (FIG. 2A). Local ordering was apparent throughout the entire film. STM images of NHC-1 deposited on Au(111) from the carbonate salt were characterized by densely packed SAMS with molecular-level resolution exhibiting long-range ordering over many thousands of unit cells (FIG. 2B). Individual features were approximately 4.8 Å×3.4 Å, and were generally aligned along the shorter axis (FIG. 2A). This was consistent with the benzimidazole portion of the carbene sitting upright on the surface, and forming n-stacks with neighbouring molecules.

The STM images showed the presence of darker regions, one Au layer in depth, which were not present on the unreacted Au(111) film. These regions were areas in which restructuring of the Au surface had taken place, were analogous to the "etch pits" commonly seen on Au(111) surfaces treated with alkanethiols [C. Vericat, et al., Chem. Soc. Rev. 39, 1805 (2010)]. These were not defects in the SAM itself, and stacked NHCs could also be observed within the dark features (see FIG. 2A). The STM image of NHC-1 on Au(111) (FIGS. 2A and 2B) showed no evidence of islands. However, islands were clearly present in the STM image of NHC-3 on Au(111) (see FIG. 5). The density of darker regions was larger for NHC-3 compared with films prepared from NHC-1 (see FIGS. 6 and 7). This observation was consistent with NHC-3 forming a less well-ordered SAM, as the presence of a high density of step edges associated with islanding may be necessary to accommodate the bulky mesityl side groups of the NHC. Films of NHC-3 on Au(111) were characterized by IMes units (small bright spots) that were not self-assembled into ordered structures (FIG. 5). As the mesityl side groups of NHC 3 were considerably bulkier than the isopropyl groups of NHC-1, a less organized and more loosely packed SAM was expected at the Au(111) surface.

Example 8: Surface Functionalization

Aromatic substitution and $S_N^2$-chemistry permitted preparation of carbene NHC-6, an analog of NHC-1 in which an alkyl chain terminated with an azide functional group was attached to the benzimidazole unit (FIG. 3A). SAMs on Au(111) derived from NHC-6 were prepared, and the resulting azide-terminated surfaces were interrogated by XPS and contact angle measurements (FIG. 3). When films of NHC-6 on Au(111) were exposed to aqueous Cu solutions in the presence of the hydrophilic alkyne propargyl alcohol, the expected Huisgen cycloaddition (click reaction) took place resulting in the formation of triazole species on the SAM (FIG. 3A). The success of this reaction was monitored by XPS and contact angle measurements (FIGS. 3B and 3C). The latter technique confirmed that the azide-terminated surface with a contact angle of 78±3° was transformed to an alcohol-terminated surface with the expected contact angle of 45±3°. Treatment of the same surface in the absence of either Cu or the alkyne resulted in no discernible change in the contact angle.

XPS analysis of Au(111) surfaces modified by NHC-6 displayed three distinct signals in the N(1s) region of the spectrum, which were assigned to the two virtually identical nitrogen atoms comprising the N-heterocyclic carbene ring, the two terminal nitrogen atoms of the azide, and the very diagnostic central nitrogen of the azide (FIG. 3B). This latter atom appeared at significantly higher energy than the others since it is flanked by two other electronegative nitrogen atoms. Consistent with a successful Huisgen cycloaddition having occurred on the surface, this signal was lost after exposure of the surface to propargyl alcohol and Cu catalyst (FIG. 3C). After this reaction, the N(1s) region of the XPS spectrum was characterized by only two distinct types of N atoms, which was consistent with the transformation of the azide to a triazole, and the contact angle change was consistent with that of an alcohol-terminated surface.

Example 9. SPR Experiments with NHC-16 and Comparison to Commercial "HPA" Chip

A Surface Plasmon Resonance (SPR) chip was prepared by depositing a NHC-16 self-assembled monolayer on a blank Au chip (blank Au available from Biacore, General Electric, Pittsburgh, Pa., USA). The resulting chip was consequently coated with a hydrophobic layer, which can be used to form a model lipid layer on its surface. Such a lipid layer can be used for detection of biomolecules via SPR. Efficacy of said NHC-16 coated chip to form a lipid layer via lecithin adsorption was compared to the efficacy of a commercially available HydroPhobic Association (HPA) chip (available from Biacore), whose surface was coated with a long-chain octadecane-thiol, self-assembled monolayer on a gold surface in a flat, quasi-crystalline hydrophobic layer.

Example 9A. Stability Tests

The NHC-16 carbene-coated chip operated in a similar fashion to the HPA chip under a wide range of pH conditions. However, there were two important differences. The carbene-coated chip was stable. The chip was exposed to phosphate buffered saline (PBS) buffer, a solvent to which a SPR chip would be routinely exposed to in a typical experiment, at or above ambient temperatures. After exposure to PBS buffer at 65° C. for 24 hours, the carbene-coated chip's performance was unaffected. In contrast, the HPA chip was destroyed under these conditions.

Example 9B. Performance

The carbene-coated chip showed better performance since it allowed formation of a single layer of lecithin immediately upon exposure. In contrast, the HPA chip first adsorbed multilayered lecithin vesicles that had to be washed off the HPA chip's surface before it could be used further. The lecithin layer on the carbene-coated chip was highly reproducible from run to run. The lecithin layer on the carbene-coated chip was highly resistant to adsorption of BSA protein. BSA is a protein that is well known to undergo non-specific binding to bare Au: that is it undergoes indiscriminate physical adsorption to a hydrophobic surface due to strong attractive van der Waals' forces. This indicates that the NHC-16 coated chip's overlayer was complete since a non-specific binding protein such as BSA would be expected to adsorb on an incomplete overlayer in which bare hydrophobic sites remain. Performance of the carbene-coated chip equalled or exceeded the commercial HPA chip in this regard. See Tables 5A and 5B for comparison data between the HPA chip and the NHC chip. Notably, the carbene-coated chip was more robust and performed better than a commercially available HPA chip.

Example 9C. Preparation of Lipid Vesicles

Small unilamellar vesicles (SUV) were prepared in phosphate buffer (100 mM $Na_2HPO_4/NaH_2PO_4$, 150 mM NaCl, pH 7.4). The general protocol was as follows: Egg yolk L-α-phosphatidylcholine (9.0 mg, 2 mM) was dissolved into chloroform/methanol (2/1, v/v) in a vial. The solvent mixture was evaporated under a stream of nitrogen for at least 30 min, yielding a thin lipid film on the bottom of the vial. Lipid films were then thoroughly dried under vacuum for 2 h to remove the solvent mixture. Dried lipid films were hydrated by adding 6.0 mL of running buffer, and the mixture was then vortexed thoroughly until all lipid films were removed from the vial walls. A milky uniform suspension was obtained. Lipid suspensions were frozen in a dry ice/acetone bath for 8 min, followed by thawing in a water bath (80° C., 8 min). This freeze-thaw cycle was repeated 8 times. Resultant mixtures were then sonicated until suspensions changed from milky to nearly transparent, yielding a uniform suspension of small unilamellar vesicles with diameters of about 30 to about 35 nm.

Example 9D. Formation and Regeneration of Lipid Monolayers

Following equilibration of a chip sensor chip to room temperature, the chip was docked and primed with running buffer. All solutions for injection were freshly prepared, filtered through a 0.2 μm pore filter, and thoroughly degassed prior to use. Sensor surface was preconditioned by a 5-min injection of 40 mM n-Octyl β-D-glucopyranoside (OG) at a flow rate of 10 μL/min. SUV were injected immediately for a period of 25 min, followed by a 5-min dissociation with buffer. To remove any loosely bound vesicles, the flow rate was increased to 100 μL/min for a 1 min buffer rinse followed by a 5-min wash with 50 mM sodium hydroxide at 10 μL/min. A stable baseline was obtained, presumably corresponding to a lipid monolayer. Degree of surface coverage by lipids was evaluated by injecting 0.1 mg/mL BSA at a flow rate of 10 μL/min for 5 minutes to assess the quantity of non-specific binding [M. A. Cooper et al. *Biochimica et Biophysica Acta* 1373, 101-111 (1998)]. After each binding cycle, the sensor surface was regenerated by injecting 40 mM OG for 5 min. Stability of the sensor chips were assayed by repeated cycles of binding with egg PC SUV and regenerating with OG. The results shown in Tables 5A and 5B demonstrate that, under a wide range of pH conditions, that the carbene chip outperforms the commercial HPA chip in several ways: first, the magnitude of the reduction in phosphatidylcholine loading after the NaOH wash is significantly lower in the carbene chip, indicating that the phosphatidylcholine initially forms a monolayer on the carbene chip, while on the HPA chip it forms a series of vesicles that are removed during the NaOH wash and impede the quality of the overlayer. Secondly, the reproducibility of the loading in virtually all cases is superior in the carbene chip, as evidenced by the lower standard deviation (%) between runs. Thirdly, the extent of BSA bound to the surface is lower on the carbene chip, indicating a complete monolayer of phosphatidylcholine has been formed on the surface, in contrast to the HPA chip which shows a greater extent of BSA bonding, indicating bare hydrophobic sites remain.

Example 10. Carbenes as a Support for Water Oxidation Catalysis

Using carbonate carbene precursors, an azide-terminated carbene monolayer self-assembled on gold. Subsequently, a "click" reaction was performed on the azide to attach a chosen ligand system. Then an Ir-based water oxidation catalyst co-ordinated on the surface. Once formed, this catalyst's activity to water oxidation was demonstrated by Cerium Ammonium Nitrate method ("CAN"), which uses a sacrificial oxidant for water oxidation.

The transformations shown in Scheme 1 of FIG. 22 have been carried out (up to NHC-10). Intermediate compounds 1 to 6 and NHC-7 and NHC-8 have been characterized by XPS and/or NMR spectroscopy. NHC-10 has been used in preliminary experiments with CAN using UV-vis absorbance spectroscopy. These experiments show that NHC-10 is indeed active towards CAN destruction, and, with bubbles observed during this reaction, presumably water oxidation, and can undergo some degree of recycling.

Compound 2 was made by placing 1.541 g of compound 1 (10 mmol) and 1 eq of $K_2CO_3$ (1.382 g, 10 mmol) in a dry round bottom flask under Ar(g). 30 mL of dry acetonitrile was added to the flask and the mixture was stirred until all of compound 1 had dissolved. 3 equivalents of 1,6-dibromohexane (4.6 mL, 30 mmol, available from Sigma-Aldrich) were added. The resultant mixture was raised to 80° C. and was stirred overnight. The mixture was cooled to room temperature and concentrated under reduced pressure using a Rotary Evaporator (Buchi). The resulting residue was passed through a silica flash column using hexanes as the first eluent. After 100 mL of solvent the eluent was changed to 7:3 hexanes to ethyl acetate. The volume was reduced under reduced pressure using a Rotary Evaporator. A bright red solid was obtained (compound 2, 76% yield).

$^1$H NMR ($CDCl_3$) δ: 1.52 (m, 4H), 1.81 (q, J=7.0 Hz, 2H), 1.92 (q, J=7.0 Hz, 2H), 3.44 (t, J=6.5 Hz, 2H), 3.95 (t, J=6.5 Hz, 2H), 5.88 (s, 2H), 6.76 (d, J=9.1 Hz, 1H), 7.08 (dd, J=9.0, 2.9 Hz, 1H), 7.55 (d, J=2.9 Hz, 1H).

Compound 3 was prepared by placing compound 2 (1.1914 g or 5 mmol), iron powder (2.7925 g, 10 eq, 50 mmol), and ammonium chloride (2.674 g, 10 eq, 50 mmol) in a round bottom flask. Isopropanol (approximately 40 mL) was added to the flask until compound 2 dissolved. Then formic acid (19 mL, 100 eq, 500 mmol) was added slowly. The resultant mixture was raised to 90° C. and stirred under Ar(g) for three hours. The mixture was cooled to room temperature. Iron powder was separated by filtration and washed with 3×15 mL of isopropanol. Combined filtrates were collected and reduced under vacuum. The resultant residue was mixed with $NaHCO_3$ until all of the remaining formic acid had reacted. The reaction mixture was partitioned with dichloromethane and its non-aqueous layer was collected. The aqueous layer was washed three times with dichloromethane. Combined non-aqueous layers were dried over $MgSO_4$, filtered, and reduced under vacuum. A deep-orange solid was obtained (compound 3, 69% yield).

$^1$H NMR ($CDCl_3$) δ: 1.55 (m, 4H), 1.84 (m, 2H), 1.92 (m, 2H), 3.45 (t, J=6.8 Hz, 2H), 4.01 (t, J=6.4 Hz, 2H), 6.89 (dd, J=9.1, 1.9 Hz, 1H), 7.14 (d, J=1.9 Hz, 1H), 7.59 (d, J=1.9 Hz, 1H), 8.21 (s, 1H)

Compound 4 was made by placing compound 3 (0.7429 g, 2.5 mmol) in a dry round bottom flask with $NaN_3$ (0.1788 g, 1.1 eq, 2.75 mmol) and 25 mL of dry dimethylsulphoxide (DMSO). This mixture was stirred at room temperature for 4 hours. Reaction progress was followed by this layer chromatography. When all of the starting material was consumed, a saturated solution of NaHCO$_3$ (50 mL) was added to the mixture. The mixture was then filtered and the filtrate was removed. The resultant solid was washed with 3×25 mL of dichloromethane and its filtrate was collected and reduced under vacuum. Deep-orange solid was obtained (compound 4, 67% yield). $^1$H NMR (CDCl$_3$) δ: 1.50 (m, 4H), 1.66 (q, J=7.2 Hz, 2H), 1.84 (q, J=7.1 Hz, 2H), 3.30 (t, J=6.8 Hz, 2H), 4.00 (t, J=6.4 Hz, 2H), 6.95 (dd, J=8.7, 2.3 Hz, 1H), 7.11 (d, J=2.1 Hz, 1H), 7.56 (d, J=8.9 Hz, 1H), 8.02 (s, 1H)

Compound 5 was made by taking 0.388 g of 4 (1.5 mmol) and 0.4887 g of Cs$_2$CO$_3$ (1 eq, 1.5 mmol) in a dry pressure tube under Ar(g). Acetonitrile (5 mL) was added followed by 3.75 mL of isopropyl iodide (25 eq, 37.5 mmol), which was added drop-wise. The tube was then sealed with a TEFLON® lid. The reaction flask's temperature was raised to and maintained at 90° C. and the mixture was stirred overnight. The tube was allowed to cool to room temperature, and NaBF$_4$ (1.647 g) was added quickly. The tube was resealed and allowed to stir for 48 hours. The mixture was filtered and the collected solid was washed with dichloromethane. Combined filtrates were collected and their volume was reduced under vacuum. A crude sticky solid of compound 5 was crystalized using a mixture of ethyl acetate and hexane. This solid was used directly in the next step without further purification. $^1$H NMR (CDCl$_3$) δ: 1.55-1.68 (m, 8H), 1.89 (quart, J=3.3 Hz, 12H), 3.33 (t, J=6.6 Hz, 2H), 4.10 (t, J=6.2 Hz, 2H), 5.13 (m, 2H), 7.12 (s, 1H), 7.24 (s, 1H), 7.66 (d, J=9.1 Hz, 1H), 10.53 (s, 1H).

Compound 6 was prepared by taking the product 5 and adding 0.102 g of KHCO$_3$ in 5 mL of dry methanol in a TEFLON® capped vial. This was allowed to stir at room temperature for 48 hours. After this the mixture was reduced under vacuum and 5 mL of dichloromethane was added. This was then filtered through celite and crystalized with hexanes to give a sticky residue. This was then washed with more hexanes with sonication to give the solid 6. $^1$H NMR ((CD$_3$)$_2$CO) δ: 1.50 (m, 2H), 1.57 (m, 2H), 1.66 (m, 2H), 1.80 (m, 12H), 1.88 (m, 2H), 3.37 (t, J=6.4 Hz, 2H), 4.23 (t, J=6.4 Hz, 2H), 5.24 (m, 2H), 7.34 (d, J=9.4 Hz, 1H), 7.68 (s, 1H), 8.04 (d, J=9.4 Hz, 1H), 10.02 (s, 1H).

NHC-7 was made by taking compound 6 (1.88 mg) and dissolving it in dry methanol (4 mL). This solution was then added to a vial housing a gold-on-mica chip (available from Georg Albert PVD—Beschichtungen of Hauptstr, Germany). The vial was sealed with a TEFLON® cap. The vial and its contents were left to sit overnight. The next morning, the gold chip was washed with 150 mL of methanol and dried. XPS of the chip's surface was then measured. XPS ratio: $N_{BZMDZ}:N_{AZL}:N_{AZC}:C_R:C_{Ar}$ is 2:2:1:14:8, overall 5 nitrogen atoms per 22 carbon atoms, which is close to stoichiometric ratio (2:2:1:12:7).

NHC-8 was made by dissolving KOtBu (0.002 g) in 2 mL of dry DMSO. Then phenyl acetylene (0.01 mL) was added and the solution was swirled to combine. NHC-7 was submerged in the solution and the vial was sealed with a TEFLON® cap and the mixture was allowed to sit overnight at room temperature. The gold surface was then washed with 150 mL of methanol and dried.

NHC-9 was made by placing diphenyliodonium tetrafloroborate salt (0.037 g) and CuSO$_4$ (0.8 mg, 5 mol %) in a vial and dissolving them in 2 mL of dimethylformamide (DMF). NHC-8 was then added to the solution and the vial was sealed with a TEFLON® cap. The vial's contents' temperature was raised to and maintained at 100° C. overnight. In the morning, the vial was cooled to room temperature and the gold chip was washed with 150 mL of methanol and dried. XPS of this surface is in progress.

NHC-10 was prepared by placing NHC-9 in a Schlenk flask and placing it in a glove box having an Ar(g) atmosphere. Then 10 mg of [IrCp*Cl$_2$]$_2$ was added to the flask with a minimal amount of dry tetrahydrofuran (THF). NaHMDS (Sodium bis(trimethylsilyl)amide also known as sodium hexamethyldisilazide ((CH$_3$)$_3$Si)$_2$NNa) (18 mg) was added to a separate vial. It was dissolved in THF and the vial was capped with a rubber septum. The Schlenk flask and the vial were then removed from the glovebox. The Schlenk flask was placed under Ar(g) following standard Schlenk line techniques and was cooled to −78° C. using a dry ice bath. After 10 minutes, the NaHMDS solution in the vial, which was also under an Ar(g) atmosphere, was added to the Schlenk flask drop-wise via syringe. The resultant solution was allowed to come slowly to room temperature overnight. The next morning the gold chip was removed from solution, washed with 150 mL THF, and dried. XPS of this surface is in progress.

Example 11. Click Reaction of Mixed Monolayer

An experiment was performed wherein NHC-8 was present in 25% on a gold surface and the remaining SAM consisted of a 6-carbon chain alkyl derivative (collectively designated NHC-11 in Table 1). A click reaction was performed on this surface and was deemed successful. That is, the click reaction occurred at NHC-8 and not at the 6-carbon derivative. Thus a "diluted" catalyst can be used where only 25% of the molecules on the surface are the active catalyst (with iridium), the other 75% being a "filler" which is similar to the catalyst. The presence of the "filler" allows the mixture of catalyst and filler to form a SAM since interactions between the catalyst and the filler are similar to interactions between the catalyst and another catalyst. The experimental ratio shown below supports that the mixture was deposited in the same ratio that the compounds (catalyst and filler) were mixed in (25:75 ratio). XPS of this monolayer of mixed carbenes had an expected ratio C:N of 21.7:2.7, and an observed ratio of 23:3.

Example 12. Water Oxidation Studies Using Cerium Ammonium Nitrate and UV Absorbance Detection These experiments are intended to demonstrate that NHC-terminated metal samples are capable of oxidizing water. A sacrificial oxidant, cerium ammonium nitrate ("CAN"), was used both to complete the oxidation cycle and to track the progress of reaction by monitoring a UV-vis peak that is characteristic of the unreduced CAN.

In a first experiment, a NHC-terminated gold on mica sample was placed in a fresh solution of 7.5 mM cerium ammonium nitrate (CAN) in 0.5 M nitric acid ("acid" on FIG. 18A) in a quartz cuvette. The gold samples were coated with 100% NHC-15, 25% NHC-10 and 75% NHC-15, or 100% NHC-10. The cuvette was placed in a UV-vis spectrometer and the absorbance measured every 15 seconds for 6 hours at a wavelength of 420 nm. It was observed that the concentration of CAN decreased, and bubbles were formed, as time progressed; these results are indicative of water oxidation (see FIG. 18A).

In a second experiment, a 10 mL solution of 7.5 mM ceric ammonium nitrate (CAN) in 0.5M HNO$_3$ was prepared fresh and 3.8 mL of the solution was added to a quartz cuvette. A NHC-terminated gold on silicon sample was placed in the solution, and coated with 100% NHC-15. The solution's absorbance was measured every 15 seconds, for 3 hours, at a wavelength of 420 nm. Following this, 15.6 mg of CAN was added directly to the cuvette and absorbance was again measured every 15 seconds for 3 hours at 420 nm. This was repeated until a total of 5 runs in total were measured (See FIG. 18B).

Example 13. NHC Deposition on Nickel and Tungsten

Nickel (Ni) foil was cut into pieces 1 cm$^2$. Tungsten (W) wire (2 mm diameter) was cut into 1 cm lengths. These metal samples were cleaned with acetone and then ethanol. A solution of carbonate salt of NHC-1 (1-2 mmol) was prepared in ethanol. The Ni foil and W wire samples were each immersed into 5 mL of the NHC-1 solution for a period of 24 hours at 25° C. Each Ni and W sample was then removed from their respective solutions, rinsed with ethanol and air-dried. Resulting XPS spectra indicated that NHC-1 had deposited on the metal's surface. See FIG. 19.

Example 15. Stability of Carbene Monolayers in Decalin at 100° C. and 190° C.

NHC-1 functionalized surfaces were placed in Ace Glass pressure tubes, and 2 mL of decalin was added. The tubes were purged with nitrogen gas, sealed and heated at either 100° C., or 190° C. for 24 h. After this time, the samples were cooled to room temperature, rinsed with hexane (2×5 mL), ether (2×5 mL), and ethanol (2×5 mL), dried under a nitrogen gas stream, and analysed by XPS. The samples treated at 100° C. showed no discernible change, while the samples treated at 190° C. showed decomposition (see FIGS. 21A and 21B).

TABLE 1

Structural information for NHCs on metal.

| Nickname | Structure | Name of NHC/salt | Prepared from |
|---|---|---|---|
| NHC-1 on gold | 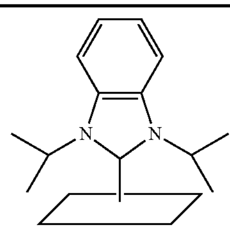 | 1,3-dihydro-1,3-bisisopropyl-benzimidazol-2-ylidene (also known as "IPrBenz") | |
| Monolayer prepared using hydrogen carbonate salt of NHC-1 | 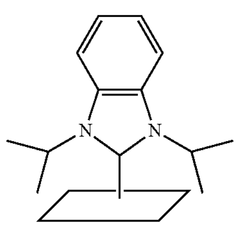 | 1,3-dihydro-1,3-bisisopropyl-benzo[d]imidazolium hydrogen carbonate | |
| NHC-2 on gold | 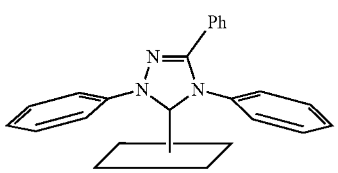 | 2,4-dihydro-2,4,5-triphenyl-1,2,4-triazol-3-ylidene (also known as "Enders' carbene") | |
| Monolayer prepared using hydrogen carbonate salt of NHC-3 | 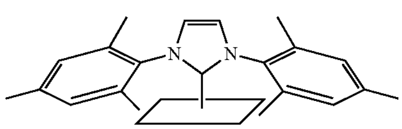 | 1,3-dihydro-1,3-bis(2,4,6-trimethylphenyl)imidazolium hydrogen carbonate | |
| NHC-3 on gold | 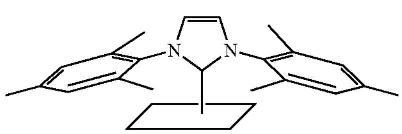 | 1,3-dihydro-1,3-bis(2,4,6-trimethylphenyl)imidazol-2-ylidene (also known as "IMes"); | |
| NHC-4 | 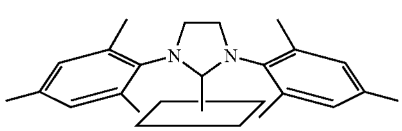 | 1,3-bis(2,4,6-trimethylphenyl)imidazolin-2-ylidene (also known as "SIMes") | |

TABLE 1-continued

Structural information for NHCs on metal.

| Nickname | Structure | Name of NHC/salt | Prepared from |
|---|---|---|---|
| NHC-5A | 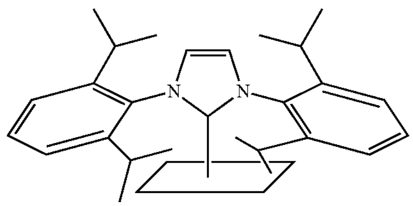 | 1,3-dihydro-1,3-bis(2,6-diisopropyl-phenyl)imidazol-2-ylidene (also known as "IPr") | |
| Monolayer prepared using hydrogen carbonate salt of NHC-5A | 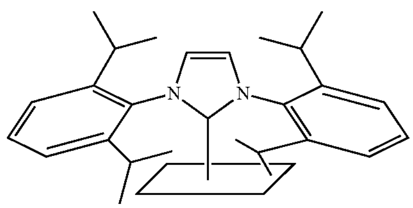 | 1,3-dihydro-1,3-bis(2,6-diisopropyl-phenyl)imidazol-ium hydrogen carbonate | |
| NHC-5B on gold | 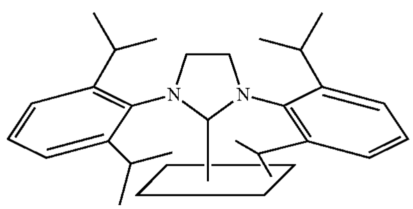 | 1,3-bis(2,6-diisopropylphen-yl)imidazolidine-2- | |
| NHC-6 on gold | 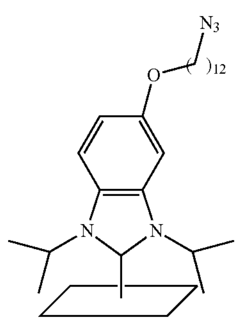 | 1,3-diisopropyl-5-(12-(azido)dodecyl-oxy)-1H-benzo[d]imidaz-ole-2-ylidene | |
| NHC-7 | 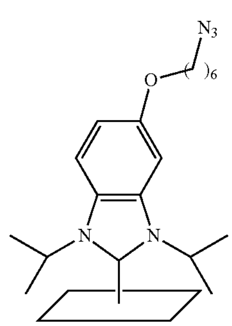 | 5-(6-azidohexyloxy)-1,3-diisopropyl-2,3-dihydro-1H-benzo[d]imidaz-ole-2-ylidene | |

TABLE 1-continued

Structural information for NHCs on metal.

| Nickname | Structure | Name of NHC/salt | Prepared from |
|---|---|---|---|
| Monolayer prep'd using hydrogen carbonate salt of NHC-7 | (structure) | 5-((6-azidohexyl)oxy)-1,3-diisopropyl-benzo[d]imidaz-olium hydrogen carbonate | (structure with HCO$_3^-$) |
| Product of click chemistry on NHC-6, which is referred to herein as NHC-6A | (structure) | | |
| NHC-8 | (structure) | | |

TABLE 1-continued

Structural information for NHCs on metal.

| Nickname | Structure | Name of NHC/salt | Prepared from |
|---|---|---|---|
| NHC-9 | 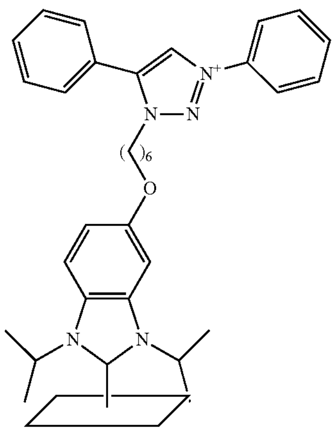 | | |
| NHC-10 | 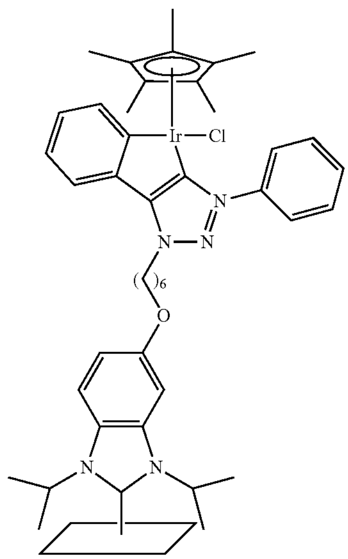 | | |
| NHC-11 | 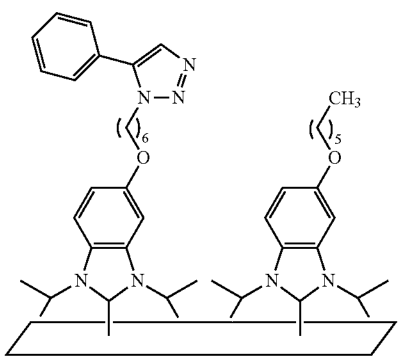 | | |
| Monolayer prep'd using hydrogen carbonate salt of NHC-13 | 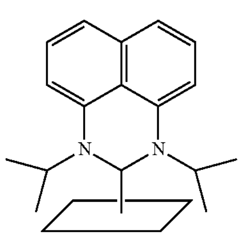 | 1,3-diisopropyl-perimidinium hydrogen carbonate | |

TABLE 1-continued

Structural information for NHCs on metal.

| Nickname | Structure | Name of NHC/salt | Prepared from |
|---|---|---|---|
| Monolayer prep'd using hydrogen carbonate salt of NHC-14 | 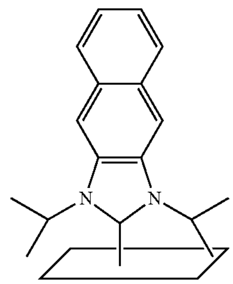 | 1,3-diisopropyl-naphtho[2,3-d]imidazolium hydrogen carbonate | |
| NHC-15 | 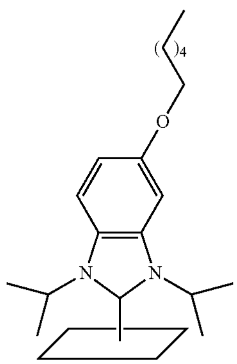 | 5-(hexyloxy)-1,3-diisopropyl-2,3-dihydro-1H-benzo[d]imidazol-2-ylidene | |
| Monolayer prep'd using hydrogen carbonate salt of NHC-15 | 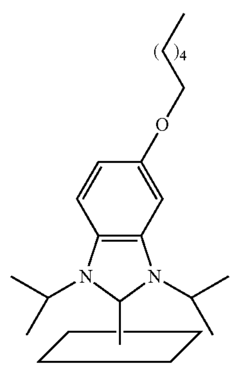 | 5-(hexyloxy)-1,3-diisopropyl-benzo[d]imidazolium hydrogen carbonate | |
| NHC-16 | 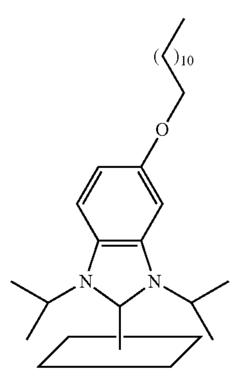 | 5-(dodecyloxy)-1,3-diisopropyl-2,3-dihydro-1H-benzo[d]imidazol-2-ylidene | |

TABLE 1-continued

Structural information for NHCs on metal.

| Nickname | Structure | Name of NHC/salt | Prepared from |
|---|---|---|---|
| Monolayer prep'd using hydrogen carbonate salt of NHC-16 | 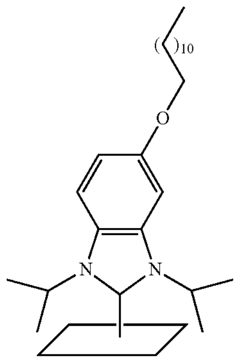 | 5-(dodecyloxy)-1,3-diisopropyl-benzo[d]imidaz-olium hydrogen carbonate | |
| Monolayer prep'd using hydrogen carbonate salt of NHC-17 on gold | 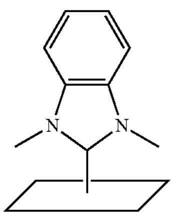 | 1,3-dimethyl-benzo[d]imidaz-olium hydrogen carbonate | |
| Monolayer prep'd using hydrogen carbonate salt of NHC-18, on gold | 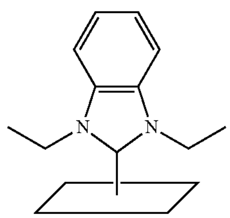 | 1,3-diethyl-benzo[d]imidaz-olium hydrogen carbonate | |
| NHC-18 on gold | 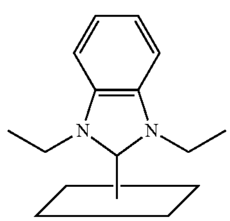 | 1,3-diethyl-2,3-dihydro-1H-benzo[d]imidaz-ol-2-ylidene | |

TABLE 2A

XPS data for products obtained by reacting NHCs with Au(111) surfaces and Au nanoparticles

| Carbene | N:C ratio (XPS) | | |
|---|---|---|---|
| | | Found | |
| NHC on GOLD | Expected | Au(111) | Au$_{NP}$ |
| NHC-1 | 2:13 | 2:14 | 2:13 |
| NHC-2 | 3:20 | 3:21 | 3:22 |
| NHC-3 | 2:21 | 2:21 | 2:23 |
| NHC-4 | 2:21 | 2:22 | 2:22 |
| NHC-5A | 2:27 | 2:29 | 2:27 |

TABLE 2B

C and N XPS spectra for the carbonate salts of various carbenes self-assembled on Au.

| | N:C ratio | |
|---|---|---|
| | Expected | Found |
| NHC-1 | 2:13 | 2:13 |
| NHC-3 | 2:21 | 2:22 |
| NHC-5A | 2:27 | 2:27 |
| NHC-5B | 2:27 | 2:26 |
| NHC-7 | 5:19 | 5:22 |
| NHC-13 | 2:17 | 2:17 |
| NHC-14 | 2:17 | 2:17 |
| NHC-15 | 2:19 | 2:18 |
| NHC-16 | 2:25 | 2:26 |
| NHC-18 | 2:11 | 2:12 |

TABLE 4

Characterization of NHC-1-substituted Pd nanoparticles.

| Pd nanoparticle sample | Nanoparticle diameter (nm) | Stabilizing Agent Concentration (mM) | XPS Peak Position | | N:S ratio | C:N ratio |
|---|---|---|---|---|---|---|
| | | | N 1 s | S 2 p | | |
| Pd NP-X-NHC | 1.5-2.5 | 2.0 | 400.06 | 163.06 | 2.6:1 | 7.7:1 |
| Pd NP-Y-NHC | 2.5-4 | 0.5 | 400.65 | 163.46 | 4.8:1 | 7.3:1 |
| Pd NP-Z-NHC | 4-5.5 | 0.12 | 400.21 | 163.09 | 6.7:1 | 13.5:1 |

TABLE 5A

Loading of HPA sensor chip and NHC-16 Carbene sensor chip with PC (phosphatidylcholine) SUV (35 nm) for 4 cycles in the listed buffer.

| Buffer | pH | Sensor chip | Initial loading (RU) | Initial loading (RU) After bulk shift subtraction | Loading after NaOH wash (RU) | BSA bound (RU) |
|---|---|---|---|---|---|---|
| Citrate | 5.0 | HPA | 3924 ± 222 (5.66%) | 3789 ± 217 (5.73%) | 2598 ± 145 (5.58%) | 274 ± 85 (31.02%) |
| | | Carbene | 1893 ± 50 (2.64%) | 1523 ± 41 (2.69%) | 1449 ± 31 (2.14%) | 101 ± 9 (8.91%) |
| PBS | 7.4 | HPA | 9340 ± 391 (4.19%) | 8930 ± 386 (4.32%) | 1579 ± 25 (1.58%) | 60 ± 38 (63.33%) |
| | | Carbene | 1671 ± 41 (2.45%) | 1530 ± 24 (1.57%) | 1325 ± 34 (2.57%) | 54 ± 8 (14.81%) |
| HEPES | 8.0 | HPA | 2600 ± 543 (20.88%) | 2350 ± 539 (22.94%) | 1348 ± 24 (1.78%) | 22 ± 12 (54.55%) |
| | | Carbene | 1244 ± 26 (2.10%) | 991 ± 31 (3.13%) | 909 ± 32 (3.52%) | 79 ± 4 (5.06%) |
| TE | 8.0 | HPA | 804 ± 33 (4.10%) | 563 ± 40 (7.10%) | 516 ± 40 (7.75%) | 212 ± 13 (6.13%) |
| | | Carbene | 937 ± 30 (3.20%) | 662 ± 36 (5.44%) | 592 ± 27 (4.56%) | 96 ± 4 (4.17%) |
| CAPS | 10.0 | HPA | 846 ± 32 (3.78%) | 571 ± 18 (3.15%) | 451 ± 14 (3.10%) | 309 ± 9 (2.91%) |
| | | Carbene | 1366 ± 18 (1.31%) | 1063 ± 20 (1.88%) | 939 ± 33 (3.51%) | 42 ± 5 (11.90%) |

TABLE 5B

Chip Stability Test: Loading of HPA sensor chip and Carbene sensor chip with PC SUV (35 nm) for 4 cycles after 24 h 65° C. in oven in PBS buffer (pH 7.4).

| Buffer | pH | Sensor chip | Initial loading (RU) | Initial loading (RU) After bulk shift subtraction | Loading after NaOH wash (RU) | BSA bound (RU) |
|---|---|---|---|---|---|---|
| PBS | 7.4 | Carbene 24 h 65° C. | 1880 ± 22 (1.17%) | 1502 ± 19 (1.26%) | 1364 ± 54 (3.96%) | 61 ± 9 (14.75%) |

Notes on Tables 5A and 5B:
Values given as response units with standard deviations (SD) and relative standard deviations (RSD) for n=4.
Lower percentage indicates a lower variability in the data set. Equally, higher percentage indicates the data set is more varied.
PBS: 100 mM $Na_2HPO_4/NaH_2PO_4$, 150 mM NaCl.
Citrate: 100 mM Citric acid/$Na_2HPO_4$.
HEPES: 10 mM N-(2-hydroxyethyl) 1-piperazine-N'-(2-ethanesulphonic acid), 100 mM NaCl.
TE: 10 mM Tris-HCl, 1 mM EDTA.
CAPS: 10 mM 3-(Cyclohexylamino)-1-propanesulfonic acid, 150 mM NaCl.

All publications, patents and patent applications mentioned herein are indicative of the level of skill of those skilled in the art to which this invention pertains and are herein incorporated by reference to the same extent as if each individual publication, patent, or patent applications was specifically and individually indicated to be incorporated by reference.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

We claim:

1. A carbene-functionalized composite, comprising:
   1,3-dihydro-1,3-bisisopropyl-2H-benzimidazol-2-ylidene carbene coating on a flat metal surface on a support; wherein the metal is selected from the group consisting of gold, palladium, platinum, and ruthenium, and
   wherein the 1,3-dihydro-1,3-bisisopropyl-2H-benzimidazol-2-ylidene carbene interacts with the metal surface to form a densely packed carbene monolayer coating that exhibits long-range ordering and is thermally stable at 100° C. for 24 hours, and
   wherein the metal surface is selected from the group consisting of bulk metal, solid metal, atomically ordered metal surface, metal film, metal sheet, and metal layer, and is not a nanoparticle.

2. The composite of claim 1, wherein the carbene monolayer coating comprises ≤5% contamination.

3. The composite of claim 2, wherein the carbene monolayer coating comprises ≤2% contamination.

4. The composite of claim 1, wherein the support is mica, alumina, silica, titania, silicon, glass, indium tin oxide, or any combination thereof.

5. The composite of claim 1, wherein the composite is a surface plasmon resonance (SPR) detector chip.

6. The composite of claim 1, further comprising a non-metal surface.

* * * * *